US007550501B2

(12) United States Patent
Chow et al.

(10) Patent No.: US 7,550,501 B2
(45) Date of Patent: Jun. 23, 2009

(54) COMPOUNDS AND METHODS FOR TREATING TOLL-LIKE RECEPTOR 2-RELATED DISEASES AND CONDITIONS

(75) Inventors: Jesse Chow, Hooksett, NH (US); Fabian Gusovksy, Andover, MA (US); Lynn Hawkins, Concord, MA (US); Mark Spyvee, Hampstead, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/697,651

(22) Filed: Apr. 6, 2007

(65) Prior Publication Data
US 2007/0167409 A1    Jul. 19, 2007

Related U.S. Application Data

(62) Division of application No. 10/973,164, filed on Oct. 25, 2004, now Pat. No. 7,202,234.

(60) Provisional application No. 60/514,283, filed on Oct. 24, 2003.

(51) Int. Cl.
*A61K 31/661* (2006.01)
*A61K 31/4045* (2006.01)
(52) U.S. Cl. ........................... 514/419; 514/80
(58) Field of Classification Search .................. 514/80, 514/419; 548/414; 568/14; 558/169
See application file for complete search history.

(56) References Cited

U.S. PATENT DOCUMENTS

| 6,569,896 B2 | 5/2003 | Dalton et al. |
| 6,835,721 B2 | 12/2004 | Hawkins et al. |
| 7,202,234 B2 | 4/2007 | Chow et al. |

FOREIGN PATENT DOCUMENTS

| EP | 1 147 117 | 6/2004 |
| WO | WO 98/50547 | 11/1998 |
| WO | WO 03/020760 A1 | 3/2003 |

OTHER PUBLICATIONS

Hoffman et al. Nature Reviews Drug Discovery, 2005, 4, 879-880.*
International Search Report and Written Opinion from International Application No. PCT/US04/35447 dated Feb. 7, 2005 and mailed Jun. 7, 2005.
Mel'nik et al., "Complex Lipids," Zhurnal Obshchei Khimi 37:2452-2455, 1967.
Yang et al. "Toll-like Receptor-2 Mediates Lipopolysaccharide-Induced Cellular Signaling," Nature 395(6699):284-288, 1998.
Rock et al., "A Family of Human Receptors Structurally Related to Drosophila Toll," *Proc Natl Acad Sci USA*. 95(2): 588-93, 1998.
Schwandner et al., "Peptidoglycan- and Lipoteichoic Acid-Induced Cell Activation is Mediated by Toll-Like Receptor 2," *J Biol Chem.* 274 (25): 17406-9, 1999.

Yoshimura et al., "Cutting Edge : Recognition of Gram-Positive Bacterial Cell Wall Components by the Innate Immune System Occurs via Toll-Like Receptor 2," *Immunol.* 163(1): 1-5, 1999.
Aliprantis et al., "Cell Activation and Apoptosis by Bacterial Lipoproteins Through Toll-Like Receptor-2", *Science* 285(5428): 736-9, 1999.
Brightbill et al., "Host Defense Mechanisms Triggered by Microbial Lipoproteins Through Toll-Like Receptors," 285(5428): 732-6, 1999.
Tekeuchi et al., "Differential Roles of TLR2 and TLR4 in Recognition of Gram-Negative and Gram-Positive Bacterial Cell Wall Components," *Immunity* 11(4): 443-51, 1999.
Underhill et al., "The Toll-Like Receptor 2 is Recruited to Macrophage Phagosomes and Discriminates Between Pathogens," *Nature* 401(6755):811-5, 1999.
Lien et al., "Toll-Like Receptor 2 Functions as a Pattern Recognition Receptor for Diverse Bacterial Products," *J Biol Chem.* 274(47): 33419-25, 1999.
Kim et al., "Activation of Toll-Like Receptor 2 in Acne Triggers Inflammatory Cytokine Responses," *J Immunol.* 169(3): 1535-41, 2002.
Asai et al., "Bacterial Fimbriae and Their Peptides Activate Human Gingival Epithelial Cells Through Toll-Like Receptor 2," *Infect Immun.* 69(12): 7387-95, 2001.
Zuany-Amorim et al., "Toll-Like Receptors as Potential Therapeutic Targets for Multiple Diseases," *Nat Rev Drug Discov.* 1(10):797-807, 2002.
Flo et al. "Human Toll-Like Receptor 2 Mediated Monocyte Activation by *Listeria monocytogenes*, but Not by Group B Streptococci or Lipopolysaccharide," *J Immunol.* 164(4):2064-9, 2000.
Decker, "Sepsis: Avoiding Its Deadly Toll," *J Clin Invest.* 113(10):1473-81, 2004.
Spyvee et al., "Toll-Like Receptor 2 Antagonists. Part 1: Preliminary SAR Investigation of Novel Synthetic Phospholipids," *Bioorg Med Chem Lett.* 15(24):5494-8. 2005.
Bsibsi et al., "Broad Expression of Toll-Like Receptors in the Human Central Nervous System," *J Neuropathol Exp Neurol.* 61(11): 1013-21. 2002.
Marshak-Rothstein, "Toll-Like Receptors in Systemic Autoimmune Disease," *Nat Rev Immunol.* 6(11):823-35, 2006.
Ingalls et al., "Differential Roles of the TLR2 and TLR4 in the Host Response to Gram-Negative Bacteria: Lessons from a Lipopolysaccharide-Deficient Mutant of Neisseria Meningitidis," *J Endotoxin Res.* 6(5):411-5, 2000.
Kang et al., "Detection of Toll-Like Receptor 2 (TLR2) Mutation in the lepromatous Leprosy Patients," *FEMS Immunol Med Microbiol.* 31(1): 53-8, 2001.
Baker et al., "Normal Keratinocytes express Toll-Like Receptors (TLRs) 1, 2 and 5: Modulation of TLR Expression in Chronic Plaque Psoriasis," *Br J Dermatol.* 148(4): 670-9, 2003.
Wetzler, "The Role of Toll-Like Receptor 2 in Microbial Disease and Immunity," *Vaccine.* 1;21 Suppl 2:S55-60, 2003.
McNamara et al., "Signaling Networks Controlling Mucin Production in Response to Gram-Positive and Gram-Negative Bacteria," *Glycoconi J.* 8(9):715-22, 2001.

(Continued)

*Primary Examiner*—Rebecca L Anderson
*Assistant Examiner*—Jason Nolan
(74) *Attorney, Agent, or Firm*—Clark & Elbing LLP

(57) ABSTRACT

The present invention relates to compounds and methods useful in the prevention or treatment of diseases or conditions associated with Toll-like receptor 2 activation.

34 Claims, No Drawings

OTHER PUBLICATIONS

Meng et al., "Antagonistic Antibody Prevents Toll-Like Receptor 2-Driven Lethal Shock-Like Syndromes," *J Clin Invest.* 113(10):1387-9, 2004.

Asea et al., "Novel Signal Transduction Pathway Utilized by Extracellular HSP70: Role of Toll-Like Receptor (TLR) 2 and TLR4," *J Biol Chem.* 277(17):15028-34, 2002.

Sobek et al., "Direct Toll-Like Receptor 2 Mediated Co-Stilmulation of T Cells in the Mouse System as a Basis for Chronic Inflammatory Joint Disease," *Arthritis Res Ther.* 6(5):R433-46, 2004.

Marshall et al., "Toll-Like Receptor-Mediated Activation of Mast Cells: Implications for Allergic Disease?," *Int Arch Allergy Immunol.* 132(2):87-97, 2003.

Seya et al., "A Lipoprotein Family from *Mycoplasma fermentans* Confers Host Immune Activation Through Toll-Like Receptor 2," *Int J Biochem Cell Biol.* 34(8): 901-6, 2002.

Fusunyan et al., "Evidence for an Innate Immune Response in the Immature Human Intestine: Toll-Like Receptors on Fetal Enterocytes," *Pediatr Res.* 49(4): 589-93, 2001.

Murray et al., "Lipopolysaccharide from the Periodontal pathogen *Porphyromonas gingivalis* Prevents Apoptosis of HL60-Derived Neutrophils In Vitro," *Infect Immun.* 71(12): 7232-5, 2003.

Wedzicha, "Exacerbations: Etiology and Pathophysiologic Mechanisms," *Chest.* 121(5 Suppl):136S-141S, 2002.

Pålsson-McDermott et al., "The Potential of Targeting Toll-Like Receptor 2 in Autoimmune and Inflammatory Diseases," *Ir J Med Sci.* 176(4):253-60, 2007.

Edfeldt et al., "Expression of Toll-Like Receptors in Human Atherosclerotic Lesions: A Possible Pathway for Plaque Activation," *Circulation.* 105(10): 1158-61, 2002.

McInturff et al., "The Role of Toll-Like Receptors in the Pathogenesis and Treatment of Dermatological Disease," *J Invest Dermatol.* 125(1):1-8, 2005.

* cited by examiner

COMPOUNDS AND METHODS FOR TREATING TOLL-LIKE RECEPTOR 2-RELATED DISEASES AND CONDITIONS

CROSS-REFERENCE TO RELATED APPLICATIONS

This application is a divisional of, and claims priority from, U.S. patent application Ser. No. 10/973,164, filed Oct. 25, 2004 (U.S. Pat. No. 7,202,234), which claims the benefit of the filing date of U.S. provisional patent application No. 60/514,283, filed Oct. 24, 2003, the contents of which are incorporated by reference herein in their entirety.

FIELD OF THE INVENTION

This invention relates to the prevention and treatment of diseases and conditions associated with Toll-like receptor 2 activation.

BACKGROUND OF THE INVENTION

The vertebrate immune system protects the body against undesirable foreign matter that enters the body, such as infecting pathogens (e.g., bacteria, viruses, fungi, and parasites) and their by-products. One manner by which this takes place involves the adaptive immune system, through which the body recognizes foreign antigens and generates specific immune responses against them. The induction of adaptive immunity takes time (e.g., 2-3 days post infection), and thus could leave the body vulnerable to the adverse effects of early infection, if it were not for the action of another division of the immune system, the innate immune system.

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. These receptors are known as Toll-like receptors (TLRs), due to their homology with receptors that were first identified and named in *Drosophila*, and are present in cells such as macrophages, dendritic cells, and epithelial cells.

There are at least ten different TLRs in mammals, and ligands and corresponding signaling cascades have been identified for some of these receptors. For example, TLR2 is activated by the lipoprotein of bacteria (e.g., *E. coli*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines.

SUMMARY OF THE INVENTION

The present invention provides compounds and methods for use in preventing or treating diseases or conditions characterized by Toll-like receptor 2 (TLR2) activation in patients. Accordingly, in a first aspect, the invention features a compound of formula I:

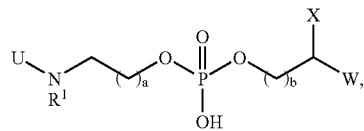

or a pharmaceutically acceptable salt or prodrug thereof, where a is an integer of 1 to 3;

b is an integer of 0 to 4, wherein when b is 0, the carbon bonded to X and W is not bonded to 2 or more heteroatoms;

$R^1$ is H or $C_{1-6}$ alkyl;

X is selected from the group consisting of —$NR^{X1}V$, —$N(R^{X1})C(O)V$, —$N(R^{X1})C(S)V$, —$N(R^{X1})C(O)N(R^{X2})V$, —$N(R^{X1})C(S)N(R^{X2})V$, —$N(R^{X1})C(O)OV$, —$N(R^{X1})S(O)_2V$, —$C(O)N(R^{X1})V$, —$C(O)OV$, —$OC(O)V$, —$OC(O)OV$, and —$OC(O)N(R^{X1})V$, where each of $R^{X1}$ and $R^{X2}$ is, independently, H or $C_{1-6}$ alkyl, and V is a $C_{1-20}$ alkyl, $C_{1-20}$ alkenyl, or $C_{1-20}$ alkynyl group, optionally substituted with halo, hydroxyl, $C_{1-21}$ acyloxy, oxo, $C_{1-20}$ alkoxyl, or $C_{1-20}$ thioalkoxyl, and optionally contains 1 to 2 phenyl or biphenyl moieties in and/or at the end of the carbon chain;

W is selected from the group consisting of H, —$C(O)N(R^{W1})R^{W2}$, —$C(O)OR^{W2}$, —$(CH_2)_cOR^{W3}$, —$(CH_2)_cSR^{W3}$, —$(CH_2)_cO(CH_2)_dCH(OR^{W3})R^{W4}$, —$(CH_2)_cS(CH_2)_dCH(OR^{W3})R^{W4}$, —$C(O)N(R^{W1})(CH_2)_cCH(OR^{W3})R^{W4}$, and —$C(O)N(R^{W1})(CH_2)_cCH(OR^{W3})(CH_2)_eOR^{W5}$, where each of c and d is an integer of 1 to 4, e is an integer of 2 to 4, $R^{W1}$ is H or $C_{1-6}$ alkyl, $R^{W2}$ is $C_{1-20}$ alkyl, $C_{1-20}$ alkenyl, or $C_{1-20}$ alkynyl, each of $R^{W3}$ and $R^{W5}$ is, independently, H, $C_{1-20}$ alkyl, $C_{1-21}$ acyl, $C_{1-20}$ alkenyl, or $C_{1-20}$ alkynyl, and $R^{W4}$ is H, $C_{1-20}$ alkyl, $C_{1-20}$ alkenyl, or $C_{1-20}$ alkynyl, where each of $R^{W2}$, $R^{W3}$, $R^{W4}$, and $R^{W5}$ is optionally substituted with halo, hydroxyl, $C_{1-21}$ acyloxy, oxo, $C_{1-20}$ alkoxyl, or $C_{1-20}$ thioalkoxyl, optionally contains 1 to 2 phenyl or biphenyl moieties in and/or at the end of the carbon chain, and optionally contains 1 to 4 non-vicinal oxygen atoms in the carbon chain; and U is selected from the group consisting of

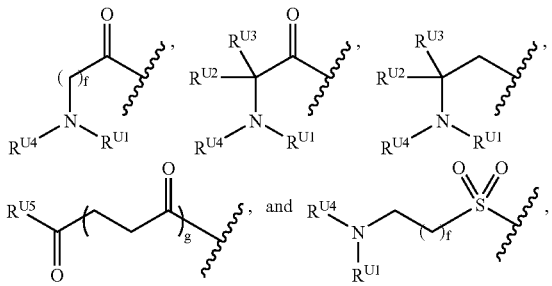

where f is an integer of 1 to 4, g is an integer of 0 to 1, each of $R^{U1}$, $R^{U2}$, and $R^{U3}$ is, independently, H, optionally substituted $C_{1-6}$ alkyl, optionally substituted $C_{7-16}$ aralkyl, or optionally substituted $C_{2-15}$ heterocyclylalkyl, or $R^{U1}$ is H or optionally substituted $C_{1-6}$ alkyl and $R^{U2}$ and $R^{U3}$ together with the carbon atom they are bonded to form an optionally substituted $C_{3-6}$ aliphatic ring, or $R^{U2}$ is H and $R^{U3}$ and $R^{U1}$ together with the carbon atom bonded to $R^{U3}$ and the nitrogen atom bonded to $R^{U1}$ form an optionally substituted 4-6-membered heterocyclic ring, $R^{U4}$ is selected from the group consisting of —$CH_2R^{U5}$, —$C(O)R^{U6}$, —$C(O)NH(R^{U7})$, and —$C(O)O(R^{U8})$, where each of $R^{U5}$, $R^{U6}$, $R^{U7}$, and $R^{U8}$ is selected from the group consisting of optionally substituted $C_{1-6}$ alkyl, optionally substituted $C_{2-6}$ alkenyl, optionally substituted $C_{2-6}$ alkynyl, optionally substituted $C_{7-16}$ aralkyl, optionally substituted $C_{2-15}$ heterocyclylalkyl, optionally substituted $C_{6-10}$ aryl, and optionally substituted $C_{1-9}$ heterocyclyl, or $R^{U4}$ is a peptide chain of 1 to 10 natural or non-natural amino acids, or mixture thereof, linked via the C-terminal end and substituted at the N-terminal end of the peptide with a group selected from H, —$CH_2R^{U5}$, —$C(O)R^{U6}$, —$C(O)NH(R^{U7})$, and —$C(O)O(R^{U8})$, where each of $R^{U5}$, $R^{U6}$, $R^{U7}$, and $R^{U8}$ is as defined above, and $R^{U5}$ is a peptide chain of 1 to 10 natural or non-natural amino acids, or mixture thereof, linked via the N-terminal end and the C-terminal end is $CO_2R^{U9}$, or $CONR^{U10}R^{U11}$, where each of $R^{U9}$, $R^{U10}$, and $R^{U11}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{7-16}$ aralkyl, optionally substituted $C_{2-15}$ heterocyclylalkyl, optionally substituted $C_{6-10}$ aryl, and optionally substituted $C_{1-9}$ heterocyclyl.

In a second aspect, the invention features a compound of formula II:

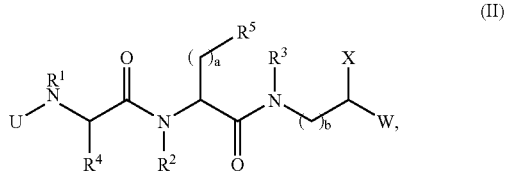

(II)

or a pharmaceutically acceptable salt or prodrug thereof, where each of a, b, U, X, and W is as defined above for the compound of formula I; each of $R^1$, $R^2$, and $R^3$ is, independently, H or $C_{1-4}$ alkyl; $R^4$ is H, optionally substituted $C_{1-6}$ alkyl, optionally substituted $C_{7-16}$ aralkyl, or optionally substituted $C_{2-15}$ heterocyclylalkyl; and $R^5$ is $CO_2H$, $SO_3H$, $OP(O)(OH)_2$, $OSO_3H$, or 5-tetrazolyl.

In an embodiment of either the first or second aspect of the invention, X or W contains at least one linear alkyl moiety of 7 or more carbons. Preferably, each of X and W contains at least one linear alkyl moiety of 7 or more carbons.

Examples of compounds of the invention where W contains at least one linear alkyl moiety of 7 or more carbons include those compound in which W is selected from the group consisting of: —$C(O)NH(CH_2)_2CH(OH)R^{W4}$, where $R^{W4}$ is $C_{7-19}$ alkyl; —$C(O)NH(CH_2)_2CH_2OR^{W3}$, where $R^{W3}$ is —$C(O)(CH_2)_{aa}CH_3$ and where aa is an integer of 6 to 18; and —$C(O)NH(CH_2)_2CH(OR^{W3})R^{W4}$, where $R^{W3}$ is —$C(O)(CH_2)_{aa}CH_3$ and $R^{W4}$ is $CH_2OC(O)(CH_2)_{bb}CH_3$, where each of aa and bb is, independently, an integer of 6 to 18.

In another embodiment of either the first or second aspect of the invention, U is $C(O)C(R^{U2})(R^{U3})NHR^{U4}$ or —$C(O)(CH_2)_fNHR^{U4}$, where f is an integer of 1 to 4, $R^{U2}$ is an optionally substituted $C_{1-6}$alkyl, $R^{U3}$ is H, and $R^{U4}$ is an optionally substituted $C_{6-10}$ aryl or an optionally substituted $C_{2-9}$ heterocyclyl. Examples include those compounds in which $R^{U4}$ is

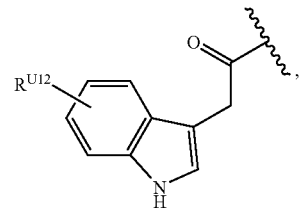

where $R^{U12}$ is optionally substituted $C_{6-10}$ aryl, optionally substituted $C_{6-10}$ aryloxy, optionally substituted $C_{7-16}$ aralkyl, optionally substituted $C_{7-16}$ aralkoxy, optionally substituted $C_{2-9}$ heterocyclyl, optionally substituted $C_{2-9}$ heterocyclyloxy, optionally substituted $C_{3-15}$ heterocyclylalkyl, or optionally substituted $C_{3-15}$ heterocyclylalkyloxy. Most preferably, $R^{U4}$ is selected from the group consisting of:

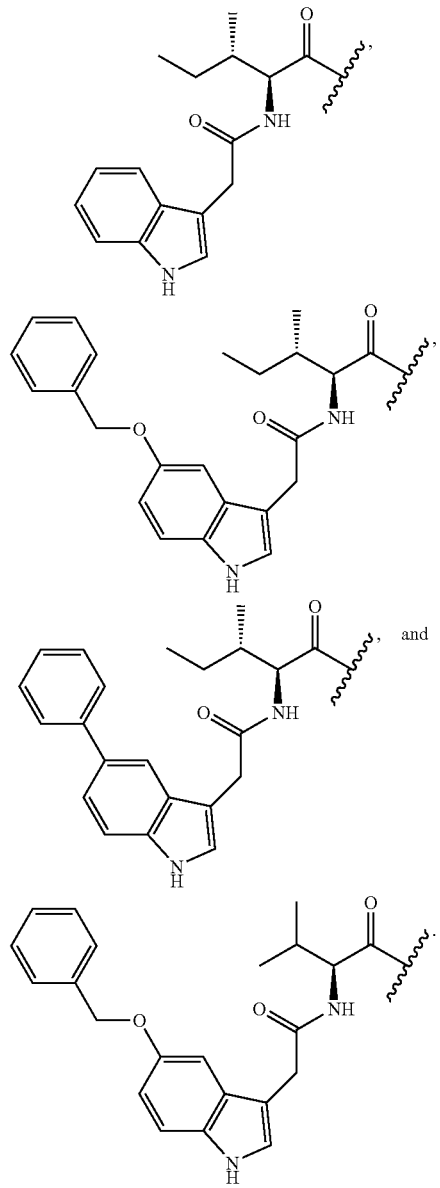

Other compounds of the invention include those selected from the group consisting of:
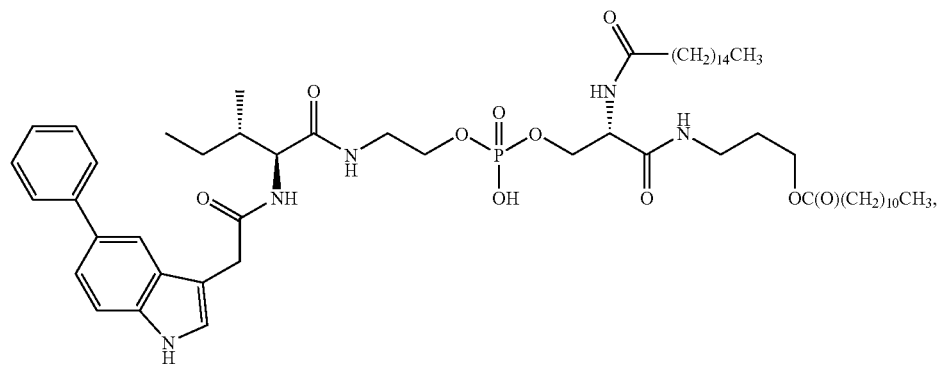
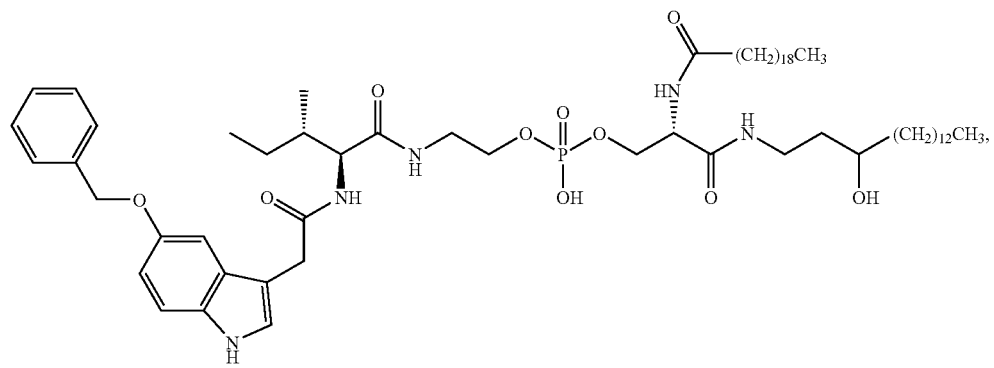
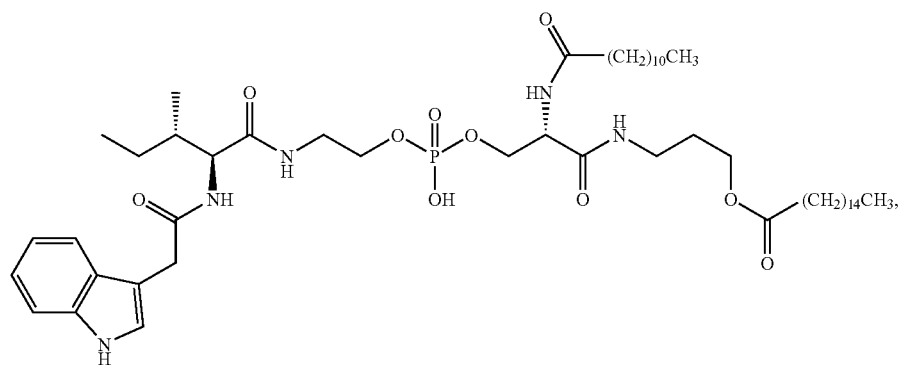
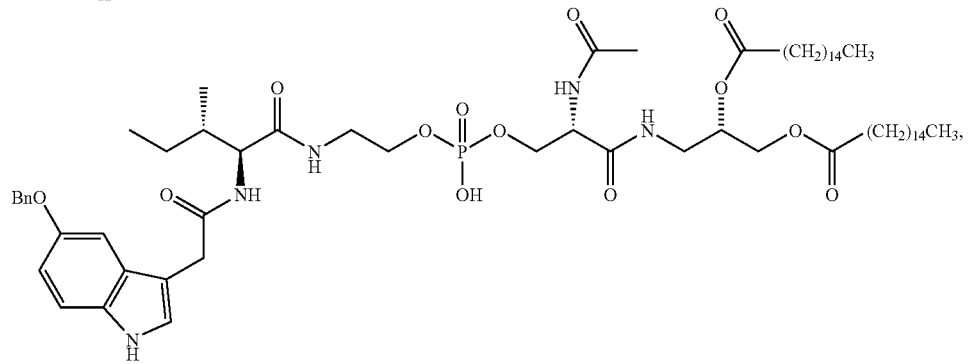

-continued
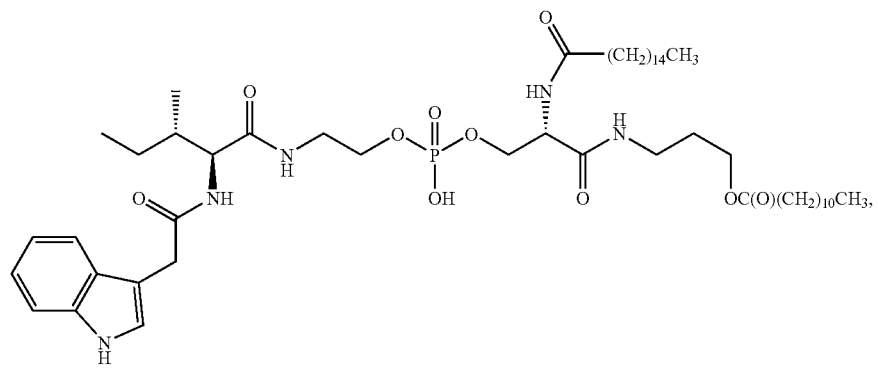
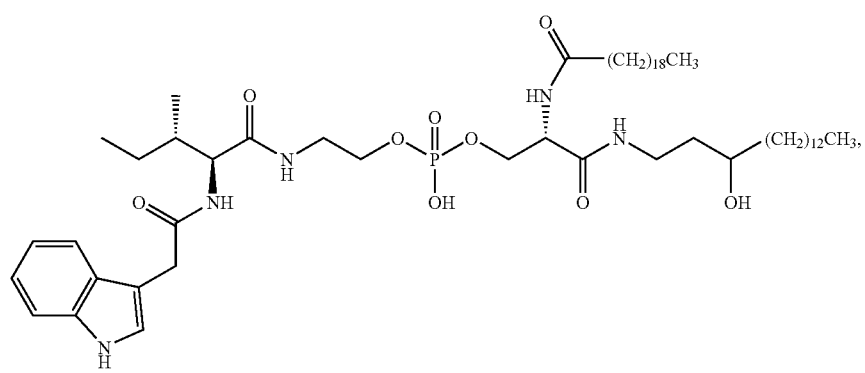
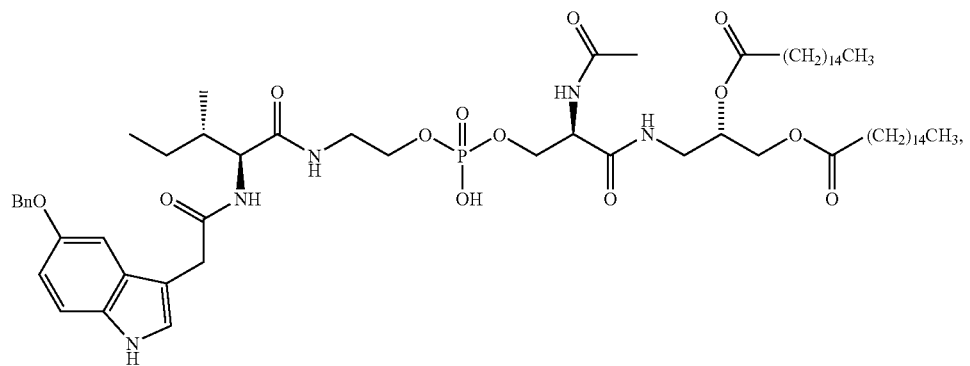
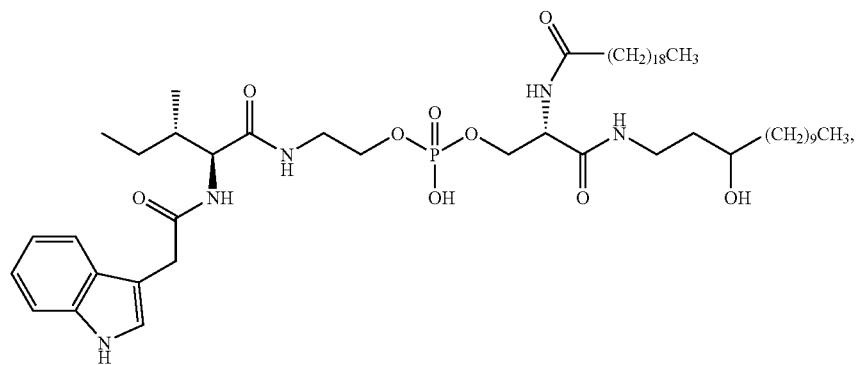

-continued
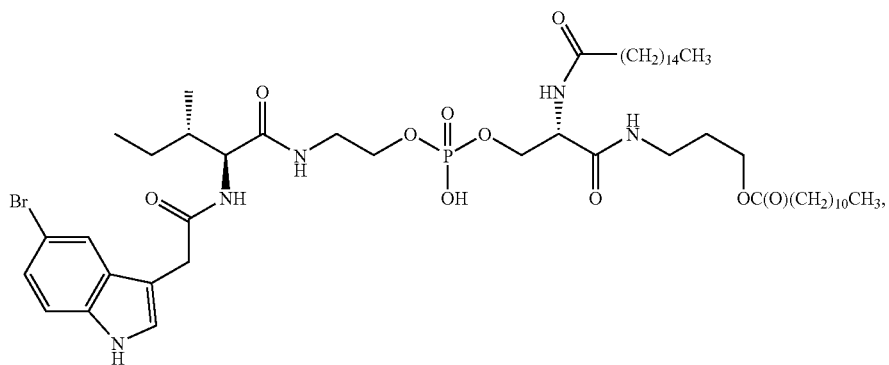
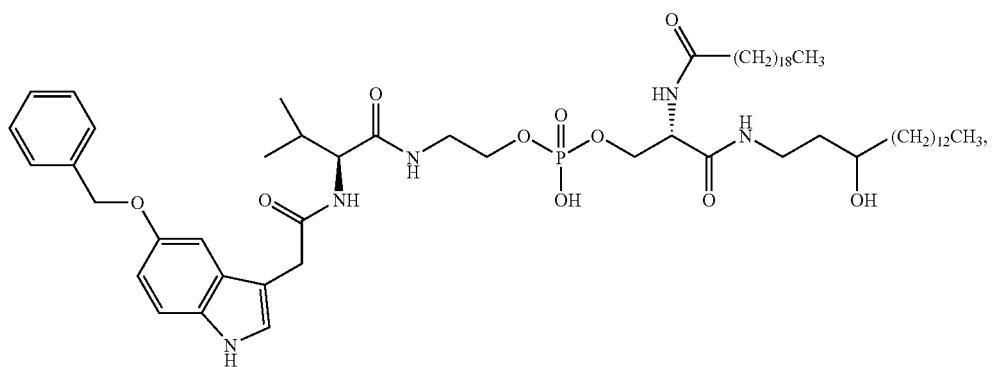
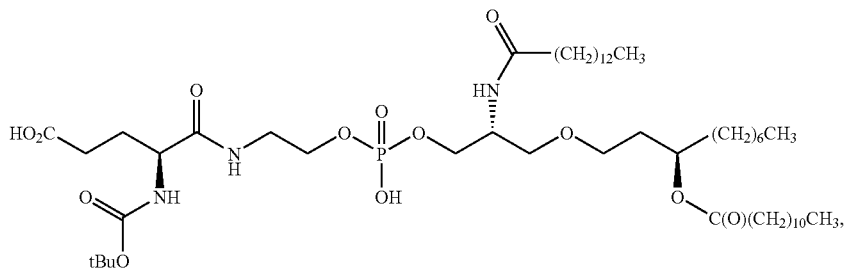
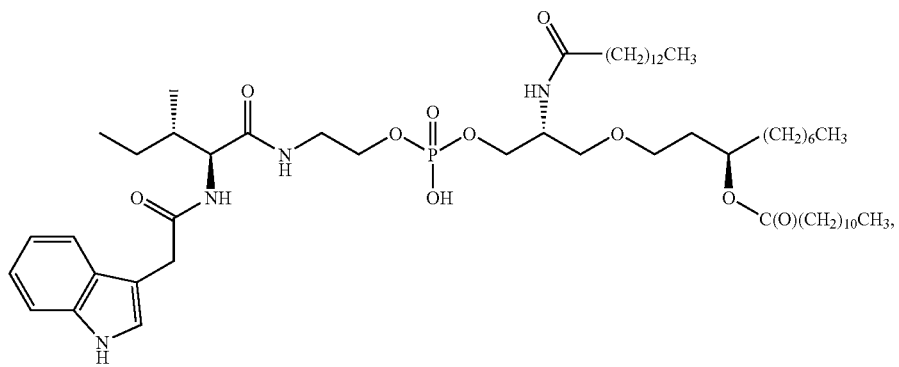

-continued
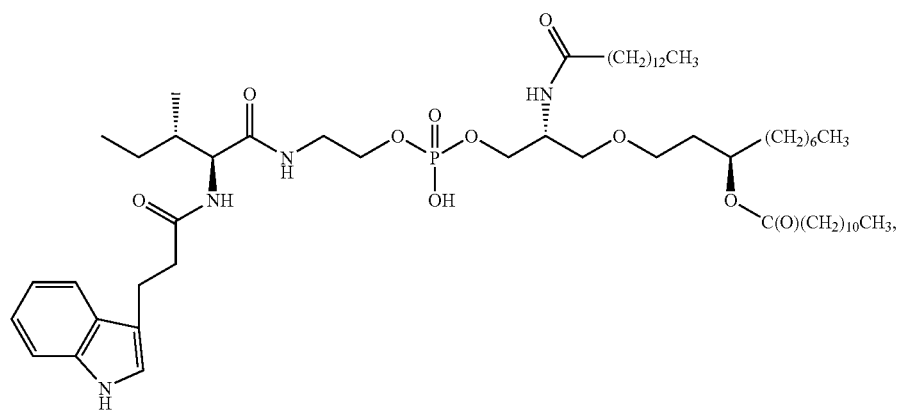
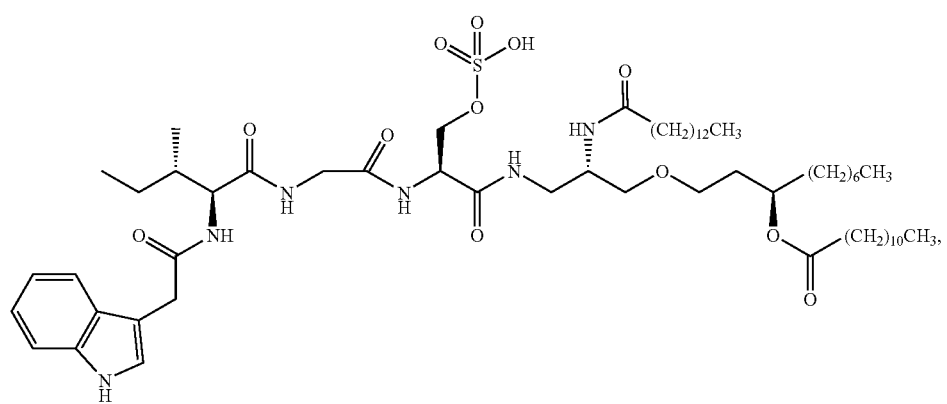
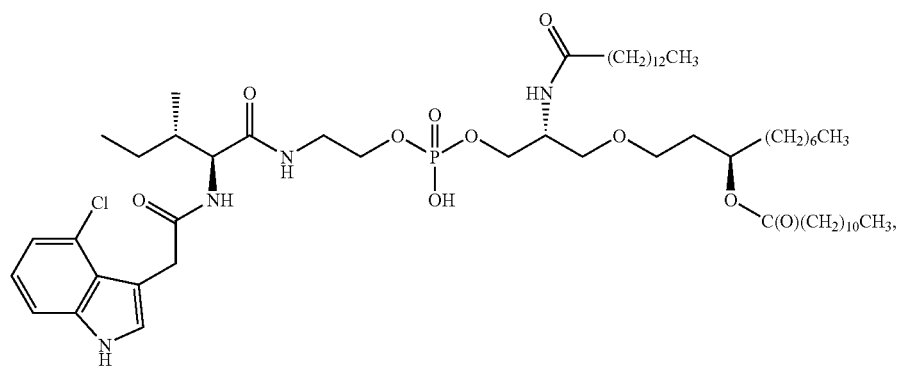
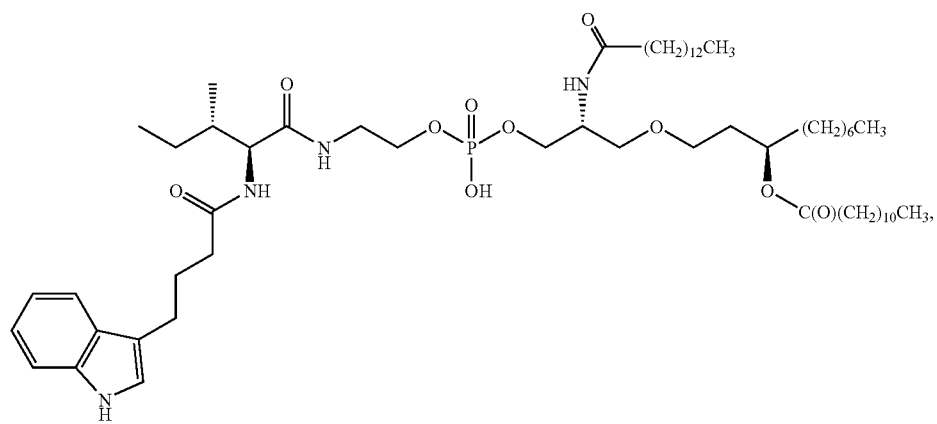

-continued
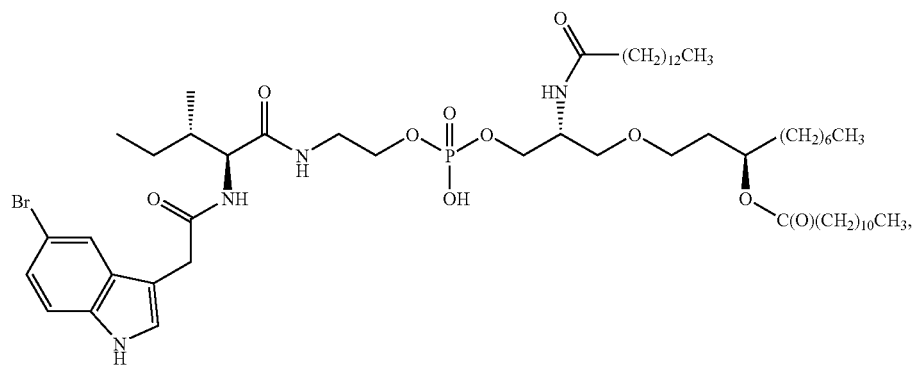
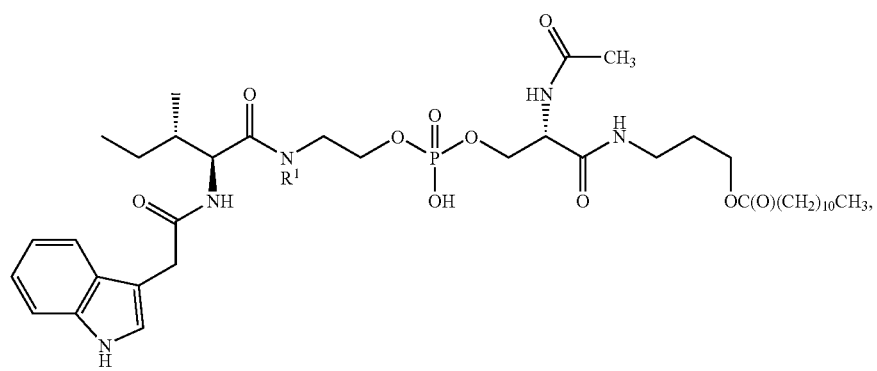
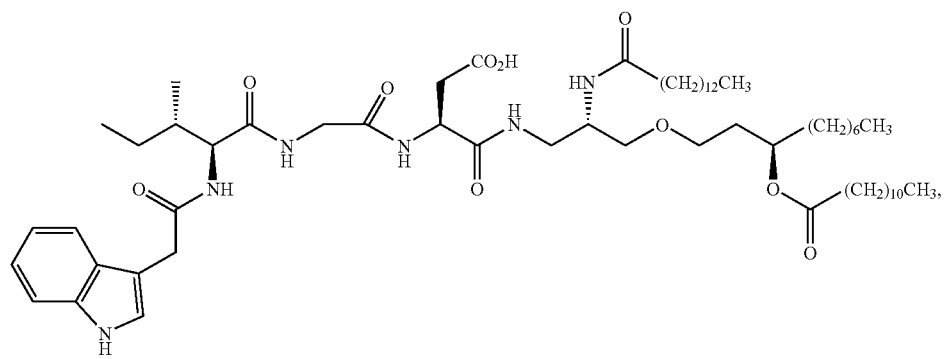
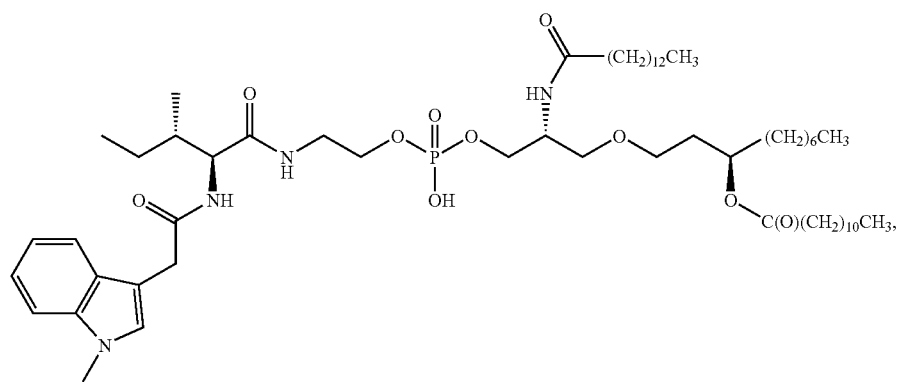

-continued

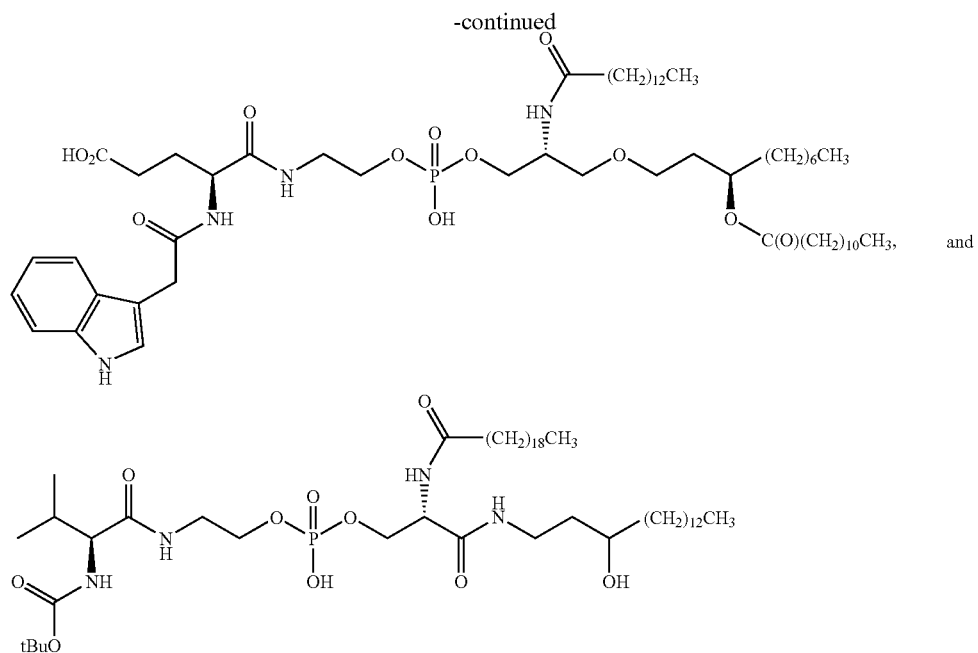

and

In a third aspect, the invention features a compound having the formula:

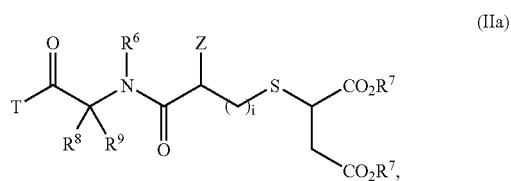

(IIa)

or a pharmaceutically acceptable salt or prodrug thereof, wherein i is an integer of 1 to 4

$R^6$ is H or $C_{1-6}$ alkyl;

Z is selected from the group consisting of —$NR^{Z1}V$, —$N(R^{Z1})C(O)V$, —$N(R^{Z1})C(S)V$, —$N(R^{Z1})C(O)N(R^{Z2})V$, —$N(R^{Z1})C(S)N(R^{Z2})V$, —$N(R^{Z1})C(O)OV$, and —$N(R^{Z1})S(O)_2V$, where each of $R^{Z1}$ and $R^{Z2}$ is, independently, H or $C_{1-4}$ alkyl, and V is a $C_{1-20}$ alkyl, $C_{1-20}$ alkenyl, or $C_{1-20}$ alkynyl group, optionally substituted with halo, hydroxyl, $C_{1-21}$ acyloxy, oxo, $C_{1-20}$ alkoxyl, or $C_{1-20}$ thioalkoxyl and optionally contains 1 to 2 phenyl or biphenyl moieties in and/or at the end of the carbon chain;

$R^7$ is $C_{1-20}$ alkyl, $C_{1-20}$ alkenyl, or $C_{1-20}$ alkynyl, optionally substituted with halo, hydroxyl, $C_{1-21}$ acyloxy, oxo, $C_{1-20}$ alkoxyl, or $C_{1-20}$ thioalkoxyl and optionally contains 1 to 2 phenyl or biphenyl moieties in and/or at the end of the carbon chain;

each of $R^8$ and $R^9$ is, independently, H, optionally substituted $C_{1-6}$ alkyl, optionally substituted $C_{7-16}$ aralkyl, or optionally substituted $C_{2-15}$ heterocyclylalkyl, or $R^8$ and $R^9$ together with the carbon atom they are bonded to form an optionally substituted $C_{3-4}$ aliphatic ring; and T is $OR^{T1}$, $NR^{T2}R^{T3}$, or a peptide chain of 1 to 10 natural or non-natural amino acids, or mixture thereof, linked via the N-terminal end and the C-terminal end is $CO_2R^{T1}$, or $CONR^{T2}R^{T3}$, wherein each of $R^{T1}$, $R^{T2}$, and $R^{T3}$ is selected from the group consisting of H, optionally substituted $C_{1-6}$ alkyl, optionally substituted $C_{2-6}$ alkenyl, optionally substituted $C_{2-6}$ alkynyl, optionally substituted $C_{7-16}$ aralkyl, optionally substituted $C_{2-15}$ heterocyclylalkyl, optionally substituted $C_{6-10}$ aryl, and optionally substituted $C_{1-9}$ heterocyclyl.

The invention also features a pharmaceutical composition that includes any of the compounds of the invention and a pharmaceutically acceptable excipient. The pharmaceutical compositions of the inventions can be used to treat or prevent a disease or condition characterized by Toll-like receptor 2 activation in a mammal, such as, for example, a human patient. Accordingly, the invention features a method for treating or preventing a disease in a mammal having, or predisposed to having, a condition characterized by Toll-like receptor 2 activation that includes administering a compound of formula I or formula II to the mammal in an amount sufficient to treat or prevent the disease or condition. The therapeutic methods of the invention can also involve administration of one or more compounds that is selective for TLR2 over, for example, TLR4, as well as methods involving administration of TLR2/TLR4 dual antagonists.

Examples of diseases or conditions characterized by TLR2 activation and that can be treated according to the invention include inflammatory bowel disease, sepsis, periodontal disease, mucositis, acne, cardiovascular disease, chronic obstructive pulmonary disease, arthritis, cystic fibrosis, bacterial-induced infections, viral-induced infections, mycoplasma-associated diseases, post-herpetic neuralgia, ischemia/reperfusion injury, asthma, stroke, brain injury, necrotizing enterocolitis, bed sores, leprosy, atopic dermatitis, psoriasis, trauma, allergy, neurodegenerative disease, amphotericin B-induced fever and nephritis, coronary artery bypass grafting, and atherosclerosis.

The invention also includes methods for identifying agents that decrease or inhibit activation of Toll-like receptor 2. These methods involve (i) contacting a cell expressing the receptor with a candidate agent in the presence of an activator of the receptor (in vitro or in vivo) and (ii) determining the effect of the agent on activation of the receptor. Detection of a decrease in activation of the receptor by the activator in the presence of the agent indicates the identification of agent that can be used to decrease or inhibit activation of the receptor. In these methods, the effect of the agent on the activation of the receptor can be determined by analysis of the expression of a reporter gene that is under the control of a promoter that is induced in a signaling pathway triggered by activation of the receptor.

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups are of 2 to 21 carbons.

The term "acyloxy" represents an alkyl group, as defined herein, attached to the parent molecular group through a carbonyl group and an oxygen atom. Exemplary acyloxy groups are of 2 to 21 carbons.

The term "alkenyl," as used herein, represents monovalent straight or branched chain groups of, unless otherwise specified, from 2 to 20 carbons containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to twenty carbon atoms; (2) alkylsulfinyl of one to twenty carbon atoms; (3) alkylsulfonyl of one to twenty carbon atoms; (4) amino; (5) aryl; (6) arylalkoxy, where the alkylene group is of one to twenty carbon atoms; (7) aryloyl; (8) azido; (9) carboxaldehyde; (10) cycloalkyl of three to eight carbon atoms; (11) halo; (12) heterocycle; (13) (heterocycle)oxy; (14) (heterocycle)oyl; (15) hydroxy; (16) N-protected amino; (17) nitro; (18) oxo; (19) spiroalkyl of three to eight carbon atoms; (20) thioalkoxy of one to twenty carbon atoms; (21) thiol; (22) —$CO_2R^A$, where $R^A$ is selected from the group consisting of (a) hydrogen, (b) substituted or unsubstituted $C_{1-20}$ alkyl, (c) substituted or unsubstituted $C_6$ or $C_{10}$ aryl, (d) substituted or unsubstituted $C_{7-16}$ arylalkyl, where the alkylene group is of one to twenty carbon atoms, (e) substituted or unsubstituted $C_{1-9}$ heterocyclyl, and (f) substituted or unsubstituted $C_{2-15}$ heterocyclylalkyl, where the alkylene group is of one to twenty carbon atoms; (23) —C(O)NR$^B$R$^C$, where each of R$^B$ and R$^C$ is, independently, selected from the group consisting of (a) hydrogen, (b) alkyl, (c) aryl, and (d) arylalkyl, where the alkylene group is of one to twenty carbon atoms; (24) —S(O)$_2$R$^D$, where R$^D$ is selected from the group consisting of (a) alkyl, (b) aryl, and (c) arylalkyl, where the alkylene group is of one to twenty carbon atoms; (25) —S(O)$_2$NR$^E$R$^F$, where each of R$^E$ and R$^F$ is, independently, selected from the group consisting of (a) hydrogen, (b) alkyl, (c) aryl, and (d) arylalkyl, where the alkylene group is of one to twenty carbon atoms; and (26) —NR$^G$R$^H$, where each of R$^G$ and R$^H$ is, independently, selected from the group consisting of (a) hydrogen, (b) an N-protecting group, (c) alkyl of one to twenty carbon atoms, (d) alkenyl of two to twenty carbon atoms, (e) alkynyl of two to twenty carbon atoms, (f) aryl, (g) arylalkyl, where the alkylene group is of one to twenty carbon atoms, (h) cycloalkyl of three to eight carbon atoms, and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The terms "alkoxy" or "alkyloxy," as used interchangeably herein, represent an alkyl group attached to the parent molecular group through an oxygen atom. Exemplary unsubstituted alkoxy groups are of 1 to 20 carbons.

The term "alkyl," as used herein, represents a monovalent group derived from a straight or branched chain saturated hydrocarbon of, unless otherwise specified, from 1 to 20 carbons and is exemplified by methyl, ethyl, n- and iso-propyl, n-, sec-, iso- and tert-butyl, neopentyl and the like and may be optionally substituted with one, two, three or, in the case of alkyl groups of two carbons or more, four substituents independently selected from the group consisting of: (1) alkoxy of one to twenty carbon atoms; (2) alkylsulfinyl of one to twenty carbon atoms; (3) alkylsulfonyl of one to twenty carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to twenty carbon atoms; (21) thiol; (22) —$CO_2R^A$, where $R^A$ is selected from the group consisting of (a) hydrogen, (b) substituted or unsubstituted $C_{1-20}$ alkyl, (c) substituted or unsubstituted $C_6$ or $C_{10}$ aryl, (d) substituted or unsubstituted $C_{7-16}$ arylalkyl, where the alkylene group is of one to twenty carbon atoms, (e) substituted or unsubstituted $C_{1-9}$ heterocyclyl, and (f) substituted or unsubstituted $C_{2-15}$ heterocyclylalkyl, where the alkylene group is of one to twenty carbon atoms; (23) —C(O)NR$^B$R$^C$, where each of R$^B$ and R$^C$ is, independently, selected from the group consisting of (a) hydrogen, (b) alkyl, (c) aryl, and (d) arylalkyl, where the alkylene group is of one to twenty carbon atoms; (24) —S(O)$_2$R$^D$, where R$^D$ is selected from the group consisting of (a) alkyl, (b) aryl, and (c) arylalkyl, where the alkylene group is of one to twenty carbon atoms; (25) —S(O)$_2$NR$^E$R$^F$, where each of R$^E$ and R$^F$ is, independently, selected from the group consisting of (a) hydrogen, (b) alkyl, (c) aryl, and (d) arylalkyl, where the alkylene group is of one to twenty carbon atoms; and (26) —NR$^G$R$^H$, where each of R$^G$ and R$^H$ is, independently, selected from the group consisting of (a) hydrogen, (b) an N-protecting group, (c) alkyl of one to twenty carbon atoms, (d) alkenyl of two to twenty carbon atoms, (e) alkynyl of two to twenty carbon atoms, (f) aryl, (g) arylalkyl, where the alkylene group is of one to twenty carbon atoms, (h) cycloalkyl of three to eight carbon atoms, and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like.

The term "alkylthio," as used herein, represents an alkyl group attached to the parent molecular group through a sulfur atom. Exemplary unsubstituted alkylthio groups are of 1 to 20 carbons.

The term "alkynyl," as used herein, represents monovalent straight or branched chain groups of 2 to 20 carbon atoms containing a carbon-carbon triple bond and is exemplified by ethynyl, 1-propynyl, and the like and may be optionally substituted with one, two, three or four substituents independently selected from the group consisting of: (1) alkoxy of one to twenty carbon atoms; (2) alkylsulfinyl of one to twenty carbon atoms; (3) alkylsulfonyl of one to twenty carbon atoms; (4) amino; (5) aryl; (6) arylalkoxy, where the alkylene group is of one to twenty carbon atoms; (7) aryloyl; (8) azido; (9) carboxaldehyde; (10) cycloalkyl of three to eight carbon atoms; (11) halo; (12) heterocycle; (13) (heterocycle)oxy; (14) (heterocycle)oyl; (15) hydroxy; (16) N-protected amino; (17) nitro; (18) oxo; (19) spiroalkyl of three to eight carbon atoms; (20) thioalkoxy of one to twenty carbon atoms; (21) thiol; (22) —$CO_2R^A$, where $R^A$ is selected from the group consisting of (a) alkyl, (b) aryl and (c) arylalkyl, where the alkylene group is of one to twenty carbon atoms; (23) —C(O)N$R^BR^C$, where each of $R^B$ and $R^C$ is, independently, selected from the group consisting of (a) hydrogen, (b) alkyl, (c) aryl, and (d) arylalkyl, where the alkylene group is of one to twenty carbon atoms; (24) —$S(O)_2R^D$, where $R^D$ is selected from the group consisting of (a) alkyl, (b) aryl, and (c) arylalkyl, where the alkylene group is of one to twenty carbon atoms; (25) —$S(O)_2NR^ER^F$, where each of $R^E$ and $R^F$ is, independently, selected from the group consisting of (a) hydrogen, (b) alkyl, (c) aryl, and (d) arylalkyl, where the alkylene group is of one to twenty carbon atoms; and (26) —$NR^GR^H$, where each of $R^G$ and $R^H$ is, independently, selected from the group consisting of (a) hydrogen, (b) an N-protecting group, (c) alkyl of one to twenty carbon atoms, (d) alkenyl of two to twenty carbon atoms, (e) alkynyl of two to twenty carbon atoms, (f) aryl, (g) arylalkyl, where the alkylene group is of one to twenty carbon atoms, (h) cycloalkyl of three to eight carbon atoms, and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The term "alpha-amino acid residue," as used herein, represents a —N($R^A$)C($R^B$)($R^C$)C(O)— linkage, where $R^A$ is selected from the group consisting of (a) hydrogen, (b) alkyl, (c) aryl, and (d) arylalkyl, as defined herein; and each of $R^B$ and $R^C$ is, independently, selected from the group consisting of: (a) hydrogen, (b) optionally substituted alkyl, (c) optionally substituted cycloalkyl, (d) optionally substituted aryl, (e) optionally substituted arylalkyl, (f) optionally substituted heterocyclyl, and (g) optionally substituted heterocyclylalkyl, each of which is as defined herein. For natural amino acids, $R^B$ is H and $R^C$ corresponds to those side chains of natural amino acids found in nature, or their antipodal configurations. Exemplary natural amino acids include alanine, cysteine, aspartic acid, glutamic acid, phenylalanine, glycine, histidine, isoleucine, lysine, leucine, methionine, aspartamine, ornithine, proline, glutamine, arginine, serine, threonine, valine, tryptophan, and tyrosine, each of which, except glycine, as their D- or L-form. As used herein, for the most part, the names of naturally-occurring amino acids and aminoacyl residues used herein follow the naming conventions suggested by the IUPAC Commission on the Nomenclature of Organic Chemistry and the IUPAC-IUB Commission on Biochemical Nomenclature as set out in Nomenclature of α-Amino Acids (Recommendations, 1974), *Biochemistry* 14 (2), 1975. The present invention also contemplates non-naturally occurring (i.e., non-natural) amino acid residues in their D- or L-form such as, for example, homophenylalanine, phenylglycine, cyclohexylglycine, cyclohexylalanine, cyclopentyl alanine, cyclobutylalanine, cyclopropylalanine, cyclohexylglycine, norvaline, norleucine, thiazoylalanine (2-, 4-, and 5-substituted), pyridylalanine (2-, 3-, and 4-isomers), naphthalalanine (1- and 2-isomers) and the like. Non-natural amino acids also include beta-amino acids, optionally substituted at the alpha or beta or both alpha and beta positions, independently, with $R^A$ and $R^B$, as described above.

The term "amino," as used herein, represents an —$NH_2$ group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four, or five substituents independently selected from the group consisting of: (1) alkanoyl of one to twenty carbon atoms; (2) alkyl of one to twenty carbon atoms; (3) alkoxy of one to twenty carbon atoms; (4) alkoxyalkyl, where the alkyl and alkylene groups are independently of one to twenty carbon atoms; (5) alkylsulfinyl of one to twenty carbon atoms; (6) alkylsulfinylalkyl, where the alkyl and alkylene groups are independently of one to twenty carbon atoms; (7) alkylsulfonyl of one to twenty carbon atoms; (8) alkylsulfonylalkyl, where the alkyl and alkylene groups are independently of one to twenty carbon atoms; (9) aryl; (10) arylalkyl, where the alkyl group is of one to twenty carbon atoms; (11) amino; (12) aminoalkyl of one to twenty carbon atoms; (13) aryl; (14) arylalkyl, where the alkylene group is of one to twenty carbon atoms; (15) aryloyl; (16) azido; (17) azidoalkyl of one to twenty carbon atoms; (18) carboxaldehyde; (19) (carboxaldehyde)alkyl, where the alkylene group is of one to twenty carbon atoms; (20) cycloalkyl of three to eight carbon atoms; (21) cycloalkylalkyl, where the cycloalkyl group is of three to eight carbon atoms and the alkylene group is of one to ten carbon atoms; (22) halo; (23) haloalkyl of one to twenty carbon atoms; (24) heterocyclyl; (25) (heterocyclyl)oxy; (26) (heterocyclyl)oyl; (27) hydroxy; (28) hydroxyalkyl of one to twenty carbon atoms; (29) nitro; (30) nitroalkyl of one to twenty carbon atoms; (31) N-protected amino; (32) N-protected aminoalkyl, where the alkylene group is of one to twenty carbon atoms; (33) oxo; (34) thioalkoxy of one to twenty carbon atoms; (35) thioalkoxyalkyl, where the alkyl and alkylene groups are independently of one to twenty carbon atoms; (36) —$(CH_2)_qCO_2R^A$, where q is an integer of zero to four and $R^A$ is selected from the group consisting of (a) alkyl, (b) aryl, and (c) arylalkyl, where the alkylene group is of one to twenty carbon atoms; (37) —$(CH_2)_qCONR^BR^C$, where $R^B$ and $R^C$ are independently selected from the group consisting of (a) hydrogen, (b) alkyl, (c) aryl, and (d) arylalkyl, where the alkylene group is of one to twenty carbon atoms; (38) —$(CH_2)_qS(O)_2R^D$, where $R^D$ is selected from the group consisting of (a) alkyl, (b) aryl, and (c) arylalkyl, where the alkylene group is of one to twenty carbon atoms; (39) —$(CH_2)_qS(O)_2NR^ER^F$, where each of $R^E$ and $R^F$ is, independently, selected from the group consisting of (a) hydrogen, (b) alkyl, (c) aryl, and (d) arylalkyl, where the alkylene group is of one to twenty carbon atoms; (40) —$(CH_2)_qNR^GR^H$, where each of $R^G$ and $R^H$ is, independently, selected from the group consisting of (a) hydrogen, (b) an N-protecting group, (c) alkyl of one to twenty carbon atoms, (d) alkenyl of two to twenty carbon atoms, (e) alkynyl of two to twenty carbon atoms, (f) aryl, (g) arylalkyl, where the alkylene group is of one to twenty carbon atoms, (h) cycloalkyl of three to eight carbon atoms, and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "arylalkyl" or "aralkyl," as used interchangeably herein, represent an aryl group attached to the parent molecular group through an alkyl group. Exemplary unsubstituted arylalkyl groups are of 7 to 16 carbons.

The term "aryloxy," as used herein, represents an aryl group that is attached to the parent molecular group through an oxygen atom. Exemplary unsubstituted aryloxy groups are of 6 or 10 carbons.

The terms "aryloyl" or "aroyl," as used interchangeably herein, represent an aryl group that is attached to the parent molecular group through a carbonyl group. Exemplary unsubstituted aryloxycarbonyl groups are of 7 or 11 carbons.

The term "carbonyl" as used herein, represents a C=O group.

The term "carboxy" or "carboxyl," as used interchangeably herein, represents a —CO$_2$H group.

The terms "carboxy protecting group" or "carboxyl protecting group," as used herein, represent those groups intended to protect a —CO$_2$H group against undesirable reactions during synthetic procedures. Commonly used carboxy-protecting groups are disclosed in Greene, "Protective Groups In Organic Synthesis, 3rd Edition" (John Wiley & Sons, New York, 1999), which is incorporated herein by reference.

The phrase "compound selective for antagonism of Toll-like receptor 2 over Toll-like receptor 4" is used to describe those compounds that have an IC$_{50}$ value when tested by the TLR2 in vitro assay described herein that is less than the IC$_{50}$ value obtained when the compound is tested by the TLR4 in vitro assay described herein.

The term "cycloalkyl," as used herein, represents a monovalent saturated or unsaturated non-aromatic cyclic hydrocarbon group of three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to twenty carbon atoms; (2) alkyl of one to twenty carbon atoms; (3) alkoxy of one to twenty carbon atoms; (4) alkoxyalkyl, where the alkyl and alkylene groups are independently of one to twenty carbon atoms; (5) alkylsulfinyl of one to twenty carbon atoms; (6) alkylsulfinylalkyl, where the alkyl and alkylene groups are independently of one to twenty carbon atoms; (7) alkylsulfonyl of one to twenty carbon atoms; (8) alkylsulfonylalkyl, where the alkyl and alkylene groups are independently of one to twenty carbon atoms; (9) aryl; (10) arylalkyl, where the alkyl group is of one to twenty carbon atoms; (11) amino; (12) aminoalkyl of one to twenty carbon atoms; (13) aryl; (14) arylalkyl, where the alkylene group is of one to twenty carbon atoms; (15) aryloyl; (16) azido; (17) azidoalkyl of one to twenty carbon atoms; (18) carboxaldehyde; (19) (carboxaldehyde)alkyl, where the alkylene group is of one to twenty carbon atoms; (20) cycloalkyl of three to eight carbon atoms; (21) cycloalkylalkyl, where the cycloalkyl group is of three to eight carbon atoms and the alkylene group is of one to ten carbon atoms; (22) halo; (23) haloalkyl of one to twenty carbon atoms; (24) heterocyclyl; (25) (heterocyclyl)oxy; (26) (heterocyclyl)oyl; (27) hydroxy; (28) hydroxyalkyl of one to twenty carbon atoms; (29) nitro; (30) nitroalkyl of one to twenty carbon atoms; (31) N-protected amino; (32) N-protected aminoalkyl, where the alkylene group is of one to twenty carbon atoms; (33) oxo; (34) thioalkoxy of one to twenty carbon atoms; (35) thioalkoxyalkyl, where the alkyl and alkylene groups are independently of one to twenty carbon atoms; (36) —(CH$_2$)$_q$CO$_2$R$^A$, where q is an integer of zero to four and R$^A$ is selected from the group consisting of (a) alkyl, (b) aryl, and (c) arylalkyl, where the alkylene group is of one to twenty carbon atoms; (37) —(CH$_2$)$_q$CONR$^B$R$^C$, where each of R$^B$ and R$^C$ is, independently, selected from the group consisting of (a) hydrogen, (b) alkyl, (c) aryl, and (d) arylalkyl, where the alkylene group is of one to twenty carbon atoms; (38) —(CH$_2$)$_q$S(O)$_2$R$^D$, where R$^D$ is selected from the group consisting of (a) alkyl, (b) aryl, and (c) arylalkyl, where the alkylene group is of one to twenty carbon atoms; (39) —(CH$_2$)$_q$S(O)$_2$NR$^E$R$^F$, where each of R$^E$ and R$^F$ is, independently, selected from the group consisting of (a) hydrogen, (b) alkyl, (c) aryl, and (d) arylalkyl, where the alkylene group is of one to twenty carbon atoms; (40) —(CH$_2$)$_q$NR$^G$R$^H$, where each of R$^G$ and R$^H$ is, independently, selected from the group consisting of (a) hydrogen; (b) an N-protecting group; (c) alkyl of one to twenty carbon atoms; (d) alkenyl of two to twenty carbon atoms; (e) alkynyl of two to twenty carbon atoms; (f) aryl; (g) arylalkyl, where the alkylene group is of one to twenty carbon atoms; (h) cycloalkyl of three to eight carbon atoms and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo," as used interchangeably herein, represents F, Cl, Br, and I.

The term "heteroaryl," as used herein, represents that subset of heterocycles, as defined herein, which are aromatic: i.e., they contain 4n+2 pi electrons within the mono- or multicyclic ring system. Exemplary unsubstituted heteroaryl groups are of 1 to 9 carbons.

The terms "heterocycle" or "heterocyclyl," as used interchangeably herein, represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic, and tetracyclic groups in which any of the above heterocyclic rings is fused to one or two rings independently selected from the group consisting of an aryl ring, a cyclohexane ring, a cyclohexene ring, a cyclopentane ring, a cyclopentene ring, and another monocyclic heterocyclic ring such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl, and the like. Heterocyclic groups also include compounds of the formula

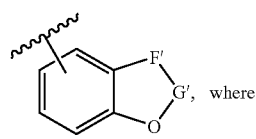

F' is selected from the group consisting of —CH$_2$—, —CH$_2$O—, and —O—, and G' is selected from the group consisting of —C(O)— and —(C(R')(R"))$_v$—, where each of R' and R" is, independently, selected from the group consisting of hydrogen or alkyl of one to four carbon atoms, and v is one to three and includes groups such as 1,3-benzodioxolyl, 1,4-benzodioxanyl and the like. Any of the heterocycle groups mentioned herein may be optionally substituted with one, two, three, four, or five substituents independently selected from the group consisting of: (1) alkanoyl of one to twenty carbon atoms; (2) alkyl of one to twenty carbon atoms; (3) alkoxy of one to twenty carbon atoms; (4) alkoxyalkyl, where the alkyl and alkylene groups are independently of one to twenty carbon atoms; (5) alkylsulfinyl of one to twenty carbon atoms; (6) alkylsulfinylalkyl, where the alkyl and alkylene groups are independently of one to twenty carbon atoms; (7) alkylsulfonyl of one to twenty carbon atoms; (8) alkylsulfonylalkyl, where the alkyl and alkylene groups are independently of one to twenty carbon atoms; (9) aryl; (10) arylalkyl, where the alkyl group is of one to twenty carbon atoms; (11) amino; (12) aminoalkyl of one to twenty carbon atoms; (13) aryl; (14) arylalkyl, where the alkylene group is of one to twenty carbon atoms; (15) aryloyl; (16) azido; (17) azidoalkyl of one to twenty carbon atoms; (18) carboxaldehyde; (19) (carboxaldehyde)alkyl, where the alkylene group is of one to twenty carbon atoms; (20) cycloalkyl of three to eight carbon atoms; (21) cycloalkylalkyl, where the cycloalkyl group is of three to eight carbon atoms and the alkylene group is of one to ten carbon atoms; (22) halo; (23) haloalkyl of one to twenty carbon atoms; (24) heterocycle; (25) (heterocycle)oxy; (26) (heterocycle)oyl; (27) hydroxy; (28) hydroxyalkyl of one to twenty carbon atoms; (29) nitro; (30) nitroalkyl of one to twenty carbon atoms; (31) N-protected amino; (32) N-protected aminoalkyl, where the alkylene group is of one to twenty carbon atoms; (33) oxo; (34) thioalkoxy of one to twenty carbon atoms; (35) thioalkoxyalkyl, where the alkyl and alkylene groups are independently of one to twenty carbon atoms; (36) —(CH$_2$)$_q$CO$_2$R$^A$, where q is an integer of zero to four and R$^A$ is selected from the group consisting of (a) alkyl, (b) aryl, and (c) arylalkyl, where the alkylene group is of one to twenty carbon atoms; (37) —(CH$_2$)$_q$CONR$^B$R$^C$, where each of R$^B$ and R$^C$ is, independently, selected from the group consisting of (a) hydrogen, (b) alkyl, (c) aryl, and (d) arylalkyl, where the alkylene group is of one to twenty carbon atoms; (38) —(CH$_2$)$_q$S(O)$_2$R$^D$, where R$^D$ is selected from the group consisting of (a) alkyl, (b) aryl, and (c) arylalkyl, where the alkylene group is of one to twenty carbon atoms; (39) —(CH$_2$)$_q$S(O)$_2$NR$^E$R$^F$, where each of R$^E$ and R$^F$ is, independently, selected from the group consisting of (a) hydrogen, (b) alkyl, (c) aryl, and (d) arylalkyl, where the alkylene group is of one to twenty carbon atoms; (40) —(CH$_2$)$_q$NR$^G$R$^H$, where each of R$^G$ and R$^H$ is, independently, selected from the group consisting of (a) hydrogen; (b) an N-protecting group; (c) alkyl of one to twenty carbon atoms; (d) alkenyl of two to twenty carbon atoms; (e) alkynyl of two to twenty carbon atoms; (f) aryl; (g) arylalkyl, where the alkylene group is of one to twenty carbon atoms; (h) cycloalkyl of three to eight carbon atoms and (i) cycloalkylalkyl, where the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "heterocyclyloxy," as used herein, represents a hetercyclyl group which is attached to the parent molecular group through an oxygen atom.

The term "hydroxy" or "hydroxyl," as used interchangeably herein, represents an —OH group.

The term "N-protected amino," as used herein, refers to an amino group, as defined herein, to which is attached an N-protecting or nitrogen-protecting group, as defined herein.

The terms "N-protecting group," "nitrogen protecting group," or "amino protecting group," as used herein, represent those groups intended to protect an amino group against undesirable reactions during synthetic procedures. Commonly used N-protecting groups are disclosed in Greene, "Protective Groups In Organic Synthesis, 3d Edition" (John Wiley & Sons, New York, 1999), which is incorporated herein by reference. N-protecting groups comprise acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected L- or D-amino acids such as alanine, leucine, phenylalanine, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "non-vicinal oxygen atoms" refers to oxygen atoms that are not bonded to the same carbon atom.

The term "pharmaceutically acceptable salt," as use herein, refers to those salts which are, within the scope of sound medical judgement, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences* 66:1-19, 1977. The salts can be prepared in situ during the final isolation and purification of a compound of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The term "pharmaceutically acceptable ester," as used herein, represents esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl group preferably has not more than 6 carbon atoms. Examples of particular esters include formates, acetates, propionates, butyates, acrylates, and ethylsuccinates.

The term "pharmaceutically acceptable prodrugs," as used herein, means prodrugs of the compounds of the present invention which are, within the scope of sound medical judgement, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "phenyl" means an aromatic ring containing 6 carbons. Phenyl rings can be optionally substituted. When a phenyl ring is in a carbon chain it is part of the carbon chain linkage (i.e., the phenyl ring is bonded to the chain at two positions in either an ortho, meta, or para fashion). When a phenyl ring is at the end of a carbon chain, it is bonded to the end of the carbon chain.

The term "prodrug," as used herein, represents compounds that are transformed in vivo into a parent compound of the above formula, for example, by hydrolysis in blood. A thorough discussion of prodrugs is provided in T. Higuchi and V. Stella, "Pro-drugs as Novel Delivery Systems," Vol. 14 of the A.C.S. Symposium Series, Edward B. Roche, ed., "Bioreversible Carriers in Drug Design," American Pharmaceutical Association and Pergamon Press, 1987, and Judkins et al., *Synthetic Communications* 26(23):4351-4367, 1996, each of which is incorporated herein by reference.

The term "sulfonyl," as used herein, represents —S(O)$_2$—.
By "thiol" is meant an —SH group.

Asymmetric or chiral centers may exist in the compounds of the present invention. The present invention includes the various stereoisomers and mixtures thereof. Individual stereoisomers of compounds or the present invention may be prepared synthetically from commercially available starting materials that contain asymmetric or chiral centers or by preparation of mixtures of enantiometic compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary, or (2) direct separation of the mixture of optical enantiomers on chiral chromatographic columns. Enantiomers are designated herein by the symbols "R" or "S," depending on the configuration of substituents around the chiral carbon atom, or are drawn by conventional means with a bolded line defining a substituent above the plane of the page in three-dimensional space and a hashed or dashed line defining a substituent beneath the plane of the printed page in three-dimensional space. If no stereochemical designation is made, it is to be assumed that the structure definition includes both stereochemical possibilities.

The invention provides several advantages. For example, as is noted above, the invention provides an approach for treating inflammatory bowel disease, which can be a very painful and debilitating condition that is difficult to treat, and affects more than one million people in the United States alone. The methods of the invention can also be used to prevent or to treat other conditions associated with TLR2 activation, as is discussed elsewhere herein. Finally, the screening methods of the invention provide straightforward approaches for identifying and characterizing agents that can be used in the prevention and treatment of TLR2-associated diseases and conditions.

Other features and advantages of the invention will be apparent from the following detailed description and the claims.

DETAILED DESCRIPTION

The invention is based in part on our discovery that animals that do not express Toll-like receptor 2 (TLR2) are protected from dextran sulfate sodium (DSS) induction of colitis, a model for inflammatory bowel disease (IBD). Based on this discovery, we concluded that agents that block activation of TLR2 can be used to treat or to prevent colitis and related diseases or conditions, as well as other diseases or conditions characterized by activation of TLR2. Accordingly, the invention provides compounds and methods for preventing or treating diseases or conditions associated with activation of TLR2, as well as methods for identifying agents that decrease or inhibit activation of this receptor. The compounds and methods of the invention are described in further detail, as follows.

Preparation of TLR2 Inhibitors
A compound of formula I,

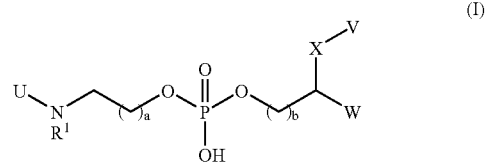

where X is —NHC(O)—; each of a and b is 1; W is —C(O)N(R$^{W1}$)(CH$_2$)$_c$CH(OR$^{W3}$)R$^{W4}$, where c is 2, each of R$^{W1}$ and R$^{W4}$ is H, and each of U, V, and R$^{W5}$ is as defined above can be prepared by a sequence of reactions shown in Scheme 1. Accordingly, a compound of formula III is epoxidized to produce a compound of formula IV, and the epoxy group reacted with a cyano group, which nucleophilically opens up the epoxide to produce a compound of formula V. Methods of preparing chiral epoxides from achiral starting materials are known to those skilled in the art and such methods would produce a compound of formula V of known configuration. Protection of the hydroxyl group as the t-butyldiphenylsilyl ether, followed by reduction of the cyano group with Raney nickel, produces a compound of formula VII. Compounds of formula VIII can be prepared by coupling a compound of formula VII with the L- or D-form of N-Fmoc-serine. The hydroxyl group derived from the serine can be subsequently reacted with phosphorylating agent IX, and the intermediate phoshine oxidized with hydrogen peroxide to produce a compound of formula X. The Fmoc protecting group can be selectively removed with piperidine and the resulting amine acylated with an acyl chloride or coupled to a compound containing a carboxyl group in a reaction mediated by a carbodiimide or other suitable coupling reagent. Subsequent removal of the silyl protecting group with fluoride ion produces a compound of formula XI. Removal of the Boc protecting group under acidic conditions (e.g., TFA or HCl/dioxane) and acylation, reductive amination, or sulfonation of the resulting amine results in a compound of formula XII. Treatment with a Pd(0) catalyst removes the phosphonate allyl protecting group to produce a compound of formula XIII.

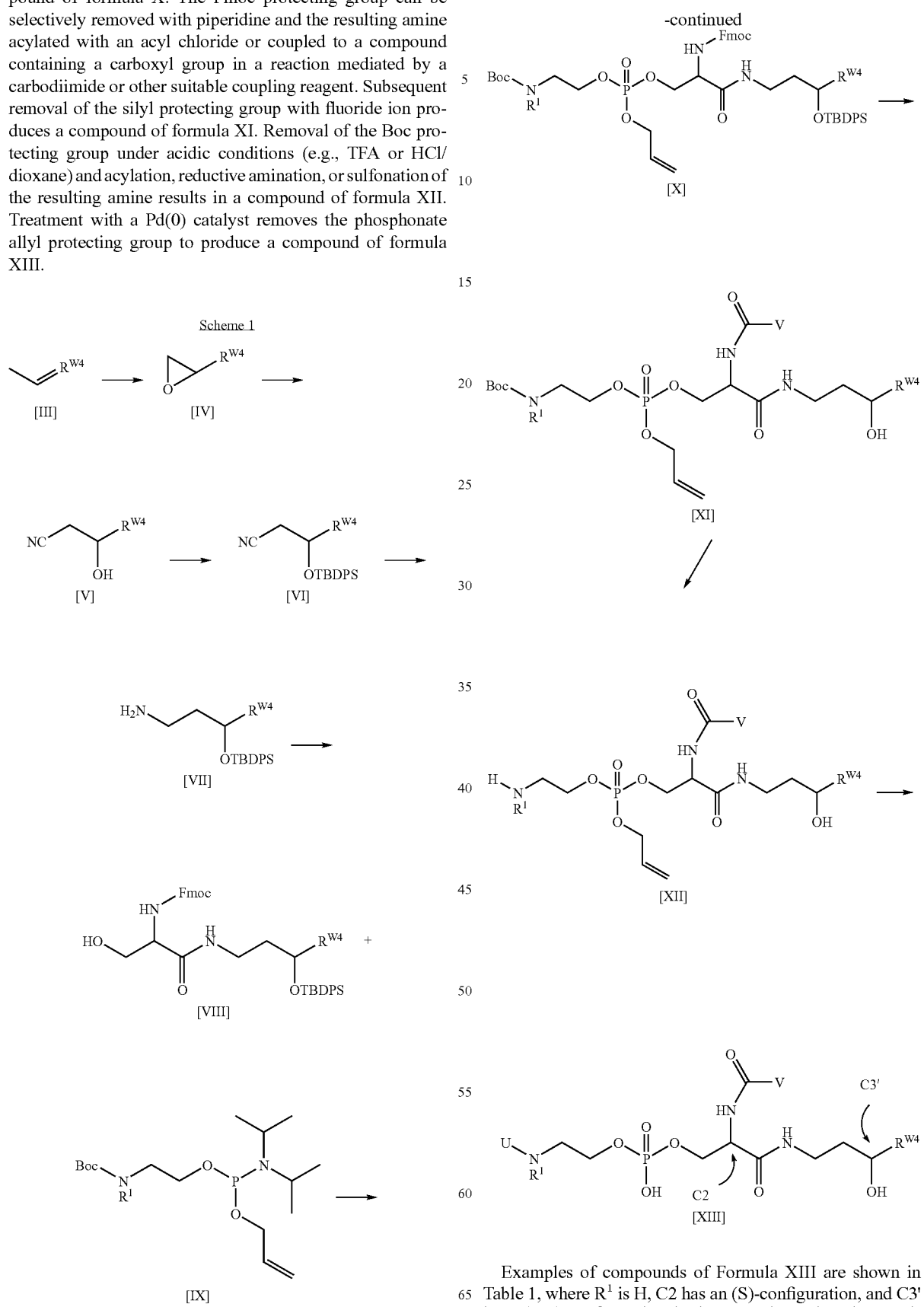

Examples of compounds of Formula XIII are shown in Table 1, where $R^1$ is H, C2 has an (S)-configuration, and C3' is an (R,S)-configurational mixture, unless otherwise specified.

TABLE 1

Compounds of formula XIII, where $R^1$ is H

| Compound No. | U | V | $R^{W4}$ |
|---|---|---|---|
| ER810702 | (tryptophan-acetamide-isoleucine structure) | $-(CH_2)_{18}CH_3$ | $-(CH_2)_6CH_3$ (R)-config. |
| ER811133 | (tryptophan-acetamide-isoleucine structure) | $-(CH_2)_{10}CH_3$ | $-(CH_2)_{12}CH_3$ |
| ER811134 | (tryptophan-acetamide-isoleucine structure) | $-(CH_2)_4CH_3$ | $-(CH_2)_{12}CH_3$ |
| ER811392 | (tryptophan-acetamide-isoleucine structure) | $-(CH_2)_2C_6H_5$ | $-(CH_2)_9CH_3$ |
| ER811393 | (tryptophan-acetamide-isoleucine structure) | $-(CH_2)_{18}CH_3$ | $-(CH_2)_{12}CH_3$ |

TABLE 1-continued

Compounds of formula XIII, where R¹ is H

| Compound No. | U | V | R^{W4} |
|---|---|---|---|
| ER811394 | (tryptophan-Ile derivative) | —(CH$_2$)$_{10}$CH$_3$ | —(CH$_2$)$_9$CH$_3$ |
| ER811395 | (tryptophan-Ile derivative) | —(CH$_2$)$_{18}$CH$_3$ | —(CH$_2$)$_9$CH$_3$ |
| ER811254 | (5-benzyloxy-tryptophan-Val derivative) | —(CH$_2$)$_{18}$CH$_3$ | —(CH$_2$)$_{12}$CH$_3$ |
| ER811255 | (Boc-Val derivative) | —(CH$_2$)$_{18}$CH$_3$ | —(CH$_2$)$_{12}$CH$_3$ |
| ER812011 | (5-benzyloxy-tryptophan-Ile derivative) | —(CH$_2$)$_{18}$CH$_3$ | —(CH$_2$)$_{12}$CH$_3$ |

Compounds of formula XV, where $R^{W3}$ is a $C_{1-20}$ alkyl, $C_{1-20}$ alkenyl, or $C_{1-20}$ alkynyl group, can be prepared in a manner analogous to the synthetic route shown in Scheme I via a compound of formula XIV, which can be prepared by reacting a compound of formula V with an alkyl halide or an alkyl mesylate corresponding to $R^{W3}$-Hal or $R^{W3}$-OMs, respectively.

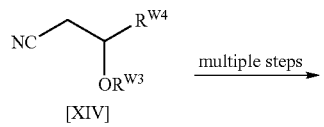

[XIV]

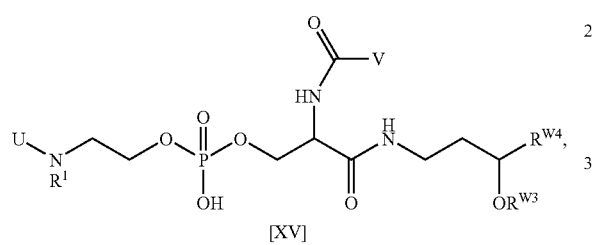

[XV]

Compounds of formula XV, where $R^{W3}$ is a $C_{1-21}$ acyl group, can be prepared as shown in Scheme 2 via a compound of formula XI. Compounds of formula XI can be N-deprotected under acidic conditions and then reacted with a carboxylic acid using a coupling reagent to give a protected phosphonate intermediate, which can be subsequently treated with catalytic Pd(0), thereby removing the allyl protecting group to produce the compound of formula XV.

Scheme 2

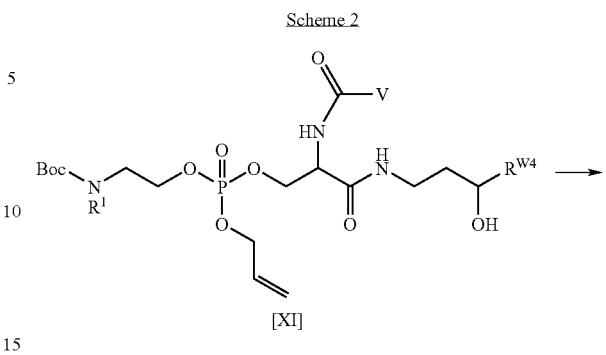

[XI]

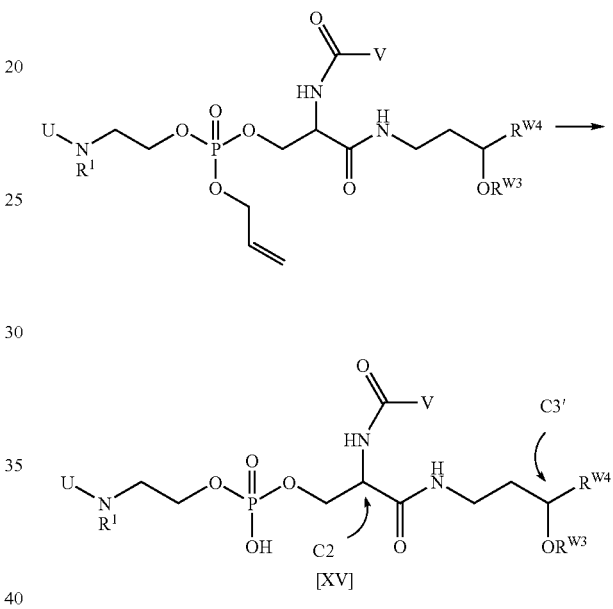

[XV]

Examples of compounds of Formula XV, where $R^1$ is H, $R^{W3}$ is an acyl group, and C2 and C3' have the S- and R-configuration, respectively, unless otherwise indicated are shown in Table 2.

TABLE 2

| | Compounds of formula XV, where $R^1$ is H | | | |
|---|---|---|---|---|
| Compound No. | U | V | $R^{W3}$ | $R^{W4}$ |
| ER809834 | ![structure] | —(CH$_2$)$_{12}$CH$_3$ | —C(O)(CH$_2$)$_4$CH$_3$ | —(CH$_2$)$_6$CH$_3$ |

TABLE 2-continued

Compounds of formula XV, where $R^1$ is H

| Compound No. | U | V | $R^{W3}$ | $R^{W4}$ |
|---|---|---|---|---|
| ER809835 | (isoleucine-indolylacetamide structure) | —(CH$_2$)$_{12}$CH$_3$ | —C(O)(CH$_2$)$_{10}$CH$_3$ | —(CH$_2$)$_6$CH$_3$ |
| ER809836 | (isoleucine-indolylacetamide structure) | —(CH$_2$)$_{12}$CH$_3$ | —C(O)(CH$_2$)$_{12}$CH$_3$ | —(CH$_2$)$_6$CH$_3$ |
| ER809841 | (tBuO-C(O) structure) | —(CH$_2$)$_4$CH$_3$ | —C(O)(CH$_2$)$_{12}$CH$_3$ | —(CH$_2$)$_6$CH$_3$ |
| ER809842 | (isoleucine-indolylacetamide structure) | —(CH$_2$)$_4$CH$_3$ | —C(O)(CH$_2$)$_{18}$CH$_3$ | —(CH$_2$)$_6$CH$_3$ |
| ER809845 | (isoleucine-indolylacetamide structure) | —(CH$_2$)$_4$CH$_3$ | —C(O)(CH$_2$)$_{10}$CH$_3$ | —(CH$_2$)$_6$CH$_3$ |

TABLE 2-continued

Compounds of formula XV, where $R^1$ is H

| Compound No. | U | V | $R^{W3}$ | $R^{W4}$ |
|---|---|---|---|---|
| ER809846 | (tryptophan-Ile structure) | —(CH$_2$)$_4$CH$_3$ | —C(O)(CH$_2$)$_{12}$CH$_3$ | —(CH$_2$)$_6$CH$_3$ |
| ER809950 | (tryptophan-Ile structure) | —(CH$_2$)$_{10}$CH$_3$ | —C(O)(CH$_2$)$_{10}$CH$_3$ | —(CH$_2$)$_6$CH$_3$ |
| ER809951 | (tryptophan-Ile structure) | —(CH$_2$)$_{10}$CH$_3$ | —C(O)(CH$_2$)$_{12}$CH$_3$ | —(CH$_2$)$_6$CH$_3$ |
| ER809959 | (tryptophan-Ile structure) | —(CH$_2$)$_{18}$CH$_3$ | —C(O)CH$_3$ | —(CH$_2$)$_6$CH$_3$ |
| ER809960 | (tryptophan-Ile structure) | —(CH$_2$)$_{18}$CH$_3$ | —C(O)(CH$_2$)$_4$CH$_3$ | —(CH$_2$)$_6$CH$_3$ |

TABLE 2-continued

Compounds of formula XV, where $R^1$ is H

| Compound No. | U | V | $R^{W3}$ | $R^{W4}$ |
|---|---|---|---|---|
| ER809964 | tBuO-C(O)- (wavy) | —(CH$_2$)$_{10}$CH$_3$ | —C(O)CH$_3$ | —(CH$_2$)$_6$CH$_3$ |
| ER809965 | tBuO-C(O)- (wavy) | —(CH$_2$)$_{10}$CH$_3$ | —C(O)(CH$_2$)$_{10}$CH$_3$ | —(CH$_2$)$_6$CH$_3$ |
| ER810676 | indole-CH$_2$-C(O)-NH-CH(sec-Bu)-C(O)- | —(CH$_2$)$_{10}$CH$_3$ | —C(O)(CH$_2$)$_4$CH$_3$ | —(CH$_2$)$_{12}$CH$_3$ (R,S)-mixture at C3' |
| ER810677 | indole-CH$_2$-C(O)-NH-CH(sec-Bu)-C(O)- | —(CH$_2$)$_{10}$CH$_3$ | —C(O)(CH$_2$)$_{10}$CH$_3$ | —(CH$_2$)$_{12}$CH$_3$ (R,S)-mixture at C3' |
| ER810698 | indole-CH$_2$-C(O)-NH-CH(sec-Bu)-C(O)- | —CH$_3$ | —C(O)(CH$_2$)$_{18}$CH$_3$ | —(CH$_2$)$_6$CH$_3$ |
| ER810699 | indole-CH$_2$-C(O)-NH-CH(sec-Bu)-C(O)- | —CH$_3$ | —C(O)(CH$_2$)$_{12}$CH$_3$ | —(CH$_2$)$_6$CH$_3$ |

TABLE 2-continued

Compounds of formula XV, where $R^1$ is H

| Compound No. | U | V | $R^{W3}$ | $R^{W4}$ |
|---|---|---|---|---|
| ER810701 | (isoleucine-tryptophan amide structure) | —$CH_3$ | —$C(O)(CH_2)_{10}CH_3$ | —$(CH_2)_6CH_3$ |
| ER808701 | (4-hydroxyphenyl-CH_2-CH(CO_2H)-C(O)- structure, Na salt) | —$(CH_2)_{12}CH_3$ (R)-config. at C3' | —$C(O)(CH_2)_{10}CH_3$ | —$(CH_2)_6CH_3$ |
| ER808839 | ($F_3C$-C(O)- structure, Na salt) | —$(CH_2)_{12}CH_3$ (R)-config. at C2 | —$C(O)(CH_2)_{10}CH_3$ | —$(CH_2)_6CH_3$ |

Compounds of formula XV, where $R^{W4}$ is H and $R^{W3}$ is an acyl group can be prepared as shown in Scheme 3. Accordingly, N-Fmoc-L- or D-serine can be reacted with TBDPS-protected propanolamine using an appropriate coupling agent, such as a carbodiimide, to form a compound of formula XVI. The choice of L- or D-serine determines the configuration at C2. The compound of formula XVI can be subsequently reacted with Boc-phosphorylating reagent IX, followed by oxidation with hydrogen peroxide to yield a phosphonate of formula XVII. The silyl protecting group is removed with tetrabutylammonium fluoride and the Boc protecting group removed under acidic conditions to yield a compound of formula XIX. Acylation, reductive amination, or sulfonation of the amine of a compound of formula XIX gives a compound of formula XX. The hydroxyl group of the compound of formula XX can be reacted with a compound containing a carboxylic acid under coupling conditions to give a compound of formula XXI. Removal of the Fmoc-protecting group followed by coupling the resulting amine with a compound containing a carboxylic acid under coupling conditions gives a compound of formula XXIII. Removal of the allyl protecting group using catalytic palladium tetrakistriphenylphosphine gives a compound of formula XXIV.

Scheme 3

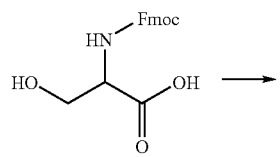

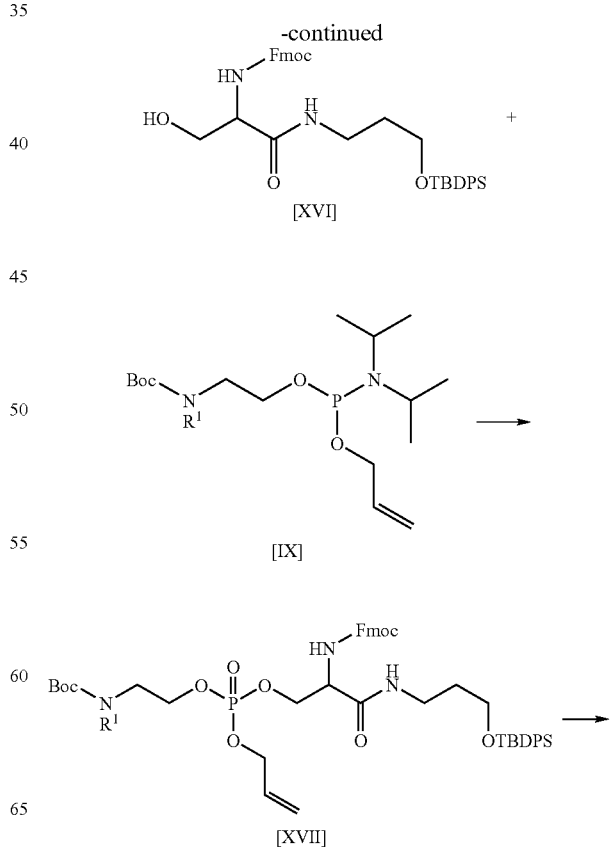

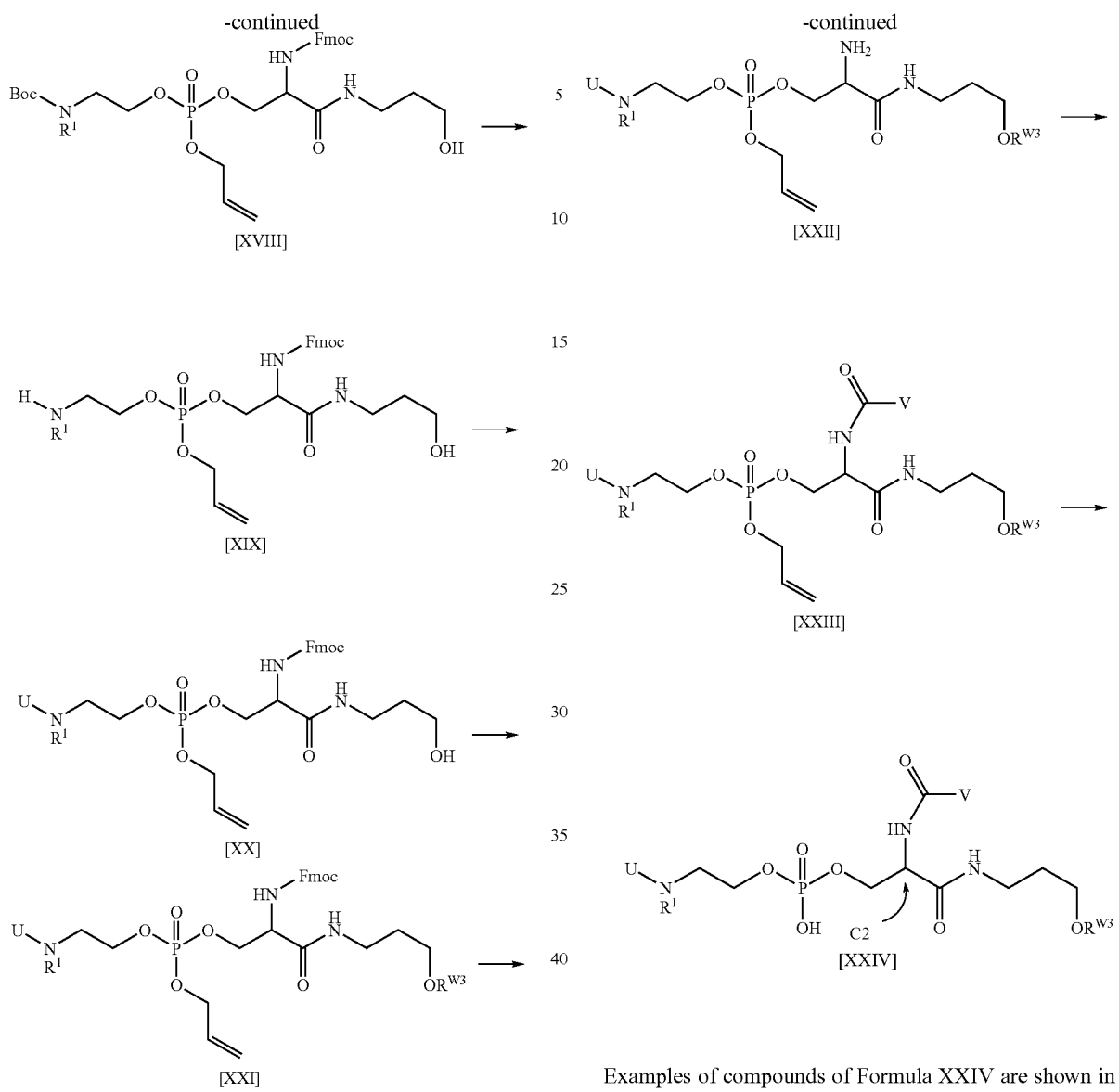
Examples of compounds of Formula XXIV are shown in Table 3, where $R^1$ is H and C2 has an (S)-configuration.
TABLE 3
| Compounds of formula XXIV, where $R^1$ is H | | | |
|---|---|---|---|
| Compound No. | U | V | $R^{W3}$ |
| ER811203 | (see structure) | —$CH_3$ | —$C(O)(CH_2)_{10}CH_3$ |

TABLE 3-continued

Compounds of formula XXIV, where $R^1$ is H

| Compound No. | U | V | $R^{W3}$ |
|---|---|---|---|
| ER811211 | (structure) | —(CH$_2$)$_{14}$CH$_3$ | —C(O)(CH$_2$)$_{10}$CH$_3$ |
| ER811212 | (structure) | —(CH$_2$)$_{10}$CH$_3$ | —C(O)(CH$_2$)$_{14}$CH$_3$ |
| ER811213 | (structure) | —(CH$_2$)$_{18}$CH$_3$ | —C(O)(CH$_2$)$_{4}$CH$_3$ |
| ER811214 | (structure) | —(CH$_2$)$_{4}$CH$_3$ | —C(O)(CH$_2$)$_{18}$CH$_3$ |
| ER811219 | (structure) | —(CH$_2$)$_{12}$CH$_3$ | —C(O)CH$_3$ |

TABLE 3-continued

Compounds of formula XXIV, where R¹ is H

| Compound No. | U | V | $R^{W3}$ |
|---|---|---|---|
| ER811220 | (structure: N-(indol-3-ylacetyl)-isoleucine acyl group) | —(CH$_2$)$_{14}$CH$_3$ | —C(O)CH$_3$ |
| ER811221 | (structure: N-(indol-3-ylacetyl)-isoleucine acyl group) | —(CH$_2$)$_{18}$CH$_3$ | —C(O)CH$_3$ |
| ER811228 | (structure: N-(indol-3-ylacetyl)-isoleucine acyl group) | —(CH$_2$)$_{14}$CH$_3$ | —C(O)(CH$_2$)$_{14}$CH$_3$ |
| ER811232 | (structure: N-(5-bromo-indol-3-ylacetyl)-isoleucine acyl group) | —(CH$_2$)$_{14}$CH$_3$ | —C(O)(CH$_2$)$_{10}$CH$_3$ |
| ER811233 | (structure: N-(5-benzyloxy-indol-3-ylacetyl)-isoleucine acyl group) | —(CH$_2$)$_{14}$CH$_3$ | —C(O)(CH$_2$)$_{10}$CH$_3$ |

TABLE 3-continued

Compounds of formula XXIV, where $R^1$ is H

| Compound No. | U | V | $R^{W3}$ |
|---|---|---|---|
| ER811237 | 5-chloro-indol-3-yl-CH₂-C(O)NH-CH(CH(CH₃)CH₂CH₃)-C(O)- | —(CH₂)₁₄CH₃ | —C(O)(CH₂)₁₀CH₃ |
| ER811243 | 5-phenyl-indol-3-yl-CH₂-C(O)NH-CH(CH(CH₃)CH₂CH₃)-C(O)- | —(CH₂)₁₄CH₃ | —C(O)(CH₂)₁₀CH₃ |
| ER811244 | 5-(4-trifluoromethylphenyl)-indol-3-yl-CH₂-C(O)NH-CH(CH(CH₃)CH₂CH₃)-C(O)- | —(CH₂)₁₄CH₃ | —C(O)(CH₂)₁₀CH₃ |
| ER811249 | 5-(4-cyanophenyl)-indol-3-yl-CH₂-C(O)NH-CH(CH(CH₃)CH₂CH₃)-C(O)- | —(CH₂)₁₄CH₃ | —C(O)(CH₂)₁₀CH₃ |
| ER811250 | 5-(quinolin-8-yl)-indol-3-yl-CH₂-C(O)NH-CH(CH(CH₃)CH₂CH₃)-C(O)- | —(CH₂)₁₄CH₃ | —C(O)(CH₂)₁₀CH₃ |

Compounds of formula I in which W is —C(O)N($R^{W1}$)($CH_2$)$_c$CH(O$R^{W3}$)($CH_2$)$_e$O$R^{W5}$, where each of c and e is 1, $R^{W1}$ is H, $R^{W5}$ is $C_{1-21}$ acyl, and each of U and V is as defined above can be prepared by starting with (R)- or (S)-2,2-dimethyl-1,3-dioxolane-4-methanol. Conversion of the hydroxyl group to an amino group via mesylation, displacement with azide, and reduction of the azide to an amine gives a compound that, upon coupling to a serine derivative, gives a compound of formula XXV. Removal of the acetonide protecting group under acidic conditions and subsequent alkylation or acylation of the resulting hydroxyl groups (exhaustively, resulting in identical $R^{W3}$ and $R^{W5}$ groups, or selectively, resulting in different $R^{W3}$ and $R^{W5}$ groups) gives a compound of formula XXVI. This compound can be deprotected via a hydrogenation reaction and carried forward using the synthetic methodology previously described herein to give a compound of formula XXVIII.

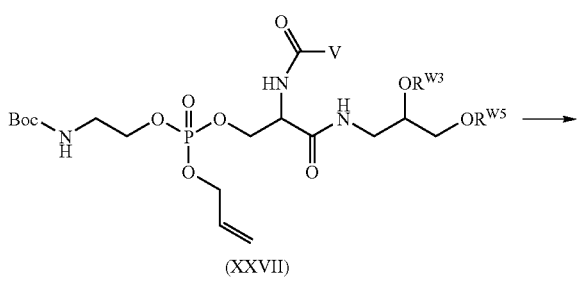

(XXVII)

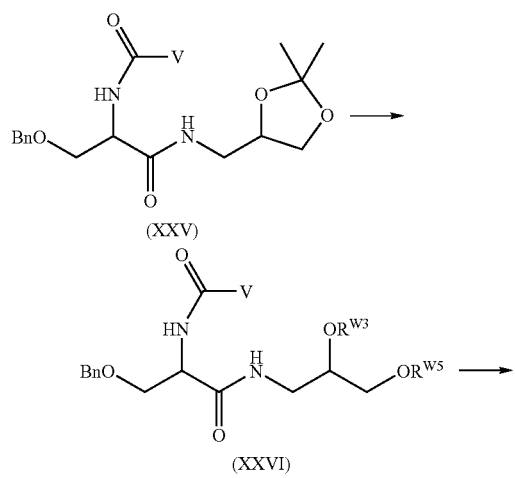

(XXV)

(XXVI)

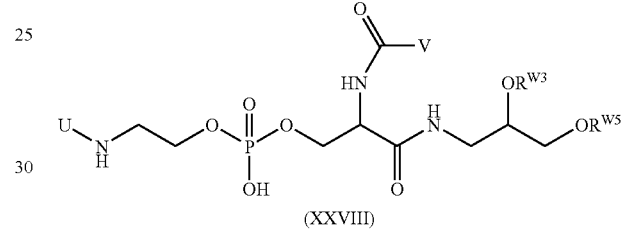

(XXVIII)

Examples of a compound of formula XXVIII are ER811261 and ER811245.

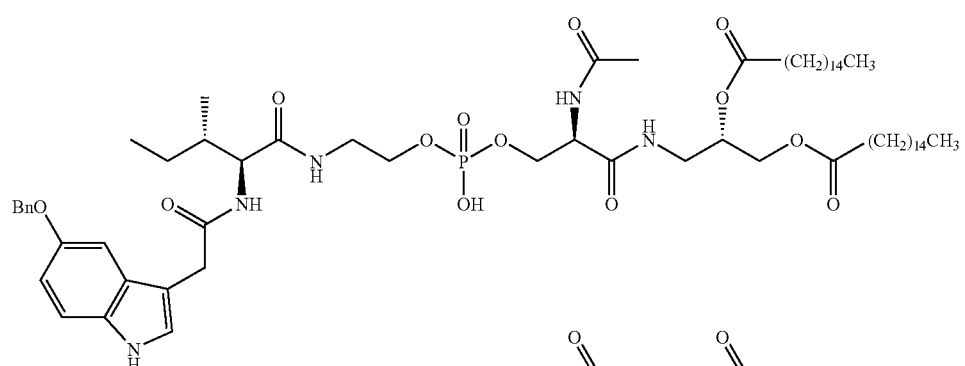

(ER811261)

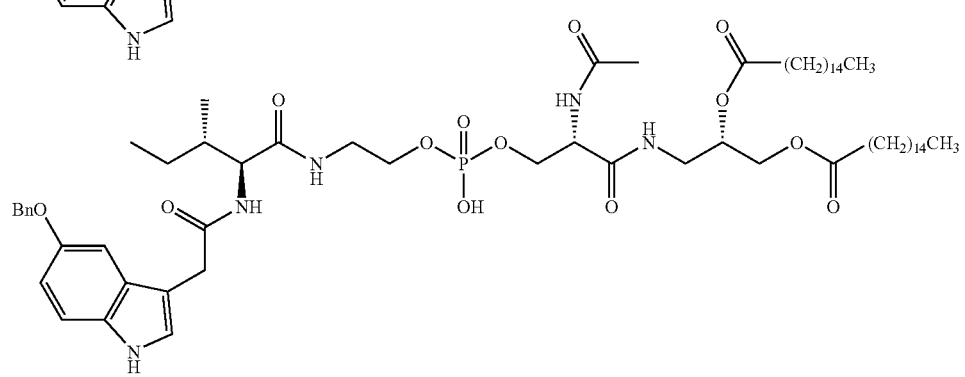

(ER811245)

For the preparation of compounds of formula I where W is H, N-Fmoc-glycinol can be reacted with a compound of formula IX, followed by subsequent reactions analogous to those shown in Scheme 1 to produce a compound of formula XXIX.

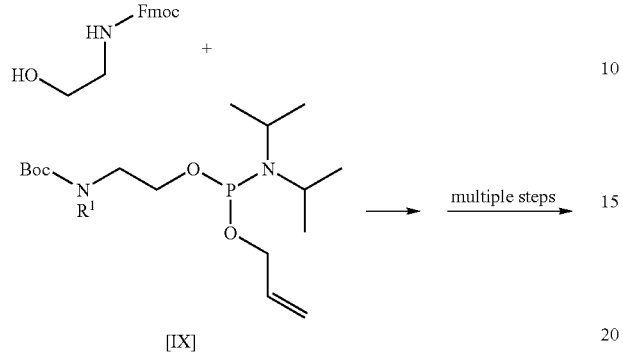

[IX]

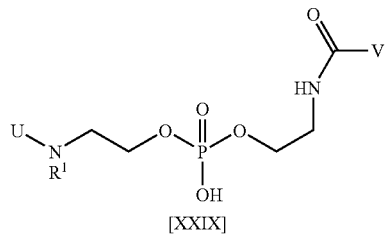

[XXIX]

Examples of compounds of formula XXIX, where $R^1$ is H, are shown in Table 4.

TABLE 4

Compounds of formula XXIX, where $R^1$ is H

| Compound No. | U | V |
|---|---|---|
| ER811230 | (tryptophan-derived acyl group with sec-butyl side chain) | —(CH$_2$)$_{14}$CH$_3$ |
| ER811231 | (tryptophan-derived acyl group with sec-butyl side chain) | —(CH$_2$)$_{18}$CH$_3$ |
| ER811246 | (5-benzyloxy-tryptophan-derived acyl group with sec-butyl side chain) | (4-heptylphenyl group, —C$_6$H$_4$—(CH$_2$)$_6$CH$_3$) |

TABLE 4-continued
Compounds of formula XXIX, where R¹ is H
| Compound No. | U | V |
|---|---|---|
| ER811247 | 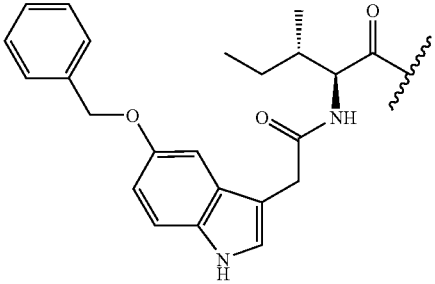 | 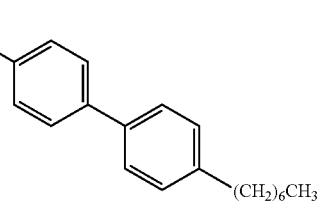 (CH₂)₆CH₃ |
| ER811248 | 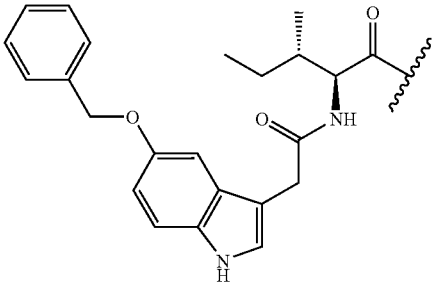 | 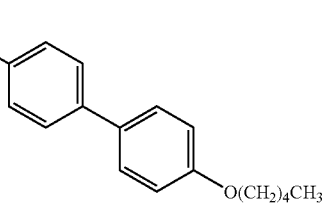 O(CH₂)₄CH₃ |
| ER811251 | 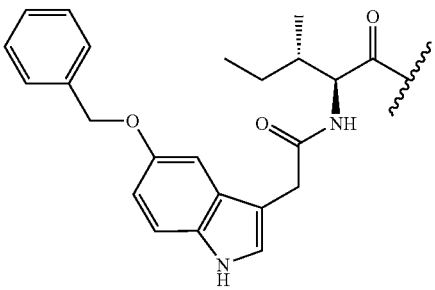 | 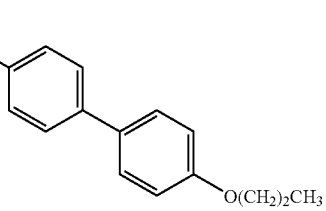 O(CH₂)₂CH₃ |
| ER811252 | 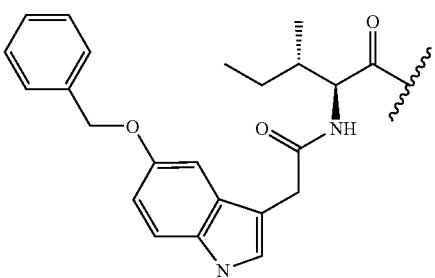 | 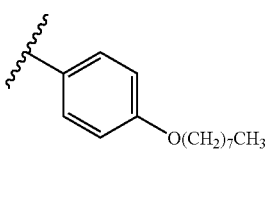 O(CH₂)₇CH₃ |
| ER811253 | 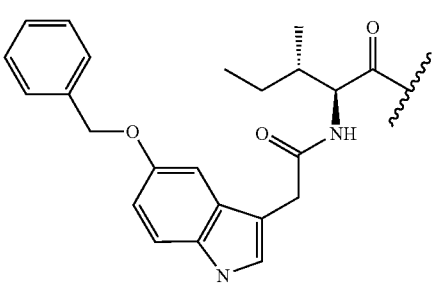 | 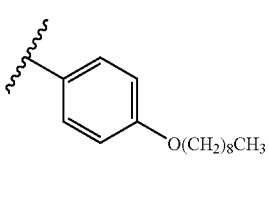 O(CH₂)₈CH₃ |

Compounds of formula I where W is —C(O)N(R$^{W1}$)R$^{W2}$ can be prepared by coupling HN(R$^{W1}$)R$^{W2}$ to an appropriately protected L- or D-serine analog to produce a compound of formula XXX, followed by subsequent reactions analogous to those shown in Scheme 1 to produce a compound of formula XXXI. Examples of compounds of formula XXXI, where each of R$^1$ and R$^{W1}$ is H and C2 has the S-configuration, unless indicated otherwise, are shown in Table 4.

TABLE 4

Compounds of formula XXXI, where each of R$^1$ and R$^{W1}$ is H

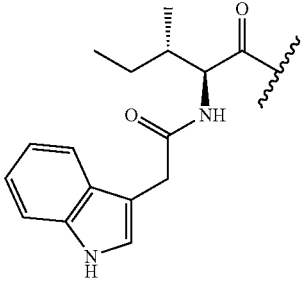

| Compound No. | U | V | R$^{W2}$ |
|---|---|---|---|
| ER811234 | 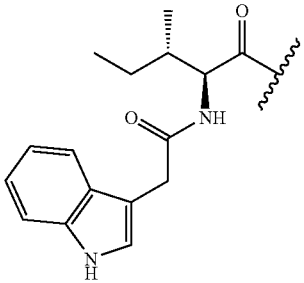 | —(CH$_2$)$_{10}$CH$_3$ | —(CH$_2$)$_9$CH$_3$ |
| ER811132 | 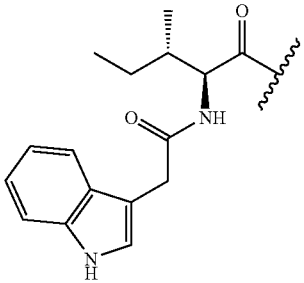 | —(CH$_2$)$_{18}$CH$_3$ | —(CH$_2$)$_9$CH$_3$ |
| ER811236 | 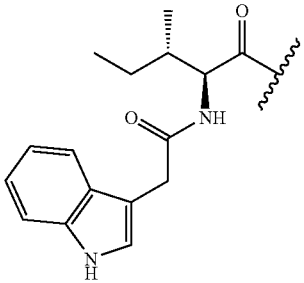 | | 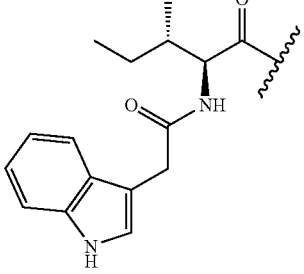 |

Compounds of formula I where W is —(CH$_2$)$_c$O(CH$_2$)$_d$CH(OR$^{W3}$)R$^{W4}$ can be prepared as shown in Scheme 3 using the methodology described in U.S. Patent Application Publication No. 20030153532 A1. A protected serine analog is prepared by reaction L- or D-serine methyl ester with ethyl benzimidate to produce the benzimidine of serine, which is subsequently reduced with DIBAL to produce the compound of formula XXXII. The hydroxyl group of XXXII can be O-alkylated with the tosylate of formula XXXIII and the benzimidine removed by treatment with refluxing 4M HCl to produce a compound of formula XXXV. Amino group protection or N-acylation produces a compound of formula XXXVI, which is subsequently reacted with a compound of formula IX to produce a compound of formula XXXVII. By steps analogous to those described above in Scheme 2, the compound of formula XXXVII is transformed to a compound of formula XXXVIII. Examples of compounds of formula XXXVIII are shown in Table 5, where R$^1$ is H and each of C2 and C3' has the R-configuration, unless indicated otherwise.

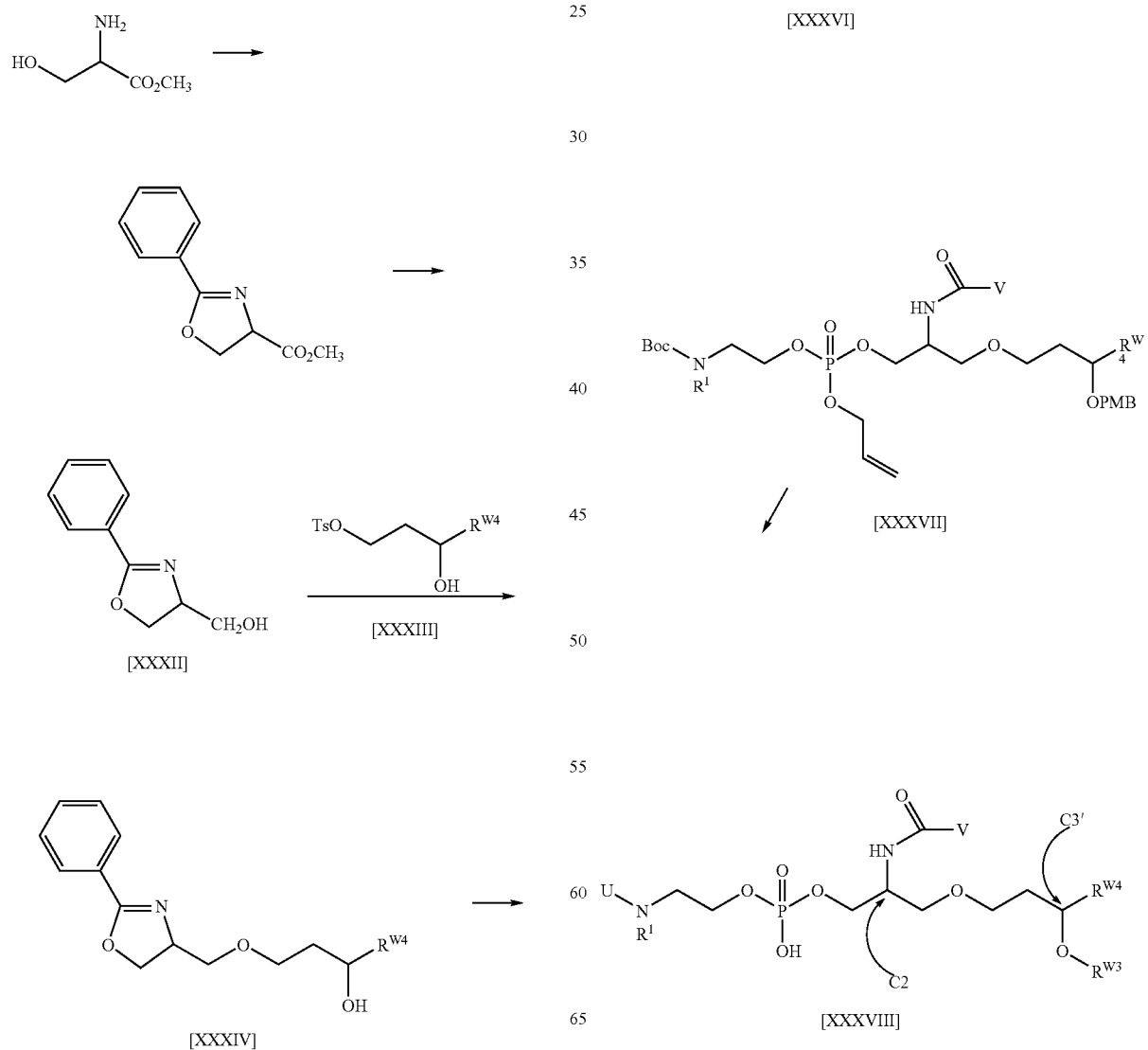

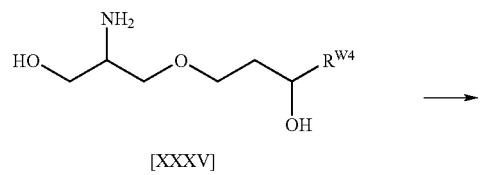

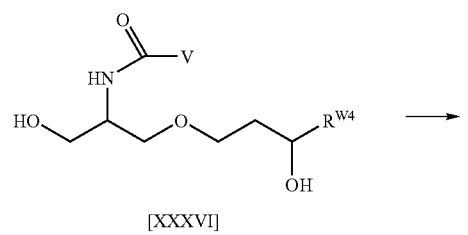

TABLE 5

Compounds of formula XXXVIII, where $R^1$ is H

| Compound No. | U | V | $R^{W3}$ | $R^{W4}$ |
| --- | --- | --- | --- | --- |
| ER811208 | (structure: Glu with tBuO ester and N-Boc) | —$(CH_2)_{12}CH_3$ | —$C(O)(CH_2)_{10}CH_3$ | —$(CH_2)_6CH_3$ |
| ER811209 | (structure: Glu with free COOH and N-indolylacetyl) | —$(CH_2)_{12}CH_3$ | —$C(O)(CH_2)_{10}CH_3$ | —$(CH_2)_6CH_3$ |
| ER811210 | (structure: Glu with allyl ester and N-Boc) | —$(CH_2)_{12}CH_3$ | —$C(O)(CH_2)_{10}CH_3$ | —$(CH_2)_6CH_3$ |
| ER804469 | (structure: sodium phosphate ester with pendant carboxylic acid) | —$(CH_2)_{12}CH_3$ | —$C(O)(CH_2)_{10}CH_3$ | —$(CH_2)_6CH_3$ |
| ER804529 | (structure: dicarboxylic acid) | —$(CH_2)_{12}CH_3$ | —$C(O)(CH_2)_{10}CH_3$ | —$(CH_2)_6CH_3$ |
| ER810625 | H-L-Phe-(Gly)$_4$- (attached to ketone chain) | —$(CH_2)_{12}CH_3$ | —$C(O)(CH_2)_{10}CH_3$ | —$(CH_2)_6CH_3$ |
| ER811189 | (structure: Ile with N-indolylpropanoyl, $NH_4$ salt) | —$(CH_2)_{12}CH_3$ | —$C(O)(CH_2)_{10}CH_3$ | —$(CH_2)_6CH_3$ |

TABLE 5-continued

Compounds of formula XXXVIII, where $R^1$ is H

| Compound No. | U | V | $R^{W3}$ | $R^{W4}$ |
|---|---|---|---|---|
| ER811197 | (4-chloro-indol-3-yl-acetamide of isoleucine) | —(CH$_2$)$_{12}$CH$_3$ | —C(O)(CH$_2$)$_{10}$CH$_3$ | —(CH$_2$)$_6$CH$_3$ |
| ER811198 | (indol-3-yl-butanamide of isoleucine) | —(CH$_2$)$_{12}$CH$_3$ | —C(O)(CH$_2$)$_{10}$CH$_3$ | —(CH$_2$)$_6$CH$_3$ |
| ER811199 | (5-bromo-indol-3-yl-acetamide of isoleucine) | —(CH$_2$)$_{12}$CH$_3$ | —C(O)(CH$_2$)$_{10}$CH$_3$ | —(CH$_2$)$_6$CH$_3$ |
| ER811205 | (N-methyl-indol-3-yl-acetamide of isoleucine) | —(CH$_2$)$_{12}$CH$_3$ | —C(O)(CH$_2$)$_{10}$CH$_3$ | —(CH$_2$)$_6$CH$_3$ |
| ER811215 | (Boc-3-pyridyl-alanine amide of isoleucine) | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R¹ is H

| Compound No. | U | V | $R^{W3}$ | $R^{W4}$ |
|---|---|---|---|---|
| ER811217 | (structure: tBuO-C(O)-NH-CH(CH₂-imidazole)-C(O)-NH-CH(sec-butyl)-C(O)-) | —(CH₂)₁₂CH₃ | —C(O)(CH₂)₁₀CH₃ | —(CH₂)₆CH₃ |
| ER811222 | (structure: 5-benzyloxy-indol-3-yl-CH₂-C(O)-NH-CH(sec-butyl)-C(O)-) | —(CH₂)₁₂CH₃ | —C(O)(CH₂)₁₀CH₃ | —(CH₂)₆CH₃ |
| ER811223 | (structure: 5-methoxy-indol-3-yl-CH₂-C(O)-NH-CH(sec-butyl)-C(O)-) | —(CH₂)₁₂CH₃ | —C(O)(CH₂)₁₀CH₃ | —(CH₂)₆CH₃ |
| ER811225 | (structure: 4,5,6,7-tetrafluoro-indol-3-yl-CH₂-C(O)-NH-CH(sec-butyl)-C(O)-) | —(CH₂)₁₂CH₃ | —C(O)(CH₂)₁₀CH₃ | —(CH₂)₆CH₃ |
| ER811226 | (structure: indol-4-yl-C(O)-NH-CH(sec-butyl)-C(O)-) | —(CH₂)₁₂CH₃ | —C(O)(CH₂)₁₀CH₃ | —(CH₂)₆CH₃ |

TABLE 5-continued

Compounds of formula XXXVIII, where $R^1$ is H

| Compound No. | U | V | $R^{W3}$ | $R^{W4}$ |
|---|---|---|---|---|
| ER811258 | 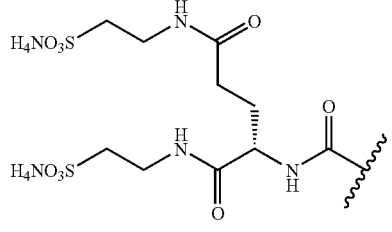<br>NH$_4$ salt | —(CH$_2$)$_{12}$CH$_3$ | —C(O)(CH$_2$)$_{10}$CH$_3$ | —(CH$_2$)$_6$CH$_3$ |
| ER804283 | 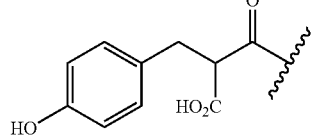<br>Na salt | —(CH$_2$)$_{12}$CH$_3$ | —C(O)(CH$_2$)$_{10}$CH$_3$ | —(CH$_2$)$_6$CH$_3$ |
| ER804335 | 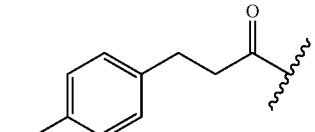 | —(CH$_2$)$_{12}$CH$_3$ | —C(O)(CH$_2$)$_{10}$CH$_3$ | —(CH$_2$)$_6$CH$_3$ |
| ER808263 | 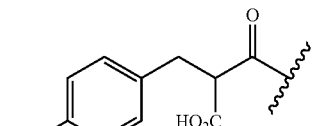<br>Na salt | —(CH$_2$)$_{12}$CH$_3$<br>C2 has S-config. | —C(O)(CH$_2$)$_{10}$CH$_3$<br>C3′ has S-config. | —(CH$_2$)$_6$CH$_3$ |
| ER808265 | 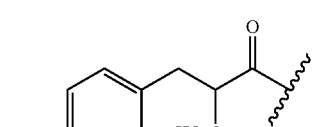<br>Na salt | —(CH$_2$)$_{12}$CH$_3$ | —C(O)(CH$_2$)$_{10}$CH$_3$<br>C3′ has S-config. | —(CH$_2$)$_6$CH$_3$ |
| ER809050 | 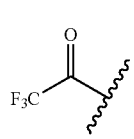 | —(CH$_2$)$_{12}$CH$_3$<br>C2 has S-config. | —C(O)(CH$_2$)$_{10}$CH$_3$<br>C3′ has S-config. | —(CH$_2$)$_6$CH$_3$ |
| ER809388 | 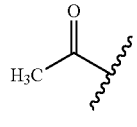 | —(CH$_2$)$_{12}$CH$_3$ | —C(O)(CH$_2$)$_{10}$CH$_3$ | —(CH$_2$)$_6$CH$_3$ |
| ER809406 | 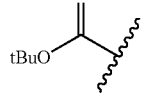 | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where $R^1$ is H

| Compound No. | U | V | $R^{W3}$ | $R^{W4}$ |
|---|---|---|---|---|
| ER808579 | 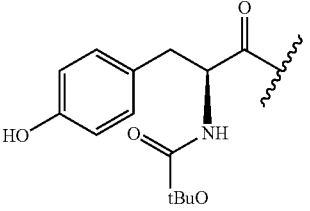 | —(CH$_2$)$_{12}$CH$_3$ | —C(O)(CH$_2$)$_{10}$CH$_3$ | —(CH$_2$)$_6$CH$_3$ |
| ER808580 | 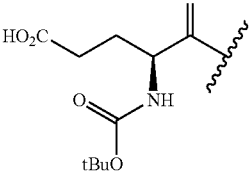 | —(CH$_2$)$_{12}$CH$_3$ | —C(O)(CH$_2$)$_{10}$CH$_3$ | —(CH$_2$)$_6$CH$_3$ |
| ER808581 | 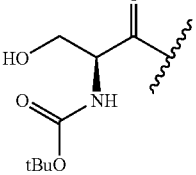 | —(CH$_2$)$_{12}$CH$_3$ | —C(O)(CH$_2$)$_{10}$CH$_3$ | —(CH$_2$)$_6$CH$_3$ |
| ER808584 | 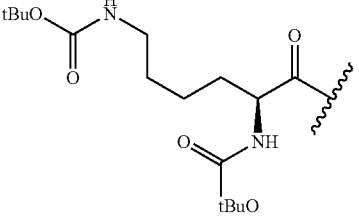 | —(CH$_2$)$_{12}$CH$_3$ | —C(O)(CH$_2$)$_{10}$CH$_3$ | —(CH$_2$)$_6$CH$_3$ |
| ER808585 | 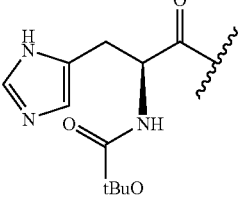 | —(CH$_2$)$_{12}$CH$_3$ | —C(O)(CH$_2$)$_{10}$CH$_3$ | —(CH$_2$)$_6$CH$_3$ |
| ER808586 | 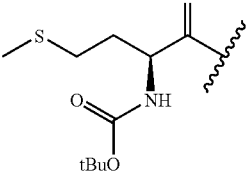 | —(CH$_2$)$_{12}$CH$_3$ | —C(O)(CH$_2$)$_{10}$CH$_3$ | —(CH$_2$)$_6$CH$_3$ |
| ER808587 | 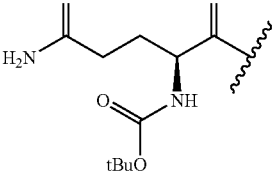 | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R¹ is H

| Compound No. | U | V | $R^{W3}$ | $R^{W4}$ |
|---|---|---|---|---|
| ER808588 | (methylsulfinyl-ethyl, NHBoc α-amino ketone) | —(CH$_2$)$_{12}$CH$_3$ | —C(O)(CH$_2$)$_{10}$CH$_3$ | —(CH$_2$)$_6$CH$_3$ |
| ER808928 | (methylsulfonyl-ethyl, NHBoc α-amino ketone) | —(CH$_2$)$_{12}$CH$_3$ | —C(O)(CH$_2$)$_{10}$CH$_3$ | —(CH$_2$)$_6$CH$_3$ |
| ER808929 | (N-Boc glycyl) | —(CH$_2$)$_{12}$CH$_3$ | —C(O)(CH$_2$)$_{10}$CH$_3$ | —(CH$_2$)$_6$CH$_3$ |
| ER808931 | (N-Boc azetidine-2-carbonyl) | —(CH$_2$)$_{12}$CH$_3$ | —C(O)(CH$_2$)$_{10}$CH$_3$ | —(CH$_2$)$_6$CH$_3$ |
| ER808932 | (N-Boc leucyl) | —(CH$_2$)$_{12}$CH$_3$ | —C(O)(CH$_2$)$_{10}$CH$_3$ | —(CH$_2$)$_6$CH$_3$ |
| ER808934 | (N-Boc norvalyl) | —(CH$_2$)$_{12}$CH$_3$ | —C(O)(CH$_2$)$_{10}$CH$_3$ | —(CH$_2$)$_6$CH$_3$ |
| ER808936 | (N-Boc 4-chlorophenylalanyl) | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where $R^1$ is H

| Compound No. | U | V | $R^{W3}$ | $R^{W4}$ |
|---|---|---|---|---|
| ER808938 | (N-methyl, N-Boc phenylalanine-derived ketone) | —(CH$_2$)$_{12}$CH$_3$ | —C(O)(CH$_2$)$_{10}$CH$_3$ | —(CH$_2$)$_6$CH$_3$ |
| ER808939 | (N-Boc valine-derived ketone) | —(CH$_2$)$_{12}$CH$_3$ | —C(O)(CH$_2$)$_{10}$CH$_3$ | —(CH$_2$)$_6$CH$_3$ |
| ER808940 | (N-Boc tryptophan-derived, tBu ester) | —(CH$_2$)$_{12}$CH$_3$ | —C(O)(CH$_2$)$_{10}$CH$_3$ | —(CH$_2$)$_6$CH$_3$ |
| ER808941 | (N-Boc valine-derived ketone) | —(CH$_2$)$_{12}$CH$_3$ | —C(O)(CH$_2$)$_{10}$CH$_3$ | —(CH$_2$)$_6$CH$_3$ |
| ER808942 | (O-benzyl threonine-derived, tBu ester) | —(CH$_2$)$_{12}$CH$_3$ | —C(O)(CH$_2$)$_{10}$CH$_3$ | —(CH$_2$)$_6$CH$_3$ |
| ER808943 | (N-Boc proline-derived ketone) | —(CH$_2$)$_{12}$CH$_3$ | —C(O)(CH$_2$)$_{10}$CH$_3$ | —(CH$_2$)$_6$CH$_3$ |
| ER808944 | (N-Boc isoleucine-derived ketone) | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R[1] is H

| Compound No. | U | V | R[W3] | R[W4] |
|---|---|---|---|---|
| ER808945 | 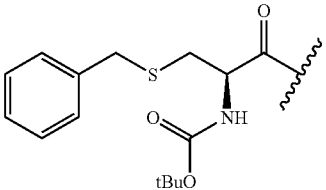 | —(CH$_2$)$_{12}$CH$_3$ | —C(O)(CH$_2$)$_{10}$CH$_3$ | —(CH$_2$)$_6$CH$_3$ |
| ER808950 | 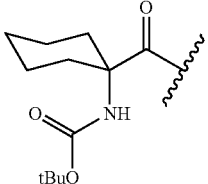 | —(CH$_2$)$_{12}$CH$_3$ | —C(O)(CH$_2$)$_{10}$CH$_3$ | —(CH$_2$)$_6$CH$_3$ |
| ER808951 | 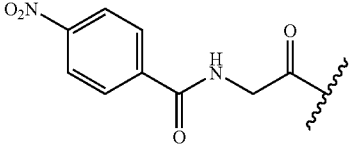 | —(CH$_2$)$_{12}$CH$_3$ | —C(O)(CH$_2$)$_{10}$CH$_3$ | —(CH$_2$)$_6$CH$_3$ |
| ER808952 | 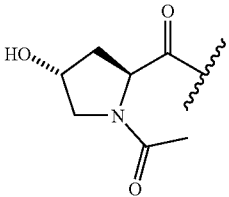 | —(CH$_2$)$_{12}$CH$_3$ | —C(O)(CH$_2$)$_{10}$CH$_3$ | —(CH$_2$)$_6$CH$_3$ |
| ER808953 | 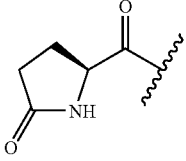 | —(CH$_2$)$_{12}$CH$_3$ | —C(O)(CH$_2$)$_{10}$CH$_3$ | —(CH$_2$)$_6$CH$_3$ |
| ER808954 | 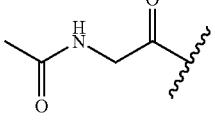 | —(CH$_2$)$_{12}$CH$_3$ | —C(O)(CH$_2$)$_{10}$CH$_3$ | —(CH$_2$)$_6$CH$_3$ |
| ER808955 | 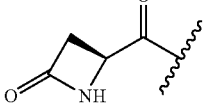 | —(CH$_2$)$_{12}$CH$_3$ | —C(O)(CH$_2$)$_{10}$CH$_3$ | —(CH$_2$)$_6$CH$_3$ |
| ER808956 | 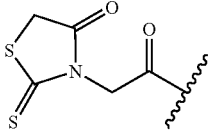 | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R¹ is H

| Compound No. | U | V | $R^{W3}$ | $R^{W4}$ |
|---|---|---|---|---|
| ER808957 | (N-acetyl methionine residue structure) | —(CH$_2$)$_{12}$CH$_3$ | —C(O)(CH$_2$)$_{10}$CH$_3$ | —(CH$_2$)$_6$CH$_3$ |
| ER808958 | (N-acetyl dehydroalanine structure) | —(CH$_2$)$_{12}$CH$_3$ | —C(O)(CH$_2$)$_{10}$CH$_3$ | —(CH$_2$)$_6$CH$_3$ |
| ER808959 | (benzamido hydroxy structure) | —(CH$_2$)$_{12}$CH$_3$ | —C(O)(CH$_2$)$_{10}$CH$_3$ | —(CH$_2$)$_6$CH$_3$ |
| ER808960 | (furan-2-carboxamide glycine structure) | —(CH$_2$)$_{12}$CH$_3$ | —C(O)(CH$_2$)$_{10}$CH$_3$ | —(CH$_2$)$_6$CH$_3$ |
| ER808961 | (N-benzoyl threonine structure) | —(CH$_2$)$_{12}$CH$_3$ | —C(O)(CH$_2$)$_{10}$CH$_3$ | —(CH$_2$)$_6$CH$_3$ |
| ER808962 | (N-acetyl tyrosine structure) | —(CH$_2$)$_{12}$CH$_3$ | —C(O)(CH$_2$)$_{10}$CH$_3$ | —(CH$_2$)$_6$CH$_3$ |
| ER808963 | (N-acetyl 3,4-dimethoxyphenylalanine structure) | —(CH$_2$)$_{12}$CH$_3$ | —C(O)(CH$_2$)$_{10}$CH$_3$ | —(CH$_2$)$_6$CH$_3$ |
| ER808964 | (N-benzoyl glycine structure) | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R¹ is H

| Compound No. | U | V | $R^{W3}$ | $R^{W4}$ |
|---|---|---|---|---|
| ER808965 | furan-CH=CH-C(O)-NH-CH₂-C(O)- | —(CH₂)₁₂CH₃ | —C(O)(CH₂)₁₀CH₃ | —(CH₂)₆CH₃ |
| ER808966 | 2-methylphenyl-C(O)-NH-CH₂-C(O)- | —(CH₂)₁₂CH₃ | —C(O)(CH₂)₁₀CH₃ | —(CH₂)₆CH₃ |
| ER808967 | N-acetyl-phenylalaninyl | —(CH₂)₁₂CH₃ | —C(O)(CH₂)₁₀CH₃ | —(CH₂)₆CH₃ |
| ER808968 | N-acetyl-leucinyl | —(CH₂)₁₂CH₃ | —C(O)(CH₂)₁₀CH₃ | —(CH₂)₆CH₃ |
| ER808969 | phthalimido-CH₂-C(O)- | —(CH₂)₁₂CH₃ | —C(O)(CH₂)₁₀CH₃ | —(CH₂)₆CH₃ |
| ER808970 | N-acetyl-dehydrophenylalaninyl | —(CH₂)₁₂CH₃ | —C(O)(CH₂)₁₀CH₃ | —(CH₂)₆CH₃ |
| ER808971 | indol-3-yl-CH₂-C(O)-NH-CH(CH₃)-C(O)- | —(CH₂)₁₂CH₃ | —C(O)(CH₂)₁₀CH₃ | —(CH₂)₆CH₃ |
| ER808972 | 4-methylphenyl-C(O)-NH-CH₂-C(O)- | —(CH₂)₁₂CH₃ | —C(O)(CH₂)₁₀CH₃ | —(CH₂)₆CH₃ |

TABLE 5-continued

Compounds of formula XXXVIII, where R[1] is H

| Compound No. | U | V | R[W3] | R[W4] |
|---|---|---|---|---|
| ER808973 | (3-methylbenzoyl-glycyl group) | —(CH$_2$)$_{12}$CH$_3$ | —C(O)(CH$_2$)$_{10}$CH$_3$ | —(CH$_2$)$_6$CH$_3$ |
| ER808974 | (2-hydroxybenzoyl-glycyl group) | —(CH$_2$)$_{12}$CH$_3$ | —C(O)(CH$_2$)$_{10}$CH$_3$ | —(CH$_2$)$_6$CH$_3$ |
| ER808975 | (indol-3-ylacetyl-valyl group) | —(CH$_2$)$_{12}$CH$_3$ | —C(O)(CH$_2$)$_{10}$CH$_3$ | —(CH$_2$)$_6$CH$_3$ |
| ER808976 | (indol-3-ylacetyl-leucyl group) | —(CH$_2$)$_{12}$CH$_3$ | —C(O)(CH$_2$)$_{10}$CH$_3$ | —(CH$_2$)$_6$CH$_3$ |
| ER808977 | (indol-3-ylacetyl-isoleucyl group) | —(CH$_2$)$_{12}$CH$_3$ | —C(O)(CH$_2$)$_{10}$CH$_3$ | —(CH$_2$)$_6$CH$_3$ |
| ER811238 | (5-(naphthalen-1-yl)-indol-3-ylacetyl-isoleucyl group) | —(CH$_2$)$_{12}$CH$_3$ | —C(O)(CH$_2$)$_{10}$CH$_3$ | —(CH$_2$)$_6$CH$_3$ |

TABLE 5-continued

Compounds of formula XXXVIII, where R[1] is H

| Compound No. | U | V | R[W3] | R[W4] |
|---|---|---|---|---|
| ER811239 | (benzothiophen-2-yl-indole-isoleucine amide) | —(CH$_2$)$_{12}$CH$_3$ | —C(O)(CH$_2$)$_{10}$CH$_3$ | —(CH$_2$)$_6$CH$_3$ |
| ER811240 | (biphenyl-indole-isoleucine amide) | —(CH$_2$)$_{12}$CH$_3$ | —C(O)(CH$_2$)$_{10}$CH$_3$ | —(CH$_2$)$_6$CH$_3$ |
| ER811241 | (pyridin-3-yl-indole-isoleucine amide) | —(CH$_2$)$_{12}$CH$_3$ | —C(O)(CH$_2$)$_{10}$CH$_3$ | —(CH$_2$)$_6$CH$_3$ |
| ER811242 | (benzofuran-2-yl-indole-isoleucine amide) | —(CH$_2$)$_{12}$CH$_3$ | —C(O)(CH$_2$)$_{10}$CH$_3$ | —(CH$_2$)$_6$CH$_3$ |
| ER118998 | HO$_2$C-CH$_2$-C(O)- | —(CH$_2$)$_{12}$CH$_3$ | —C(O)(CH$_2$)$_{10}$CH$_3$ | —(CH$_2$)$_6$CH$_3$ |

Compounds of formula II, where a, b, R¹, R², R³, R⁴, R⁵, U, X, and W are as previously defined herein, can be prepared as shown in Scheme 4. Protected amino acids of formula XXXIX can be coupled to appropriately protected amino acids of formula XL to produce compounds of formula XLI. Removal of the t-butyl ester under acid conditions gives a compound of formula XLII, which can be subsequently coupled to a compound of formula XLIII to produce a compound of formula II.

Scheme 4.

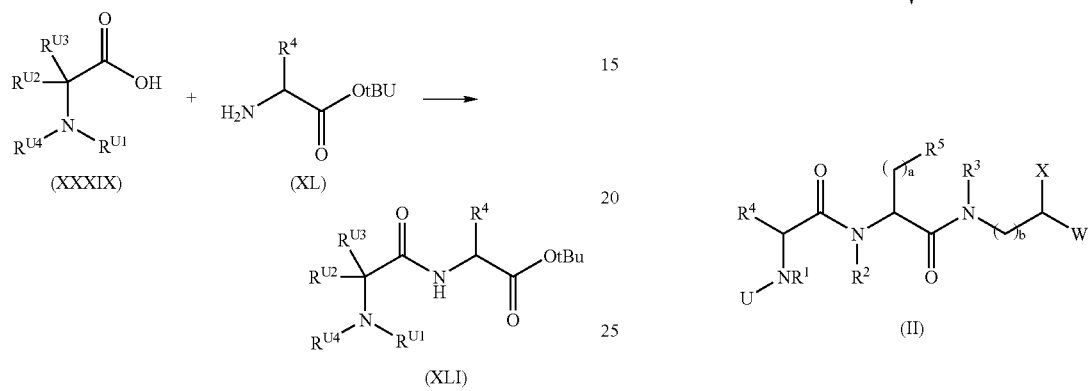

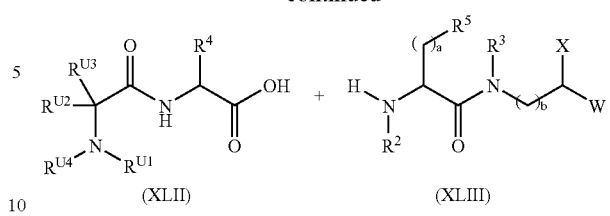

Exemplary compounds of formula II include ER811204 and ER811195, shown below.

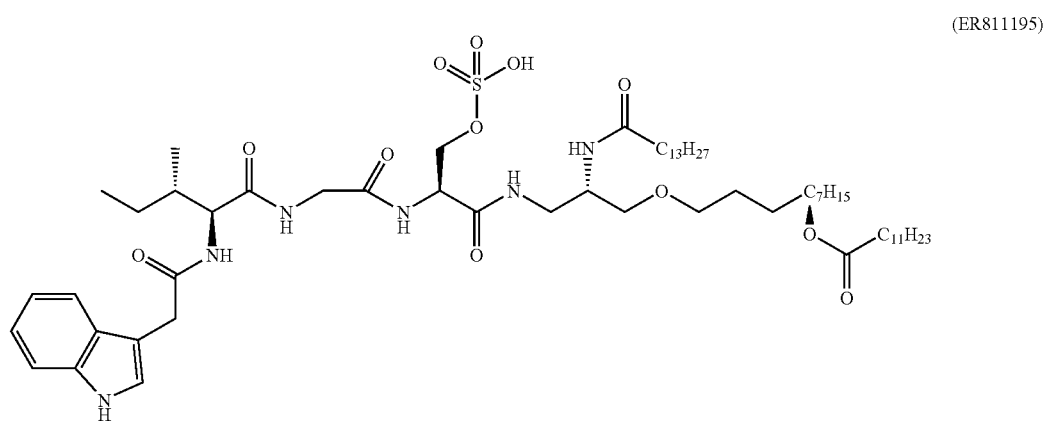

(ER811195)

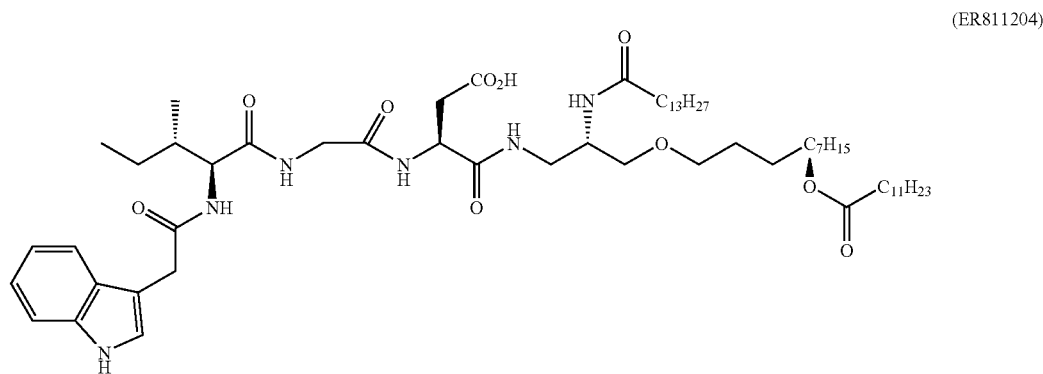

(ER811204)

Compounds of formula I or II in which W is —(CH$_2$)$_c$O(CH$_2$)$_d$CH(OR$^{W3}$)R$^{W4}$ can be prepared by methods analogous to those described in U.S. Pat. No. 6,551,600. In one non-limiting example, a compound of formula XLIV, where R$^{W3}$ is C$_{1-21}$ acyl and each of V and R$^{W4}$ is, independently, C$_{1-20}$ alkyl, is coupled to 2-(4-allyloxybenzyl)malonic acid, mono allyl ester, which can be prepared via the alkylation of the mono-allyl, mono-t-butyl ester of malonic acid with the allyl ether of 4-bromomethylphenol, followed by removal of the t-butyl protecting group under acidic conditions. The resulting compound XLV is produced after removal of the allyl protecting groups via treatment with a Pd(0) catalyst.

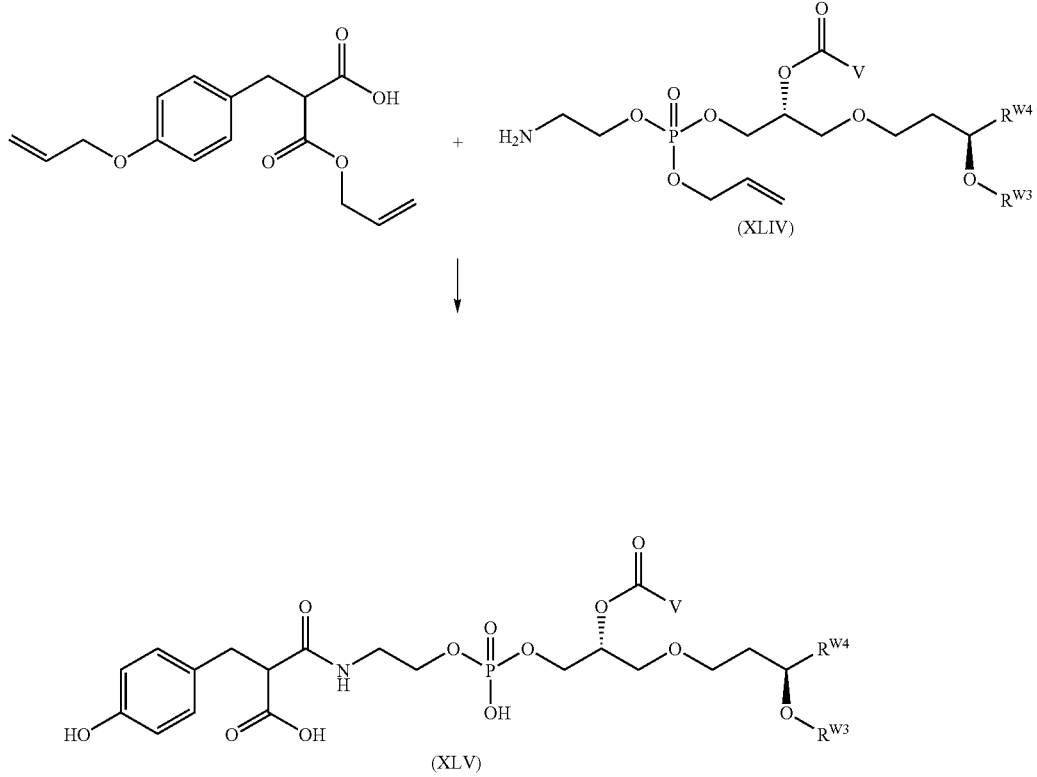

An example of a compound of formula XLV is ER808577.

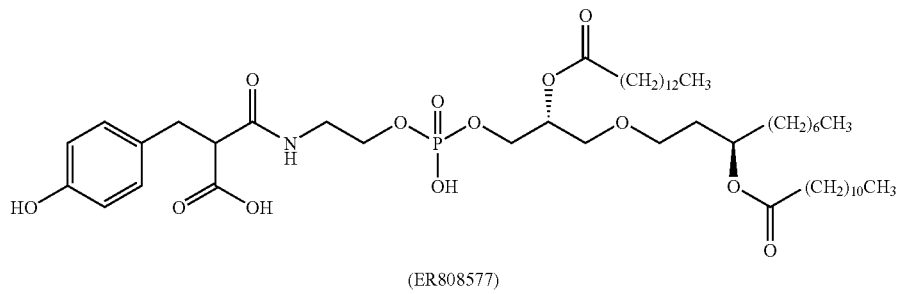

Compounds of formula I, where W is C(O)OR$^{W2}$, can be prepared by the coupling of protected serine analogs with alcohols using a carbodiimide, or another suitable coupling reagent, as exemplified in the reaction of N-Boc-O-benzyl-L-serine with a compound of formula XLVI to produce a compound of formula XLVII.

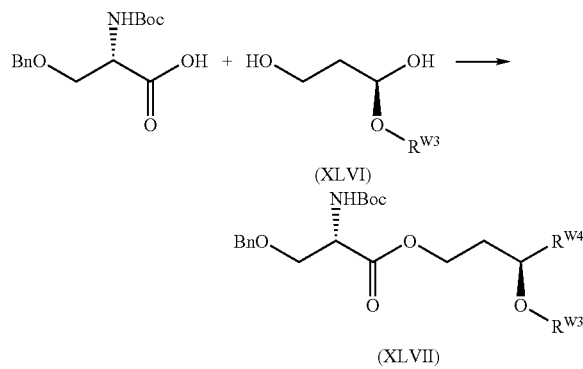

(XLVI)

(XLVII)

Selective removal of the Boc-protecting group under acidic conditions, followed by N-acylation and subsequent removal of the benzyl protecting group via hydrogenation gives a compound of formula XLVIII. Phosphorylation, oxidation, and deprotection, as previously described above, gives a compound of formula XLIX, which can be functionalized at the free amine position by acylation, reductive amination, or sulfonation to give, after removal of the allyl protecting group, a compound of formula L.

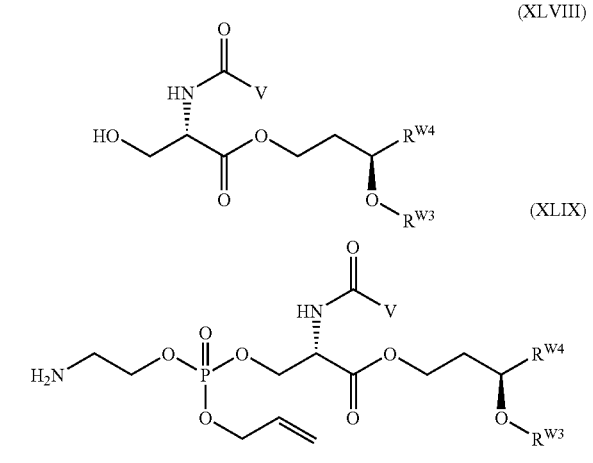

(XLVIII)

(XLIX)

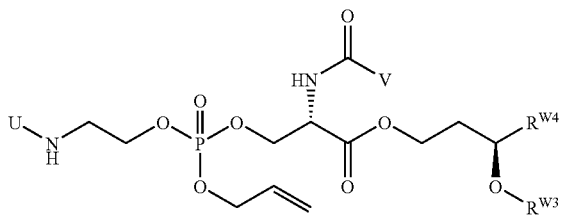

(L)

An example of a compound of formula L is ER808549

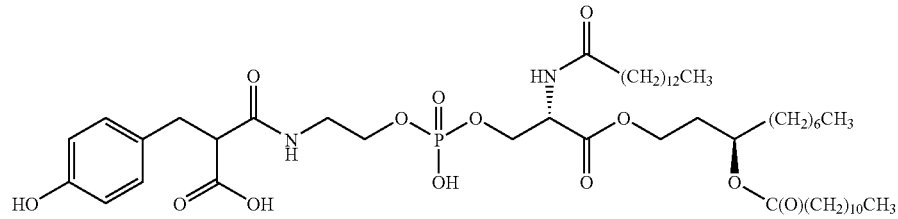

(ER808549)

Compounds of the invention can also incorporate peptide sequences. Useful intermediates for incorporating peptides into compounds of the invention are those that contain a carboxyl or amino group. Intermediates that contain an amino group can be reacted with the C-terminal carboxyl group of a protected peptide and intermediates that contain a carboxyl group can be reacted with the amine terminus of a protected peptide. A particularly useful intermediate is that of formula LI, shown below, where X and W are as previously defined herein.

(LI)

The peptide sequences can be synthesized by either solid or liquid phase methods described and referenced in standard textbooks, or by a combination of both methods. These methods are well known to those skilled in the art, (see, for example, Bodanszky, In "The Principles of Peptide Synthesis," Hafner, Rees, Trost, Lehn, Schleyer, Zahradnik, Eds., Springer-Verlag, Berlin, 1984; Stewart and Young, Solid Phase Peptide Synthesis, Pierce Chemical Co., Rockford, Ill., 1984).

All of the starting materials used in any of these methods are commercially available from chemical vendors such as Aldrich, Sigma, Nova Biochemicals, Bachem Biosciences, Advanced ChemTech, and the like, or may be readily synthesized by known procedures.

The reaction products are isolated and purified by conventional methods, typically by solvent extraction into a compatible solvent. The products may be further purified by column chromatography or other appropriate methods, including medium pressure or high pressure liquid chromatography.

During the synthesis of these compounds, the functional groups of the amino acid derivatives used in these methods are protected by blocking groups to prevent cross reaction during the coupling procedure. Examples of suitable blocking groups and their use are described in "The Peptides:

Analysis, Synthesis, Biology," Academic Press, Vol. 3 (Gross, E. & Meienhofer, J., Eds., 1981) and Vol. 9 (1987), the disclosures of which are incorporated herein by reference.

A particularly useful support for the synthesis of peptide sequences is 2-chlorotrityl resin. Peptide sequences prepared on chlorotrityl resin can be further reacted in an on-resin reaction with an intermediate used in the present invention that contains a carboxyl group, such as, for example, a compound of formula XLI. Alternatively, a peptide prepared on chlorotrityl resin can be removed from the resin in the protected state, followed by reaction of the carboxyl-terminus of the peptide with an intermediate of the invention that contains an amine and subsequent removal of any protecting groups used in the peptide synthesis. An example of a compound of the present invention that contains a peptide sequence is ER810625, shown below

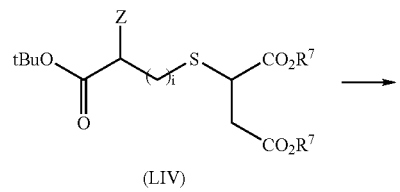
(LIV)

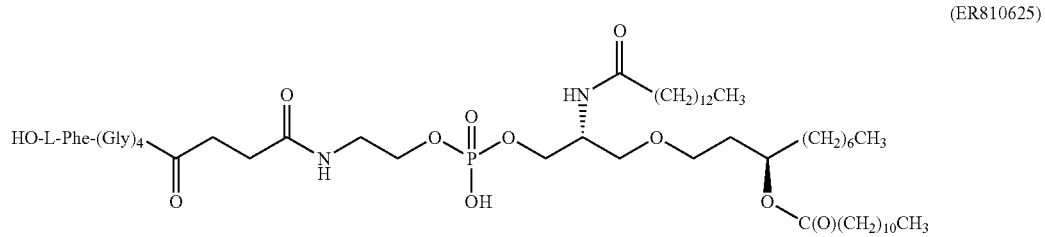
(ER810625)

Compounds of formula LII:

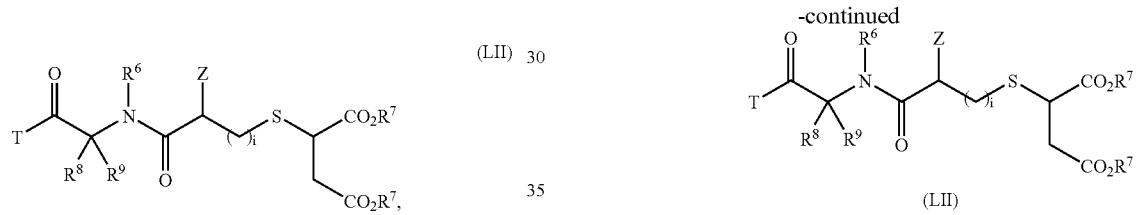
(LII)

where each of i, T, Z, $R^6$, $R^7$, $R^8$, and $R^9$ is as defined above, can be prepared from an appropriately protected amino acid which includes a sulfhydryl moiety as part of the side chain, such as, for example, cysteine or homocysteine. The sulfhydryl is reacted with an activated olefin to produce a compound of formula LIII. After the Fmoc-protected amine LIII is deprotected and manipulated in a manner analogous to that described above for the elaboration of the X group of compounds of formula I or II to give a compound of formula LIV, the carboxy terminus of a compound of formula LIV can be functionalized as described herein for the functionalization of other intermediates having a carboxyl group to produce a compound of formula LII.

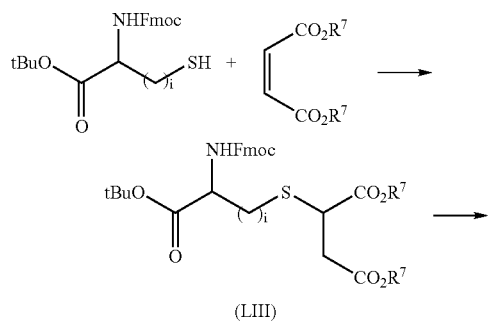
(LIII)

An example of a compound of formula Ia is compound ER810675

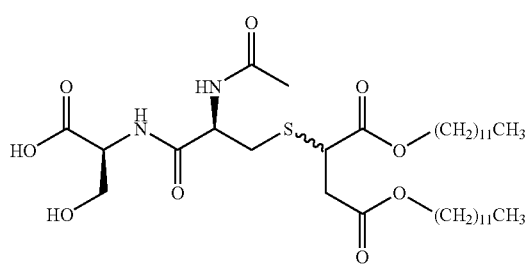
ER810675

Therapeutic Use of TLR2 Inhibitors

Agents that decrease or inhibit activation of TLR2 can be used to prevent or to treat any of a number diseases or conditions that are characterized by TLR2 activation. For example, the agents can be used to prevent or to treat inflammatory bowel disease (IBD), such as, for example, Crohn's disease or ulcerative colitis. Other diseases or conditions that can be prevented or treated using the methods of the invention include, for example, sepsis, periodontal disease, mucositis, acne, cardiovascular disease, chronic obstructive pulmonary disease, arthritis, cystic fibrosis, bacterial-induced infections, viral-induced infections, mycoplasma-associated diseases, post herpetic neuralgia, ischemia/reperfusion injury, asthma, stroke, brain injury, necrotizing enterocolitis, bed sores, leprosy, atopic dermatitis, psoriasis, trauma, neurodegenerative disease, amphotericin B-induced fever and nephritis, coronary artery bypass grafting, and atherosclerosis.

Dosage levels of active ingredients in the pharmaceutical compositions of the invention may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration. Doses are determined for each particular case using standard methods in accordance with factors unique to the patient, including age, weight, general state of health, and other factors that can influence the efficacy of the compound(s) of the invention.

It is not intended that the administration of a compound of the invention to a mammal, including humans, be limited to a particular mode of administration, dosage, or frequency of dosing. The present invention contemplates all modes of administration, including oral, intraperitoneal, intramuscular, intravenous, intraarticular, intralesional, subcutaneous, or any other route sufficient to provide a dose adequate to prevent or treat excess or undesired TLR2 activity. One or more compounds or the invention may be administered to a mammal in a single dose or multiple doses. When multiple doses are administered, the doses may be separated from one another by, for example, several hours, one day, one week, one month, or one year. It is to be understood that, for any particular subject, specific dosage regimes should be adjusted over time according to the individual need and the professional judgment of the person administering or supervising the administration of a pharmaceutical composition that includes a compound of the invention.

For clinical applications, a compound of the present invention may generally be administered intravenously, subcutaneously, intramuscularly, colonically, nasally, intraperitoneally, rectally, buccally, or orally. Compositions containing at least one compound of the invention that is suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in *Remington: The Science and Practice of Pharmacy* (20th ed.), ed. A. R. Gennaro, Lippincott Williams & Wilkins, 2000, Philadelphia, and *Encyclopedia of Pharmaceutical Technology*, eds. J. Swarbrick and J. C. Boylan, 1988-1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers in order to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents that facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the invention in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the invention are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing a compound of the invention may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of formula I or II.

Dosage formulations of a compound of the invention to be used for therapeutic administration must be sterile. Sterility is readily accomplished by filtration through sterile membranes (e.g., 0.2 micron membranes) or by other conventional methods. Formulations typically are stored in lyophilized form or as an aqueous solution. The pH of the compositions of this invention is typically between 3 and 11, more desirably between 5 and 9, and most desirably between 7 and 8, inclusive. While a desirable route of administration is by injection such as intravenously (bolus and/or infusion), other methods of administration may be used. For example, compositions may be administered subcutaneously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches. A compound of the invention is desirably incorporated into shaped articles such as implants, including but not limited to valves, stents, tubing, and prostheses, which may employ inert materials such as synthetic polymers or silicones, (e.g., Silastic, silicone rubber, or other commercially available polymers). Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, a TLR2 inhibitor of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

A compound of the invention may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines. A compound of the invention may also be delivered using antibodies, antibody fragments, growth factors, hormones, or other targeting moieties to which the compound molecules are coupled (e.g., see Remington: The Science and Practice of Pharmacy, vide supra), including in vivo conjugation to blood components of a compound of the formula I or II, as described herein.

Identification of TLR2 Inhibitors

Pharmaceutical agents that can be used in the therapeutic methods of the invention can be identified in screening methods. For example, cell-based screening methods can be used, in which cells expressing TLR2 are contacted with a candidate agent and the impact of the agent on the activation of TLR2 in the cells is determined. In one example of such a method, the effect of an agent on the activation of TLR2 by a known ligand (e.g., a lipopeptide, such as Pam3Cys-SKKKK (see below)) is determined. Agents that are found to decrease or to block activation of the receptor by the ligand can then be considered for further analysis and/or for use as TLR2 inhibitors in therapeutic methods. Activation of TLR2 in these methods can be measured using, for example, a reporter system. For example, cells used in the screening assay can include a reporter gene (e.g., luciferase) that is under the control of a promoter (e.g., the ELAM promoter) that is inducible by a signaling pathway triggered by TLR2 activation (e.g., a signaling pathway that induces expression of NF-KB). Additional details of an example of such a method are provided below.

In addition to cell-based methods, candidate agents can be tested in animal model systems. This may be desirable, for example, if an agent has been found to have antagonist activity in a cell-based assay or to bind to TLR2 in an in vitro assay (see below). For example, in animal studies, test agents can be administered to an animal model concurrently with a molecule known to activate TLR2 (e.g., lipopeptide), and the impact of the agent on a response in the animal that is normally triggered by activation of the receptor (e.g., cytokine induction) can be determined. Further, in vitro methods can be used. For example, a candidate compound can be assayed for whether it binds to TLR2 or a fragment of the receptor that includes at least a portion of the ligand binding site. Such assays can be carried out using, for example, columns or beads to which the receptor or fragment is bound.

In addition to the methods described above, additional TLR2 antagonists can be identified in methods in which candidate compounds are compared for TLR2 antagonist activity with any of the TLR2 antagonists described herein. These methods can involve the use of in vitro or in vivo methods, such as those described herein (e.g., see above and Example 8). Further, in addition to being compared for TLR2 antagonist activity, the candidate compounds can be compared with TLR2 antagonists with respect to specificity for TLR2 versus other receptors (e.g., TLR4), as described below. Candidate compounds identified as having TLR2 antagonist activity that is, for example, similar to or greater than the activity of the antagonists described herein (and/or with similar or greater levels of specificity for TLR2 versus TLR4) in these assays can be tested further, for example, in appropriate animal model assays for any of the diseases or conditions described herein, as well as in human clinical studies. A candidate compound having TLR2 antagonist activity is one that, for example, is found to have an $IC_{50}$ for TLR2 in an assay such as that described in Example 8 of, e.g., less than 30 μM (e.g., less than 25, 20, 15, 10, 5, 1, or 0.5 μM).

Also included in the invention are compounds that are selective for TLR2 over TLR4, as well as compounds that are dual antagonists (i.e., antagonists of both TLR2 and TLR4). A compound that is selective for TLR2 over TLR4 is one that has, for example, an IC50 value in a TLR2 antagonist assay, such as is described herein, that is less than that found in a TLR4 antagonist assay, such as is described herein. For example, the IC50 in the TLR2 assay can be at least 5, 10, 25, or 50-fold less than the value for the same compound tested in the TLR4 assay. Compounds that are dual antagonists are those that have, for example, IC50 values that are within a 5-fold range of one another using, e.g., the assays described herein. Thus, dual antagonists include those that have activities that are 1:5-5:1 with respect to one another (e.g., 1:4, 1:3, 1:2, 1:1, 2:1, 3:1, and 4:1). The invention also includes the use of TLR2 antagonists such as those described herein in the study of physiological and molecular pathways involved in or affected by TLR2 activation (or inactivation).

Agents that can be screened using the methods of the invention include, for example, compounds that are present in compound libraries (e.g., random libraries), as well as analogs of known TLR2 ligands (e.g., lipopeptides) that are modified to prevent rather than activate TLR2. Further, peptides that correspond to the binding site of TLR2 for its ligands, which can competitively inhibit ligand binding to the binding site, can be tested. Further, antibodies or antibody fragments to the ligand or the ligand binding site of the receptor can be screened.

The following non-limiting examples are provided to further describe various aspects and embodiments of the present invention.

EXAMPLES

Example 1

Preparation of ER811133

Step 1. To a solution of 1-pentadecene (23.0 mL, 84.7 mmol) in DCM (200 mL) at 0° C. was added sodium bicarbonate (704 mg, 8.3 mmol) and mCPBA (58.48 g, 338.9 mmol) portion wise. The reaction mixture was allowed to warm up to RT. After stirring at RT overnight, saturated sodium sulfite solution (500 mL) was added to the reaction mixture. The organic layer was dried over sodium sulfate and concentrated in vacuo. Purification of the residue by silica gel chromatography (10% EA/hexane) gave compound 1 (19.10 g, 96% yield).

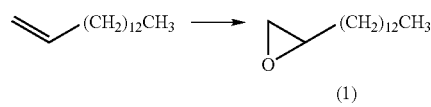

(1)

Step 2. To a solution of compound 1 (19.1 g, 84.4 mmol) in 90% ethanol (200 mL) at RT was added potassium cyanide (15.38 g, 236.2 mmol). After stirring at RT for 20 hours, the reaction mixture was filtered through sodium sulfate. Purification by silica gel chromatography (30% EA/hexane) gave compound 2 (18.46 g, 86% yield).

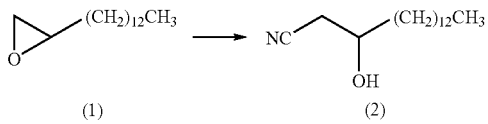

Step 3. To a solution of compound 2 (18.46 g, 72.84 mmol) in DMF (100.0 mL) at RT was added imidazole (9.9 g, 145.7 mmol) and tert-butyldiphenylsilyl chloride (TBDPSCl) (28.4 mL, 109.3=mol). The reaction was monitored by TLC (30% EA/hexane) until all the starting material was consumed. Purification by silica gel chromatography (20% EA/hexane) gave compound 3 (34.84 g, 97% yield).

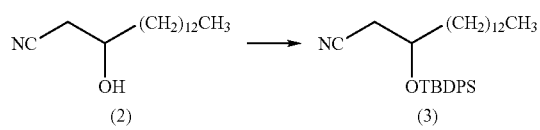

Step 4. To a solution of Raney-Ni (3.0 mL slurry) in 2.0 M $NH_3$/MeOH (100 mL) was compound 3 (5.04 g, 10.2 mmol) and the reaction mixture was hydrogenated at 50 psi for 20 hours. The reaction mixture was filtered through Celite and washed with MeOH to give compound 4 (4.81 g, 95%).

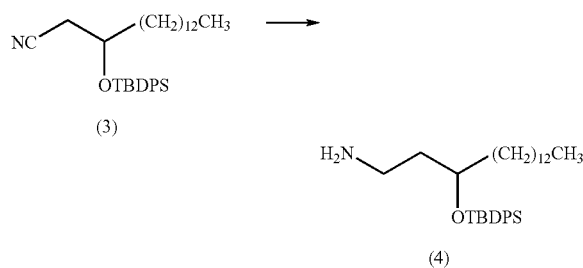

Step 5. To a solution of compound 4 (4.81 g, 9.7 mmol) in DCM (50 mL) was added N-Fmoc-L-serine (4.76 g, 14.55 mmol) and EDC (3.72 g, 19.4 mmol) at −5° C. The reaction mixture was allowed to warm up to RT and stirred for 3 hours. Purification by silica gel chromatography using 10-50% EA/hexane gave compound 5 (6.26 g, 80%) as waxy solid.

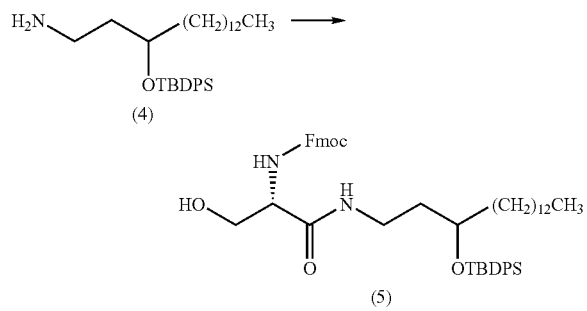

Step 6. To make phosphorylating reagent compound 6, to a solution of distilled diisopropylamine (9.0 mL) in methylene chloride was added tetrazole (4.51 g) at room temperature followed by stirring for 1.5 hours. Allyl phosphorodiamidite (10) (20.5 mL) was added dropwise at a 6.5 mL/hour rate followed by stirring for an additional 3 hours. N-Boc-2-aminoethanol (10.36 g) in methylene chloride (50 mL) was added to the above reaction mixture dropwise at a 8.4 mL/hour rate followed by stirring for an additional 18 hours. The white suspension was filtered through Celite 545 with two 20 mL washings with methylene chloride. The filtrate was concentrated followed by the suspension and filtering of the residue with hexanes (200 mL). The resulting hexanes filtrate was concentrated to dry and azeotroped with 2,10-mL portions of toluene to provide the crude product 6 (21.54 g) as an oil.

To a solution of compound 5 (6.26 g, 7.77 mmol) in DCM (70 mL) at RT was added pyridinium trifluoroacetate (3.0 g, 15.55 mmol). The above reaction solution was cooled to −20° C. To the reaction solution was added compound 6 (4.8 g, 14.0 mmol) using a syringe. The reaction was kept at −10 to −20° C. and monitored by TLC (30% acetone/hexane) until compound 5 was consumed. To the reaction mixture was added hydrogen peroxide (30%, 1.8 mL). The reaction mixture was allowed to warm up slowly and stirred for 30 minutes at RT. To the solution was added sodium thiosulfate (2.0 g) in water (20 mL). Compound 7 (8.7 g) was isolated after aqueous workup and HPLC on a Biotage column (10-30% acetone/hexane).

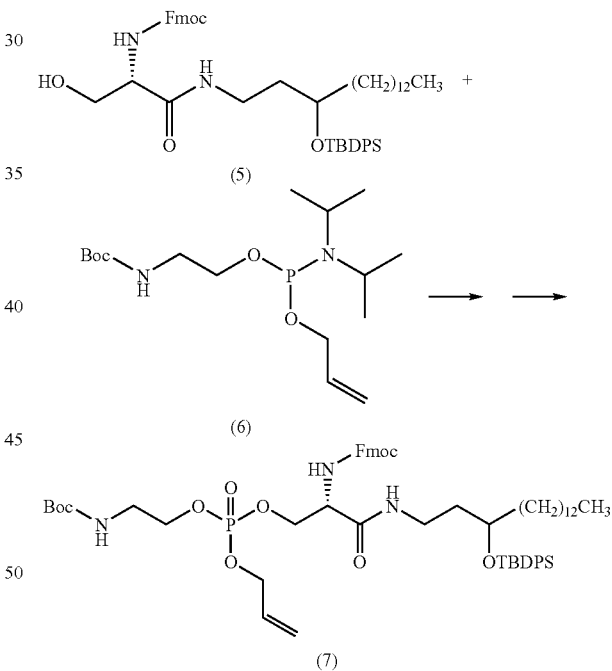

Step 7. To a solution of compound 7 (2-83 g, 2.645 mmol) in DCM (12.0 mL) was added piperidine (3.0 mL, 10.1 mmol) at −5° C. The mixture was stirred at −5° C. for 3 0 minutes, followed by warming to RT and monitoring by TLC. When the starting material was consumed, the reaction mixture was concentrated to give crude amine. To a solution of the crude amine in DCM (10 mL) was added lauric acid (1.06 g, 5.29 mmol) and EDC (1.01 g, 5.29 mmol) at 0° C. After stirring at 0° C. for 110 minutes, the reaction mixture was allowed to warm up to RT and stirred at RT overnight. Aqueous workup, followed by concentration of the organics and purification by chromatography gave compound 8 (2.45 g, 90% yield).

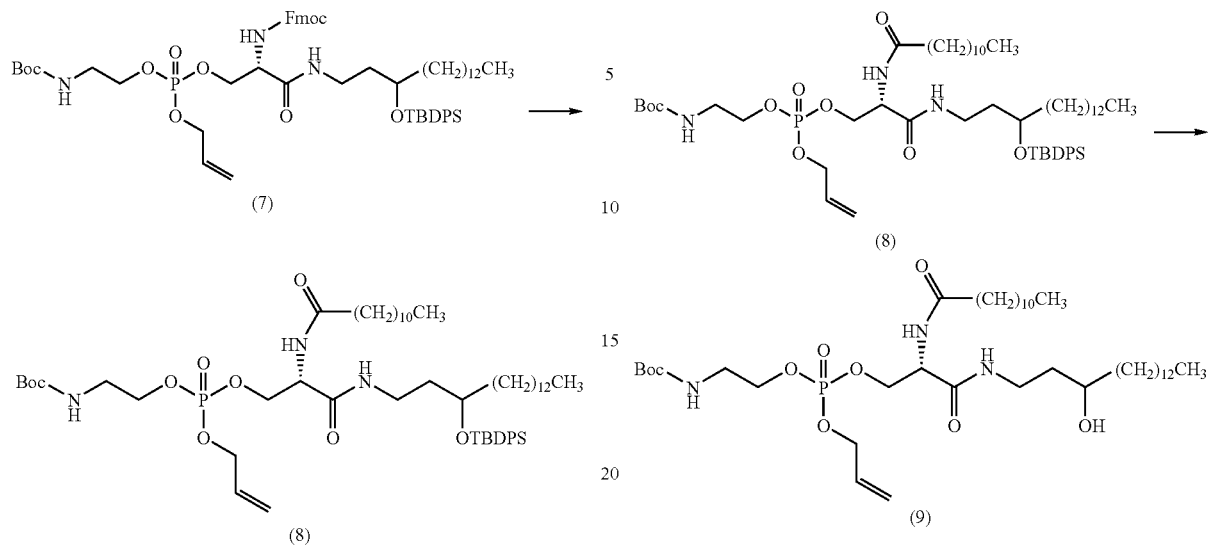

Step 8. To a solution of compound 8 (1.5 g, 0.473 mmol) in THF (10 mL) at RT was added acetic acid (0.17 mL, 2.92 mmol) and tetrabutylammonium fluoride (TBAF) (0.763 g, 2.92 mmol). After stirring at RT for 70 hours, the reaction mixture was diluted with water and extracted with EA. The combined organic solution was washed with saturated sodium bicarbonate, dried and concentrated. Purification by HPLC on a Biotage column with acetone/hexane gave product compound 9 (0.937 g, 81% yield).

Step 9. To compound 9 (138 mg, 0.175 mmol) was added 4.0 M HCl/dioxane (2.0 mL) and the mixture stirred for 2 hours at RT. The reaction mixture was concentrated and dried azeotropically with toluene to give crude amine. To a solution of the crude amine in DCM (5.0 mL) at 0° C. was added N-(3-indolacetyl)-L-isoleucine (55.4 mg, 0.192 mmol), HBTU (79.5 mg, 0.21 mmol) and DIPEA (90.3 mg, 0.70 mmol). The reaction was allowed to warm to RT and stirred overnight. The reaction mixture was loaded onto a 25 mm Biotage column and purified by HPLC, eluting with 10, 20, 30, 40, and 50% acetone/hexane to give compound 10 (72.0 mg, 43% yield).

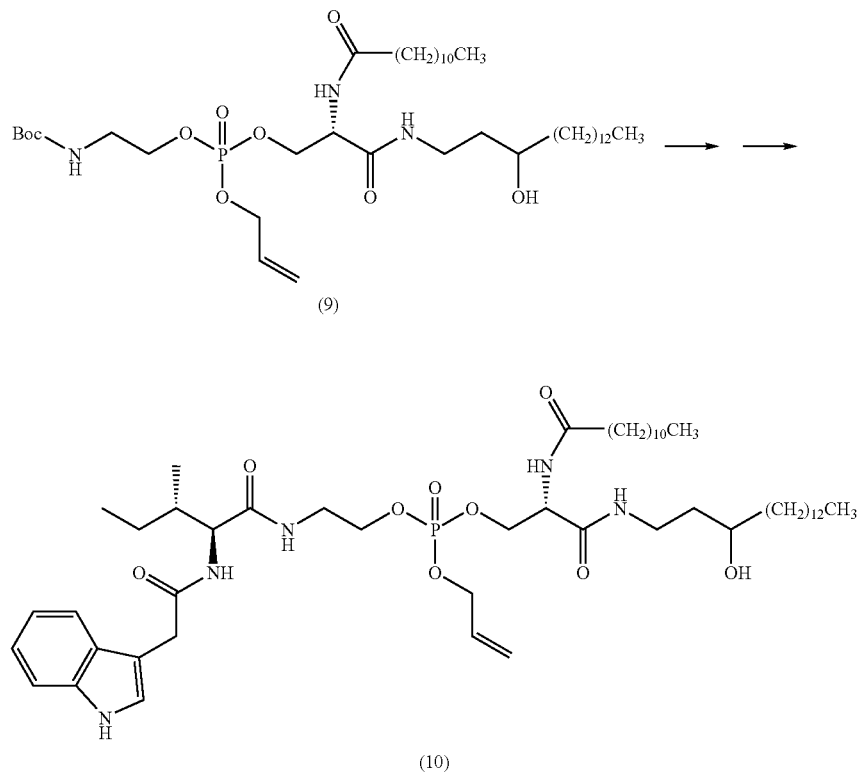

Step 10. To a solution of compound 10 (25.3 mg, 0.026 mmol) in THF (1.0 mL) was added phenylsilane (29 μL, 0.237 mmol), triphenylphosphine (12.4 mg, 0.047 mmol) and tetrakis(triphenylphosphine)palladium(0) (0.006 mg, 0.005 mmol) at RT. After stirring at RT for 30 minutes, the crude mixture was loaded onto 0.5 millimeter preparative TLC plate and eluted with 1:1 Magic (60:35:2:3 CHCl$_3$/MeOH/AcOH/H$_2$O)/DCM to give ER811133 (18.3 mg, 75%).

dinium trifluoroacetate (12.26 g, 63.48 mmol). The reaction mixture was cooled to −20° C. and compound 6 (17.60 g, 50.51 mmol) was added. After 2 hours, 30% hydrogen peroxide (14.5 mL, 140.3 mmol) was added and the reaction was allowed to warm to RT. To the reaction mixture was added a solution of sodium thiosulfate (17.2 g) in water (215 mL). Aqueous work-up and column chromatography gave compound 12 (25.37 g, 100% yield).

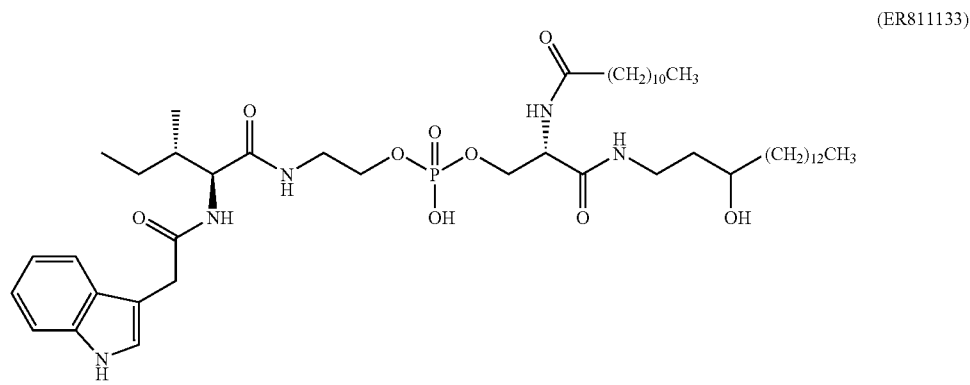

(ER811133)

Example 2

Preparation of ER811212

Step 1. To a solution of Fmoc-Ser-OH (25.2 g, 77.0 mmol) in dichloromethane (350 mL) at RT was added TBDPS protected propanolamine hydrochloride (20.0 g, 51.75 mmol) followed by triethylamine (14.5 mL, 104.1 mmol) and 1-[3-(dimethylamino)propyl]-3-ethylcarbodiimide hydrochloride (EDC, 19.85 g, 103.5 mmol). Stirring overnight followed by aqueous work-up and column chromatography gave compound 11 (10.38 g, 32% yield).

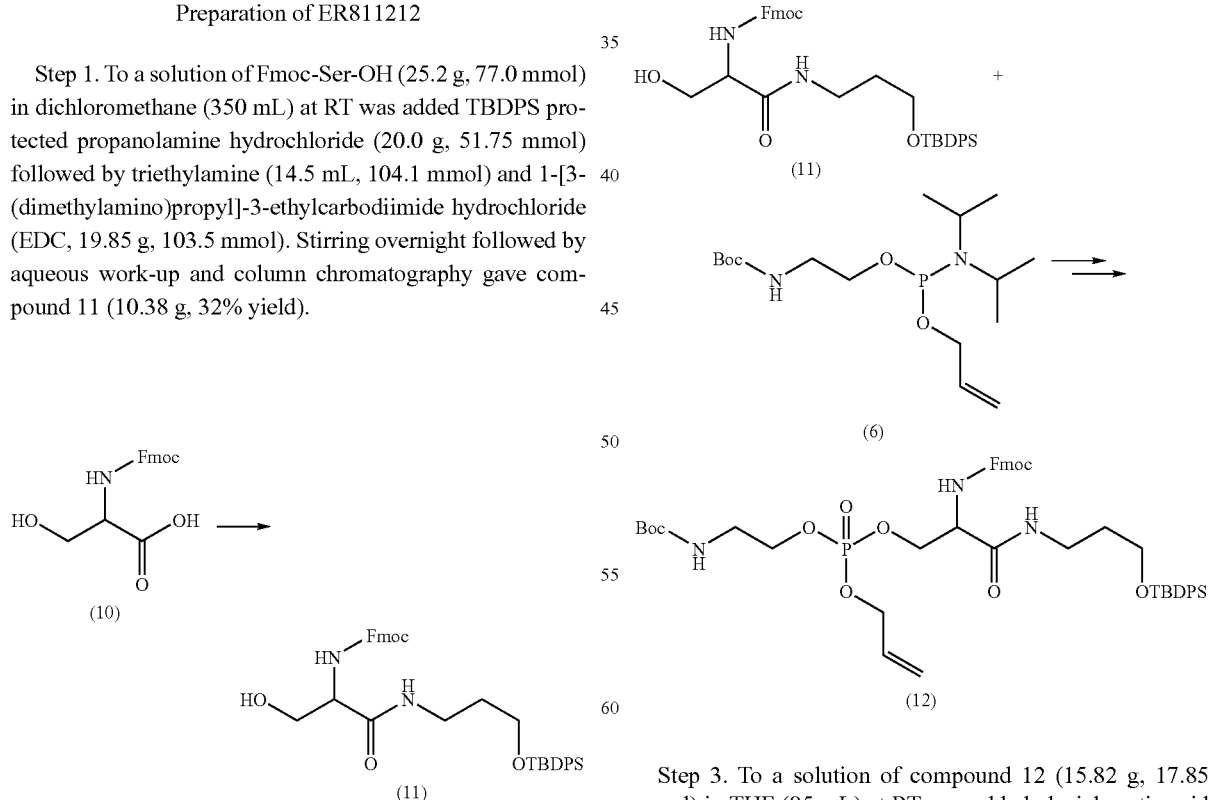

Step 2. To a solution of compound 11 (17.83 g, 28.63 mmol) in dichloromethane (400 mL) at RT was added pyri- Step 3. To a solution of compound 12 (15.82 g, 17.85 mmol) in THF (85 mL) at RT was added glacial acetic acid (2.1 mL, 36.68 mmol) followed by TBAF (9.35 g, 35.8 mmol). After stirring for 8 hours, aqueous work-up and column chromatography gave compound 13 (3.65 g, 31% yield).

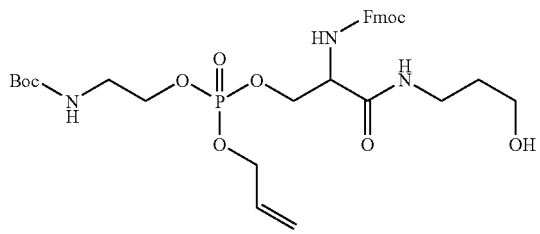
(13)

Step 4. To compound 13 (3.65 g, 5.64 mmol) at RT was added 4M HCl in dioxane (21.5 mL, 86.1 mmol). After 20 minutes, solvent was evaporated to give compound 14 (3.09 g, 93% yield).

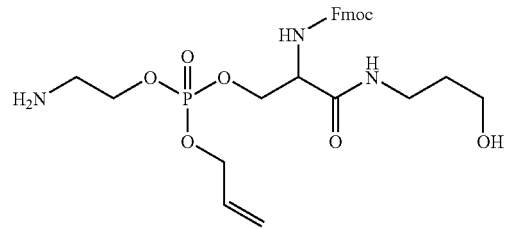
(14)

Step 5. To a solution of compound 14 (3.30 g, 5.64 mmol) in dichloromethane (35 mL) at RT was added N-(3-Indolylacetyl)-L-isoleucine (1.80 g, 6.24 mmol) followed by DIEA (2.2 mL, 12.69 mmol) and HBTU (2.59 g, 6.83 mmol). After 2 hours, aqueous workup and chromatography gave compound 15 (3.74 g, 81% yield).

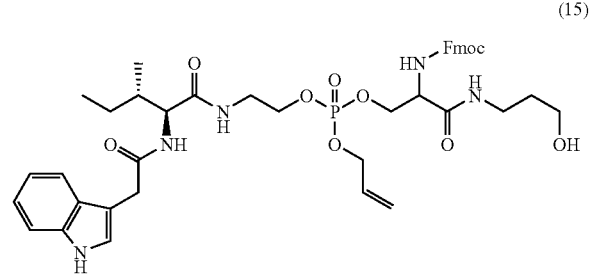
(15)

Step 6. To a solution of compound 15 (204 mg, 0.25 mmol) in dichloromethane (1.5 mL) at RT was added palmitic acid (125 mg, 0.49 mmol) followed by EDC (95 mg, 0.495 mmol) and DMAP (8.2 mg, 0.067 mmol). After stirring overnight at RT, aqueous work-up and chromatography gave compound 16 (198 mg, 75% yield).

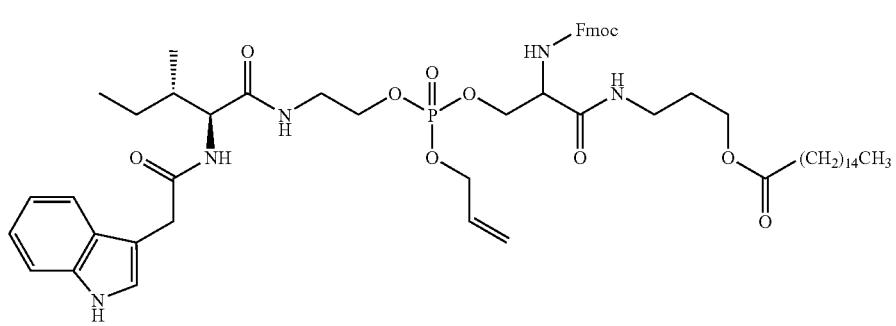
(16)

Step 7. To compound 16 (65 mg, 0.061 mmol) at RT was added a solution of 4.0 M piperidine in DMF (0.38 mL, 1.54 mmol). After 20 minutes, the solvent was evaporated to give compound 17 (50 mg, 100% yield).

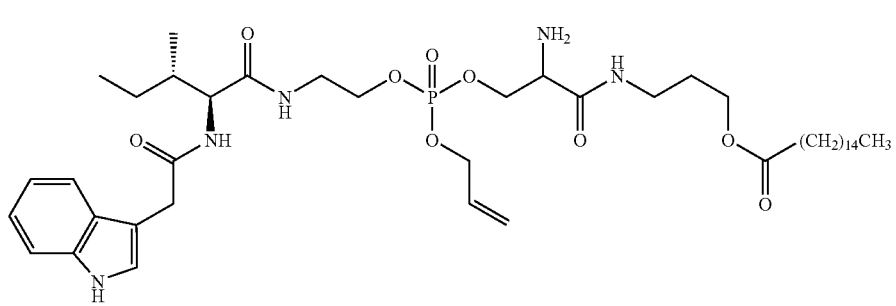
(17)

Step 8. To a solution of compound 17 (51.1 mg, 0.059 mmol) in dichloromethane (0.48 mL) at RT was added lauric acid (17.2 mg, 0.086 mmol) followed by DIEA (24 μL, 0.138 mmol) and HBTU (30.7 mg, 0.081 mmol). After stirring overnight, the solvent was evaporated. Purification by column chromatography gave compound 18 (44.8 mg, 73% yield).

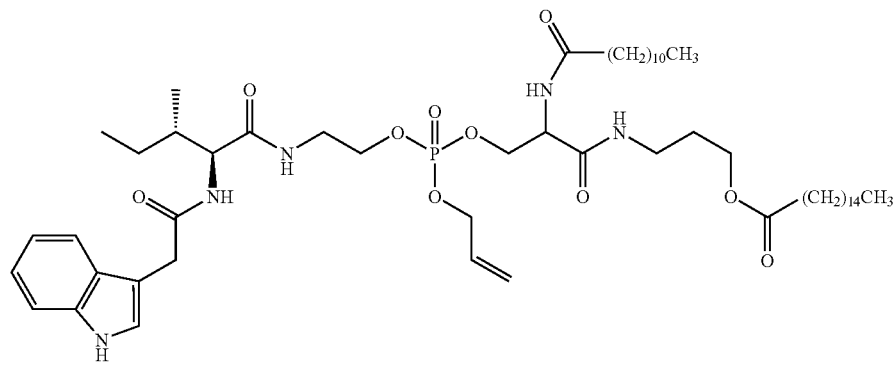

(18)

Step 9. To a solution of compound 18 (45 mg, 0.044 mmol) in THF (0.63 mL) at RT was added a 0.10 M solution of n-butylamine (0.450 mL, 0.045 mmol) followed by palladium tetrakistriphenylphosphine (2.9 mg, 0.0025 mmol). After 2 hours, the solvent was evaporated. Purification by column chromatography gave compound 19 (ER811212, 22.9 mg, 59% yield).

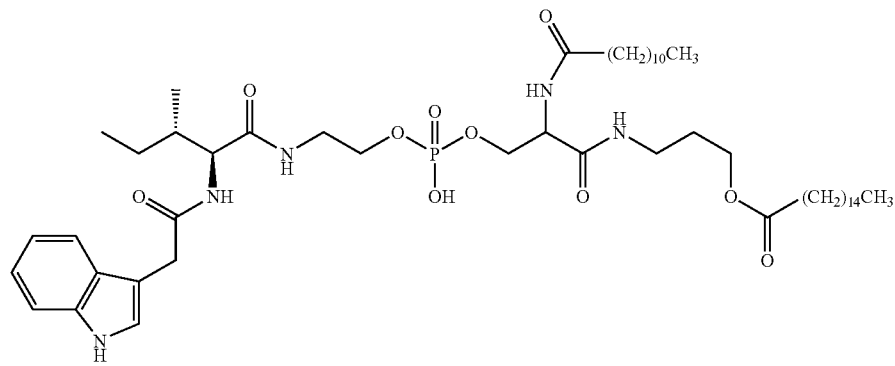

(ER811212)

Example 3

Preparation of ER811230

Step 1. To a solution of Fmoc-Glycinol (104.4 mg, 0.3685 mmol) in dichloromethane (5 mL) at RT was added pyridinium trifluoroacetate (155.1 mg, 0.8031 mmol). The reaction mixture was cooled to −20° C. and Boc-phosphorylating reagent compound 6 (212.1 mg, 1.652 mmol) was added. After 2 hours, 30% hydrogen peroxide (0.170 mL, 1.665 mmol) was added and the reaction was allowed to warm to RT. To the reaction mixture was added a solution of sodium thiosulfate (240 mg in 3.2 mL water). Aqueous work-up and column chromatography gave compound 20 (150 mg, 74% yield).

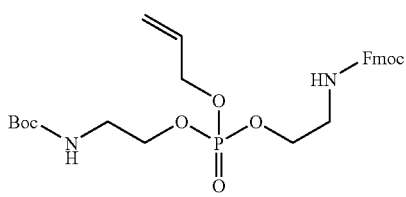
(20)

Step 2. To compound 20 (150 mg, 0.27 mmol) at RT was added 4 M HCl in dioxane (1.0 mL). After 20 minutes, solvent was evaporated to give compound 21 (132 mg, 100% yield).

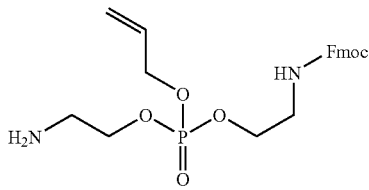
(21)

Step 3. To compound 21 (132 mg, 0.27 mmol) in dichloromethane (1.5 mL) at RT was added N-(3-indolylacetyl)-L-isoleucine (85 mg, 0.29 mmol), followed by DIEA (0.1 mL, 0.57 mmol) and HBTU (117 mg, 0.31 mmol). After stirring for 2 hours at RT, aqueous workup and chromatography gave compound 22 (141 mg, 71% yield).

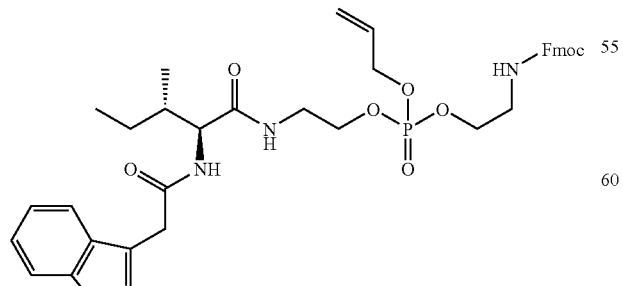
(22)

Step 4. To compound 22 (32 mg, 0.045 mmol) at RT was added a solution of 4.0 M piperidine in DMF (0.260 mL). After 20 minutes, the solvent was evaporated to give compound 23 (21 mg, 94%).

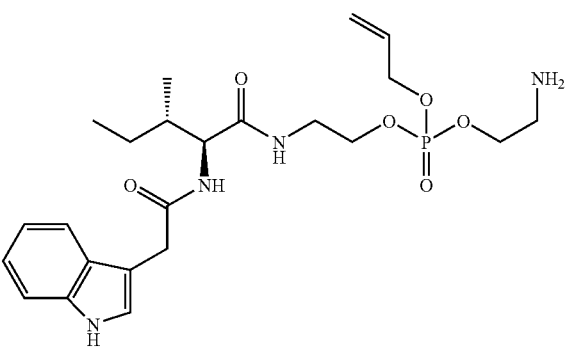
(23)

Step 5. To a solution of compound 23 (21 mg, 0.04 mmol) in dichloromethane (0.25 mL) at RT was added palmitic acid (13 mg, 0.05 mmol) followed by DIEA (16 μL, 0.09 mmol) and HBTU (20 mg, 0.054 mmol). After stirring overnight, the solvent was evaporated. Purification by column chromatography gave compound 24 (19 mg, 61% yield).

(24)

Step 6. To a solution of compound 24 (19 mg, 0.026 mmol) in THF (0.4 mL) at RT was added a 0.1 M solution of n-butylamine (0.26 mL, 0.026 mmol) followed by palladium tetrakistriphenylphosphine (1.7 mg, 0.0015 mmol). After 2 hours, the solvent was evaporated. Purification by column chromatography gave compound ER811230 (13.0 mg, 73% yield).

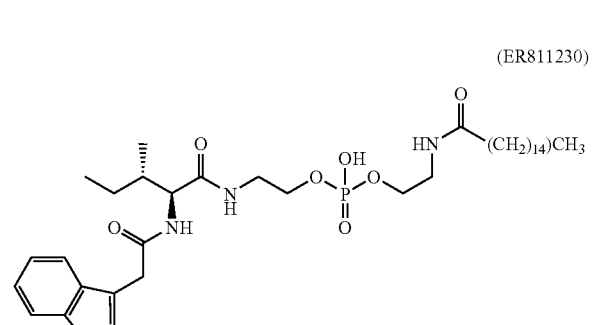
(ER811230)

Example 4

Preparation of ER8 11261

Step 1. To a solution of (S)-(+)-2,2-dimethyl-1,3-dioxolane-4-methanol (1.36 g, 10.3 mmol) in dichloromethane (5 mL) was added triethylamine (4.30 mL, 30.9 mmol). The mixture was cooled with an ice/water bath and methanesulfonyl chloride (2.40 mL, 30.9 mmol) was added. The reaction was quenched by addition of saturated NaHCO₃ solution (aqueous) after stirring overnight. The aqueous phase was extracted with one portion of dichloromethane; combined organic phase was washed with water, dried with anhydrous sodium sulphate and concentrated. Crude compound 25 was used without purification for next step.

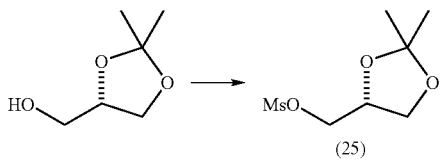

(25)

Step 2. To a solution compound 25 from step 1 in DMF (10 mL) was added a solution of NaN₃ (2.0 g, 31 mmol) in water (5 mL) and the reaction mixture was heated to 80° C. After stirring 18 hours, reaction mixture was allowed to cool to RT and a brine solution was added. The mixture was extracted with three portions of diethyl ether and organic phase was concentrated to ½ volume by rotary evaporation, washed with two portions of water, followed by brine, dried with anhydrous sodium sulphate and concentrated. Crude compound 26 (1.84 g) was used without purification for the next step.

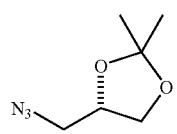

(26)

Step 4. A solution of crude compound 26 (1.84 g), triphenylphosphine (3.51 g, 13.4 mmol) in THF (20 mL) and water (0.80 mL) was stirred at RT overnight. The solvent was evaporated under reduced pressure and hexane was added to the residue. The resulting solid was removed by filtration and this process of adding hexane and filtration was repeated several times. The crude produce was passed through a short column of silica gel (100% EA, 30% isopropyl alcohol/EA) to afford compound 27 (279 mg).

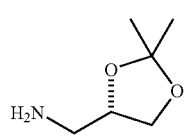

(27)

Step 5. A mixture containing compound 27 (268 mg, 2.04 mmol), EDC (589 mg, 3.07 mmol), DMAP (50 mg, 0.407 mmol), and O-benzyl-N-acetyl-D-serine (725 mg, 3.07 mmol) in dichloromethane (2 mL) was stirred at RT. After stirring overnight, the reaction mixture was concentrated and purification by flash chromatography gave compound 28 (359 mg).

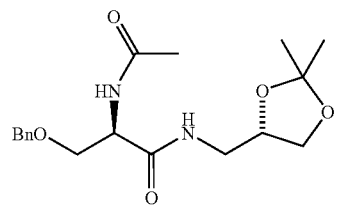

(28)

Step 6. A solution of acetic acid in water (3.50 mL, 5:1) was added to compound 28 (343 mg, 0.979 mmol). After stirring at RT overnight, the reaction was heated to 40° C. After 1.5 hours, the reaction mixture was concentrated and azeotroped with toluene. Purification by flash chromatography afforded compound 29 (289 mg, 95%).

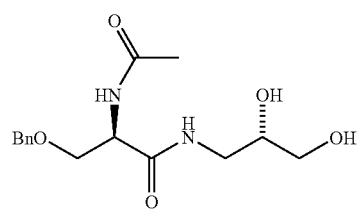

(29)

Step 7. A mixture of compound 29 (265 mg, 0.854 mmol), palmitic acid (679 mg, 2.65 mmol), EDC (507 mg, 2.65 mmol), and DMAP (32.5 mg, 0.265 mmol) was stirred at RT for 18 hours. Aqueous work-up and chromatography gave compound 30 (591 mg).

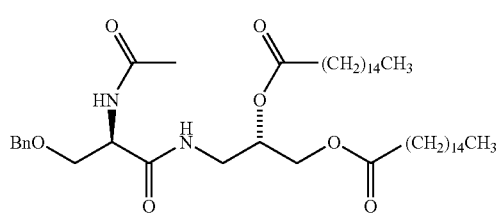

(30)

Step 8. To a flask containing compound 30 in ethyl acetate (30 mL) was added Pearlman's catalyst and the reaction mixture was stirred under a hydrogen atmosphere (using hydrogen filled balloon). After 2 hours the reaction mixture was filtered through Celite and concentrated to give compound 31 (344 mg). The crude product was used in the next reaction without purification.

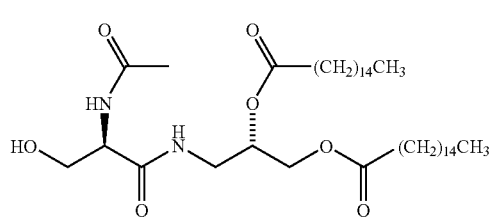

(31)

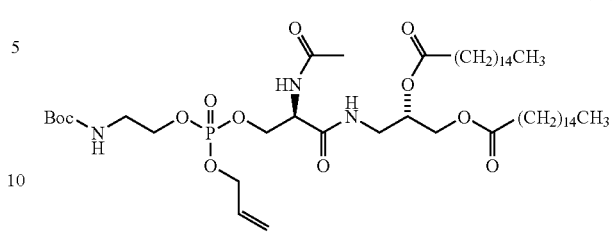

(32)

Step 9. To a solution of compound 31 (51.7 mg, 0.0742 mmol) in DCM (0.7 mL) at RT was added pyridinium trifluoroacetate (31.5 mg, 0.163 mmol). The above reaction solution was cooled to −20° C. To the reaction solution was added phosphorylating reagent compound 6 (46.0 mg, 0.131 mmol). The reaction was kept at −10 to −20° C. and monitored by TLC (30% acetone/hexane) until compound 31 was consumed. To the reaction mixture was added hydrogen peroxide (30%, 18 μL). The reaction mixture was allowed to warm up slowly and stirred for 30 minutes at RT. After the addition of sodium thiosulfate (20 mg), compound 32 was isolated after aqueous workup and chromatography.

Step 10. To compound 32 (42.3 mg, 0.044 mmol) was added 4.0 M HCl/dioxane (132 μL) and the mixture stirred for 2 hours at RT. The reaction mixture was concentrated and dried azeotropically with toluene to give crude amine. To a solution of the crude amine in DCM (200 μL) at 0° C. was added N-(3-(5-benzyloxy)indolacetyl)-L-isoleucine (20.0 mg, 0.0485 mmol), HBTU (22.0 mg, 0.0582 mmol) and DIPEA (31.0 μL, 0.176 mmol). The reaction was allowed to warm to RT and stirred overnight. Aqueous workup and chromatography gave compound 33 (72.0 mg, 43% yield).

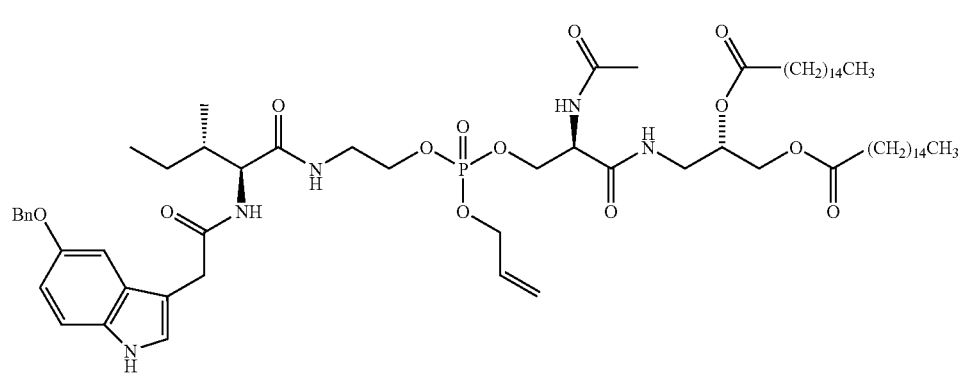

(33)

Step 11. To a solution of compound 33 (25.3 mg, 0.026 mmol) (10.2 mg, 0.00825 mmol) in THF (300 μL) was added phenylsilane (10 μL, 0.08 mmol), triphenylphosphine (4.1 mg, 0.015 mmol) and tetrakis(triphenylphosphine)palladium (0) (0.002 mg, 0.0015 mmol) at RT. After stirring at RT for 30 minutes, the crude mixture was loaded onto 0.5 millimeter preparative TLC plate and eluted with 1:1 Magic (60:35:2:3 CHCl$_3$/MeOH/AcOH/H$_2$O)/DCM to give ER811261 (5.5 mg).

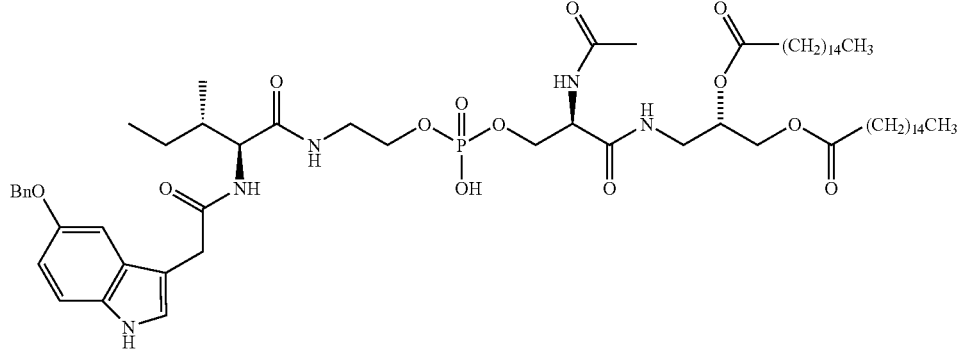

(ER811261)

Example 5

Preparation of ER808977

To a solution of compound 34 (100 mg, 0.11 mmol, prepared as described in U.S. Pat. No. 6,290,973) in DCM (2.0 mL) was added triethylsilane (87 µL, 0.545 mmol) and trifluoroacetic acid (84 µL, 1.1 mmol) at 0° C. The resulting solution was at RT until starting material was consumed (ca. 2 h). The reaction mixture was then concentrated to give the TFA salt. The residue was redissolved in DCM and washed example, $Pd(PPh_3)_4$, $Pd(PtBu_3)_4$, $Pd[P(Me)(tBu_2)]_4$, $PdCl_2(PPh_3)_2$, $PdCl_2(dppf)_2$, $Pd_2(dba)_3BINAP$, or $Pd_2(dba)_3P(o\text{-}tol)_3$) in the presence of a base and an organometallic compound, such as for example, a compound with a $—B(OH)_2$ or $—B(OAlkyl)_2$ group (Suzuki reaction), $—Mg\text{-Hal}$ group (Kumada reaction), $—Zn\text{-Hal}$ group (Negishi reaction), $—Sn(Alkyl)_3$ group (Stille reaction), $—Si(Alkyl)_3$ group (Hiyama reaction), $—Cu\text{-Hal}$ group, $—ZrCp_2Cl$ group, or $—AlMe_2$ group (see Fu and Littke, Angew. Chem. Int. Ed. 41:4176-4211, 2002 for a review of palladium-catalyzed cross-coupling reactions).

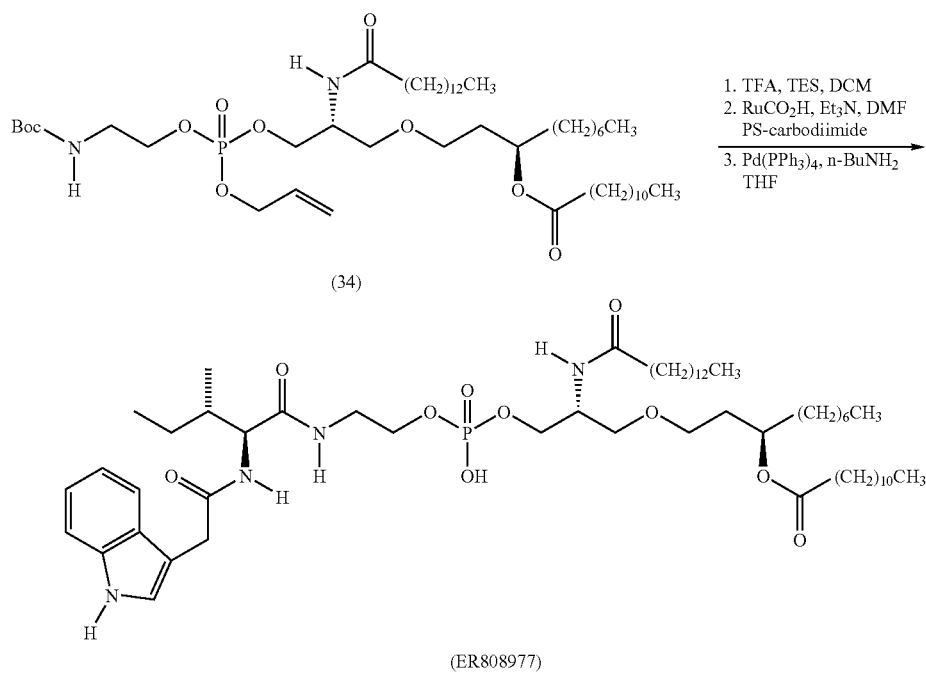

with aqueous saturated sodium bicarbonate solution (×2), and dried over $Na_2SO_4$. Evaporation gave the crude amine free base, which was used immediately without further purification. To a solution of N-(3-indolacetyl)-L-isoleucine ($R^UCO_2H$, 29 mg, 0.1 mmol) in DMF was added triethylamine and polymer supported carbodiimide. The reaction mixture was shaken gently at RT for 2 hours then treated with a solution of the aforementioned crude amine free base in DMF. The reaction mixture was shaken gently at RT overnight. Filtration, followed by concentration in vacuo, gave the crude coupled product. The allyl protecting group(s) was removed by treatment with a catalytic amount of palladium tetrakistriphenylphosphine in THF in the presence of n-butylamine for 2 hours. Purification by flash chromatography gave compound ER808977. Other suitable protected amino acids can be used in place of N-(3-indolacetyl)-L-isoleucine to react with (11) or an analog thereof to produce the compounds shown in Table 5.

Aromatic intermediates that are useful for the preparation of the compounds of the invention, such as, for example, compounds that contain a substituted indole moiety, which are not commericially available can be prepared from aromatic compounds that contain a leaving group such as, for example, a halogen or a triflate. These compounds can be reacted with a palladium catalyst/ligand system (such as, for

Example 6

Preparation of 804469

Step 1. To a solution of mono-tert-butyl malonate (1.6 g, 10 mmol) in DMF (20 mL) was added cesium carbonate (3.42 g, 10.5 mmol) followed by allyl bromide (1.33 g, 11 1 mmol). The reaction was stirred at RT for 16 hours, diluted with EA and worked up with water and brine. The organic solution was dried over $NaSO_4$ and concentrated. The residue was purified by chromatography (silica gel eluted with EA-hexanes) to give compound malonic acid, monoallyl, mono-t-butyl ester (1.873 g, 93%).

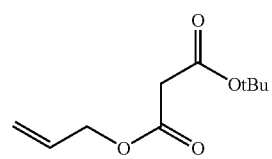

Step 2. To a solution of compound malonic acid, monoallyl, mono-t-butyl ester (1.873 g, 9.27 mmol) in DMF (10 mL) was added sodium hydride (400 mg, 60%, 10 mmol). The reaction was stirred at RT for 20 minutes and followed by addition of 6-tert-butyldiphenylsiloxyl-1-bromohexane (3.69 g, 8.79 mmol). The reaction was stirred at RT for 16 hours, followed by dilution with EA and aqueous workup. The organics were dried over sodium sulfate and concentrated. The residue was purified by chromatography (silica gel eluted with EA-hexanes) to give compound 35 (3.947 g, 83% yield).

phases were separated and the aqueous phase was extracted with dichloromethane. The organic phases were combined, washed with brine, dried over sodium sulfate, and concentrated under vacuum. The residue was purified by chromatography (silica gel eluted with EA-hexanes) to give compound 36 (169 mg, 50% yield).

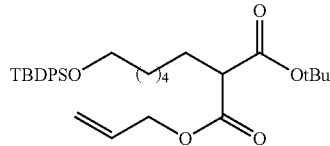

(35)

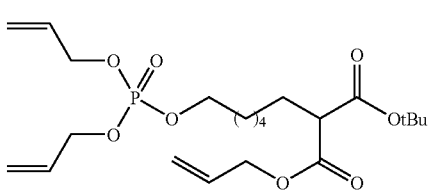

(36)

Step 3. To compound 35 (2.10 g, 3.90 mmol) was added a solution of tetrabutylammonium fluoride in THF (1 M, 5 mL). The reaction was stirred at RT for 2 hours. The solvents were evaporated in vacuo and the residue purified by chromatography (silica gel eluted with EA-hexanes) to give 2-(6-hydroxylhexyl)malonic acid, monoallyl, mono-t-butyl ester (460 mg, 39% yield).

Step 5. To a solution of compound 36 (77 mg, 0.167 mmol) in dichloromethane (0.2 mL) was added triethylsilane (97 mg, 0.836 mmol) followed by trifluoroacetic acid (1 mL). The reaction was stirred at RT for 1 hour and the volatiles were evaporated. The residue was azeotroped with toluene twice and the crude product, compound 37 (77 mg, 0.167 mmol), was used directly in the next step.

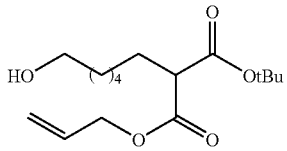

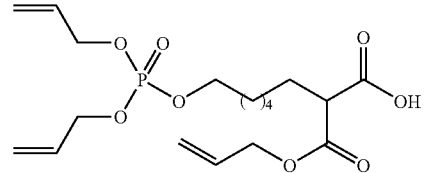

(37)

Step 4. To a solution of 2-(6-hydroxylhexyl)malonic acid, monoallyl, mono-t-butyl ester (220 mg, 0.733 mmol) in dichloromethane (3.5 mL) was added tetrazole (154 mg, 2.20 mmol). The reaction was stirred at RT for 20 minutes followed by addition of diallyl diisopropylphosphoramidite (270 mg, 1.10 mmol). The reaction was stirred at room for 1 hour. The reaction mixture was cooled to 0° C. and 4 mL of THF was added followed by a solution of Oxone (901 mg, 1.466 mmol) in water (4 mL). Stirring was continued for 30 minutes, during which time the reaction was allowed to warm up to RT. The reaction mixture was quenched by adding aqueous sodium thiosulfate and sodium bicarbonate. The two Step 6. To a solution of compound 38 (90 mg, 0.112 mmol, see U.S. Pat. No. 6,290,973) and compound 37 (77 mg crude, 0.167 mmol) in DMF (2.4 mL) was added 1-(3-dimethylaminopropyl)-3-ethylcarbodiimide hydrochloride (38 mg, 0.2 mmol), 1-hydroxybenzotriazole hydrate (23 mg, 0.167 mmol), and triethylamine (20 mg, 0.2 mmol). The reaction was stirred at RT for 16 hours, diluted by EA, washed with water, brine, and dried over sodium sulfate. Purification by chromatography silica gel eluted with MeOH-DCM) gave compound 39 (133 mg, 95%).

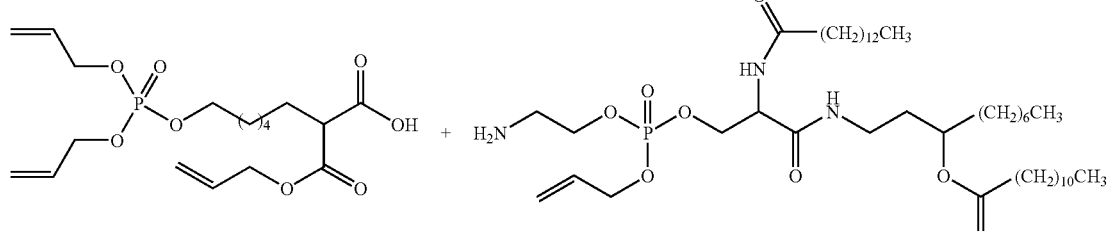

(37)     (38)

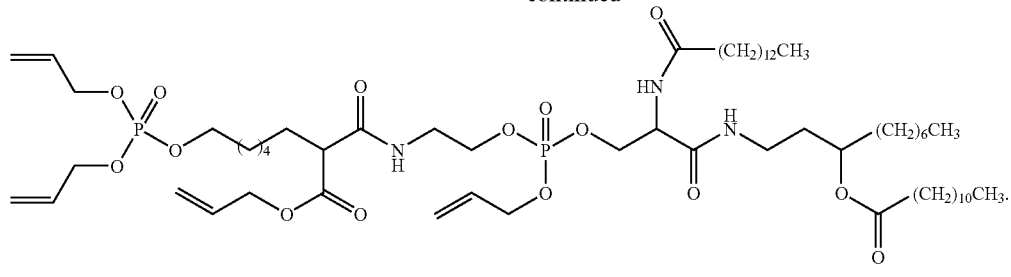

(39)

Step 8. To a solution of compound 39 (133 mg, 0.112 mmol) and phenylsilane (72 mg, 0.666 mmol) in CHCl₃ (11 mL) cooled at 0° C. in an ice-water bath was added tetrakis (triphenylphosphine)-palladium(0) (192 mg, 0.166 mmol). The reaction mixture was stirred at 0° C. for 1.5 hours and quenched by adding CHCl₃:MeOH:H₂O 2:3:1 (1 mL). The reaction mixture was purified by a DEAE column eluted with 0.05-0.1 M NH₄OAc in CHCl₃:MeOH:H₂O 2:3:1. Further purification by HPLC (0/100 to 100/0A/B in 60 minutes. A:Hexane-isopropanol-H₂O 370-540-90, B: H₂O-isopropanol 1-10) gave (ER804469) (35 mg, 30% yield).

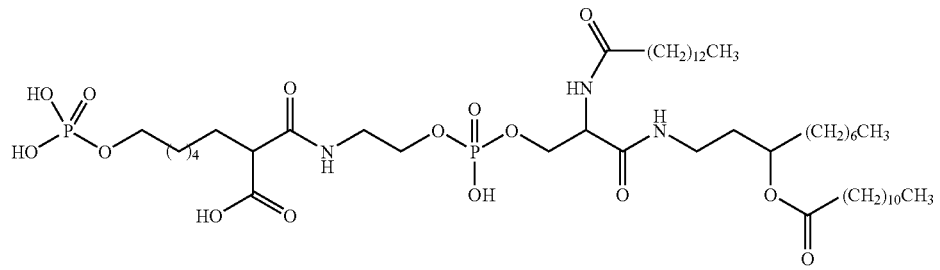

(ER804469)

Example 7

Preparation of 811195

Step 1. To a solution of glycine t-butyl ester (511 mg, 3.05 mmol) and N-(3-indolylacetyl)-L-isoleucine (878 mg, 3.05 mmol) in DMF/DCM (5 mL/5 mL) at RT was added DIPEA (2.1 mL, 12.2 mmol) and HBTU (2.31 g, 6.10 mmol). After stirring for 1 hour, the reaction mixture was diluted with EA and washed with water (2×) and brine (1×). Purification by silica gel chromatography gave compound 40 (830 mg, 68% yield).

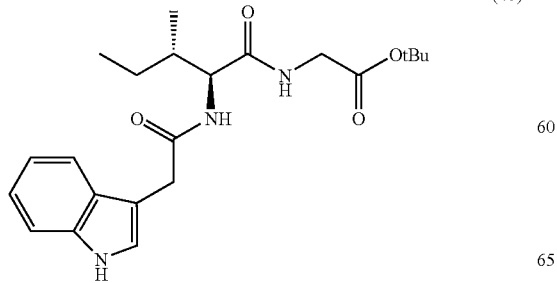

(40)

Step 2. To compound 40 (83.0 mg, 0.207 mmol) was added 4 M HCl solution in dioxane (2 mL, 8 mmol). After stirring at RT for 18 hours, the reaction mixture was concentrated and azeotroped with THF/Toluene to give compound 41 (93.3 mg, overweight).

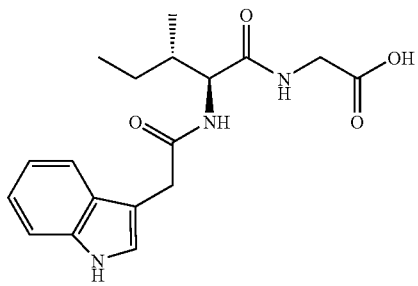

(41)

Step 3. To a solution of compound 42 (2.05 g, 3.20 mmol, prepared as described in U.S. Pat. No. 6,290,973) in DCM (20 mL) at 0° C. was added DMAP (78.0 mg, 0.64 mmol) and Et$_3$N (892 μL, 6.40 mmol), followed by MsCl (496 μL, 6.40 mmol). The ice bath was removed and the reaction mixture stirred at RT for 30 minutes. The reaction mixture was cooled to 0° C. and quenched with 0.5 N HCl. The aqueous layer was extracted with DCM (2×). Purification by silica gel chromatography gave compound 43 (2.30 g, 100% yield).

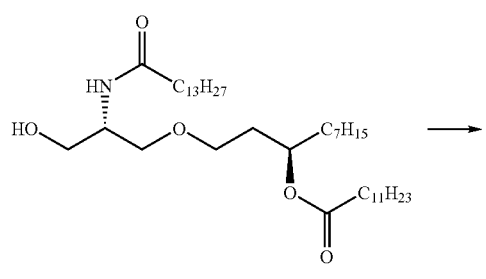

(42)

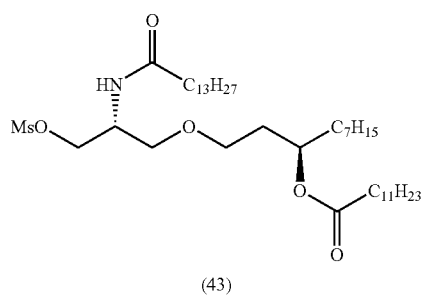

(43)

Step 4. To a solution of compound 43 (2.30 g, 3.20 mmol) in DMF (10 mL) at RT was added NaN$_3$ (624 mg, 9.6 mmol). The reaction mixture was heated at 1 00° C. for a total of 20 hours. After cooling to RT, the reaction mixture was diluted with EA and washed with water and brine. Purification by silica gel chromatography gave compound 44 (1.24 g, 58% yield).

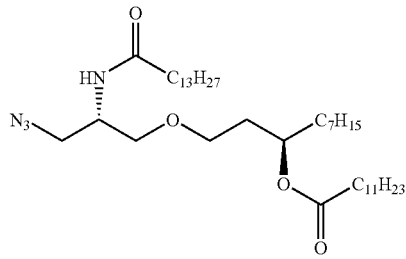

(44)

Step 5. To a solution of compound 44 (1.24 g, 1.86 mmol) in MeOH (20 mL) at RT was added Pd/C (200 mg). The reaction mixture was stirred under an atmosphere of hydrogen for 4 hours. After filtration through Celite, the crude product was purified by silica gel chromatography to give compound 45 (793 mg, 64% yield).

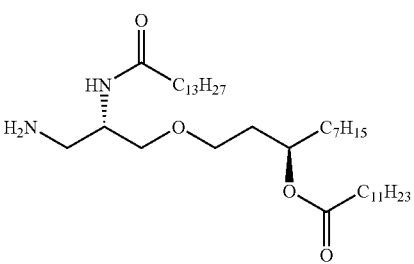

(45)

Step 6. To a solution of compound 45 (102 mg, 0.16 mmol) and Boc-L-serine (39 mg, 0.19 mmol) in DCM (1 mL) was added EDC (46 mg, 0.24 mmol). After stirring for 20 hours at RT, the reaction mixture was concentrated and purified on prep TLC to give compound 46 (113 mg, 86% yield).

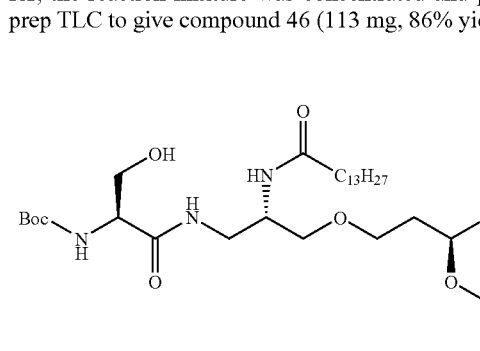

(46)

Step 7. To compound 46 (113 mg, 0.137 mmol) was added 4.0 N HCl (1.5 mL, 6.0 mmol). After stirring at RT for 2.5 h, the reaction mixture was concentrated and azeotroped with toluene (2×) to give compound 47 (108 mg, 100% yield).

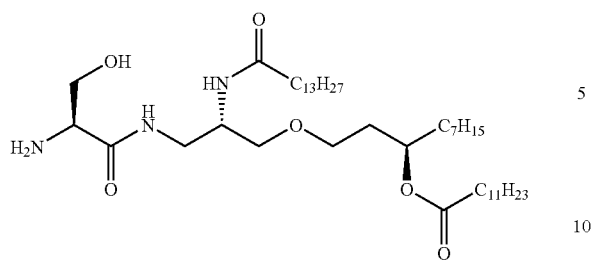

(47)

Step 8. To a solution of compound 47 (108 mg, 0.137 mmol) and compound 41 (79.0 mg, 0.207 mmol) in DMF (1.0 mL) was added EDC (28 mg, 0.411 mmol), HOBT (48 µL, 0.207 mmol), and DIPEA (48 mL, 0.274 mmol). After stirring at RT for 17 hours, the reaction mixture was diluted with EA and washed with water and brine. Purification by silica gel chromatography gave compound 48 (13.7 mg, 9.5% yield).

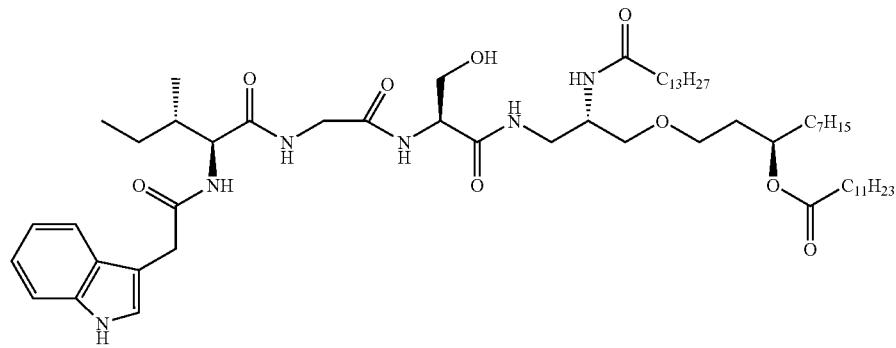

(48)

Step 9. To the solution of compound 48 (13.7 mg, 0.013 mmol) in pyridine (1.0 mL) was added Py-SO$_3$ (excess). After stirring at RT for 24 hours, the reaction mixture was filtered through cotton, concentrated and azeotroped with toluene. Purification by silica gel chromatography gave ER811195 (8.6 mg, 58% yield).

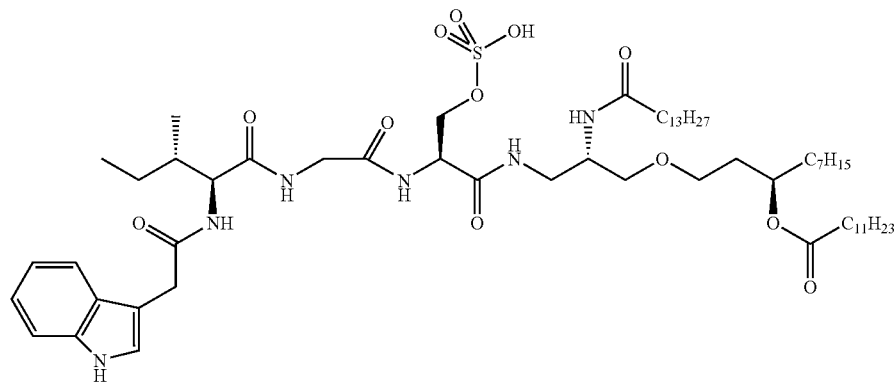

(ER811195)

Example 7

Preparation of 809266

Step 1. To a solution of 3(R)-1,3-dihydroxydecane (6.39 g, 36.6 mmol) in DCM (40 mL) at 0° C. was added DMAP (0.447 g, 3.66 mmol), triethylamine (10.2 mL, 73.2 mmol) and TBDPSCI (10.7 mL, 40.4 mmol). After stirring at RT for 20 hours, the reaction mixture was diluted with DCM, washed with 0.5 N HCl and saturated bicarbonate. The combined organic solution was dried with sodium sulfate and concentrated to give crude compound 49 (about 16.5 g), which was used as is.

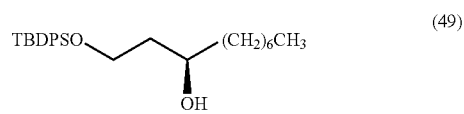
(49)

Step 2. To a solution of crude compound 49 (5.35 g, about 13.0 mmol) in anhydrous THF (45 mL) at 0° C. was added triphenylphosphine (10.3 g, 38.9 mmol), 4-nitrobenzonic acid (6.5 g, 38.9 mmol) and DEAD (6.1 mL, 38.9 mmol). After stirring at 0° C. for 60 minutes, the reaction mixture was kept at −20° C. in a freezer overnight. Purification on a Biotage column using EA/Hexane gave compound 50 (5.77 g, 79% yield).

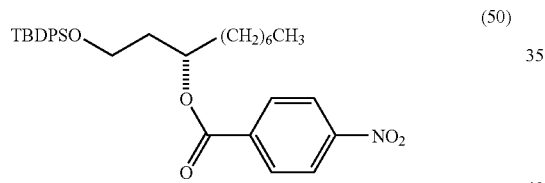
(50)

Step 3. To a solution of compound 50 (5.77 g, 10.3 mmol) in 1:1 THF:MeOH (120 mL) at RT was added potassium carbonate (1.72 g, 12.33 mmol) in one portion. Stirring was continued at RT for 4 hours. Purification on a Biotage column using EA/Hexane gave compound 51 (3.26 g, 77% yield).

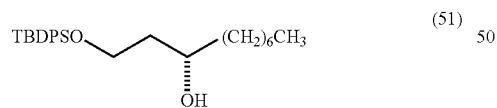
(51)

Step 4. To a solution of compound 51 (3.26 g, 7.9 mmol) in anhydrous DCM (20 mL) at 0° C. was added DMAP (0.193 g, 1.5 mmol), and triethylamine (2.2 mL, 15.2 mmol), followed by the slow addition of methanesulfonyl chloride (1.22 mL, 15.2 mmol). After stirring at 0° C. for 30 minutes, the reaction mixture was allowed to warm up to RT and stirred for an additional 30 minutes. The reaction mixture was diluted with 0.5 M HCl (50 mL) and extracted with DCM (3×40 mL). The organic layer was washed with saturated sodium bicarbonate solution, dried with MgSO4, filtered, and concentrated to give compound 52 (4.0 g), which was used directly as is in the next reaction.

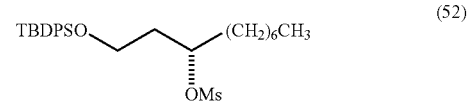
(52)

Step 5. To a solution of compound 52 (3.6 g, 7.34 mmol) in DMF (30 mL) was added sodium azide (1.45 g, 22.3 mmol) at RT. The reaction mixture was heated in an oil bath at 140° C. overnight. After dilution with water and extraction with EA, the combined organic layers were dried with $MgSO_4$ and concentrated. Purification on a Biotage column using 10% EA/Hexane gave compound 53 (2.27 g, 70% yield).

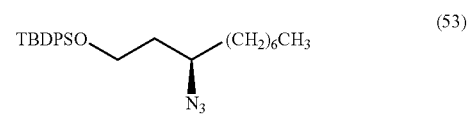
(53)

Step 6. To a solution of compound 53 (2.25 g, 5.15 mol) in anhydrous THF (20 mL) at RT was added tetrabutylammonium fluoride (4.04 g, 15.44 mmol) in one portion. The mixture was stirred at RT for 90 minutes and diluted with water/EA. The aqueous layer was extracted with EA (3×20 mL), washed with 0.1 N HCl (20 mL) and saturated sodium bicarbonate (20 mL). Flash chromatography with Biotage 40 mm column (30% EA/Hexane) gave compound 54 (1.02 g, 99% yield).

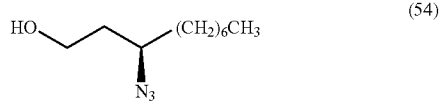
(54)

Step 7. To a solution of compound 54 (1.01 g, 5.1 mmol) in DCM (20.0 mL) at 0° C. was added DMAP (45.0 mg, 0.37 mmol), triethylamine (1.4 mL, 10.1 mmol), and methanesulfonyl chloride (0.78 mL, 10.1 mmol). The resulting mixture was stirred for 2 hours at 0° C. and overnight at RT. The reaction mixture was diluted with water, extracted with EA (3×20 mL), dried with $MgSO_4$, filtered, and concentrated. Flash chromatography using Biotage 25 mm column (20% EA/Hexane) gave compound 55 (1.27 g, 90% yield).

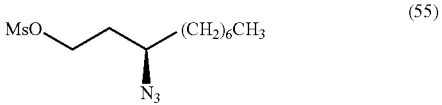
(55)

Step 8. To a suspension of potassium tert-butoxide (0.98 g, 8.73 mmol) in THF (5.0 mL) at 0° C. was added a solution of benzimidate compound 56 (from L-serine methyl ester) (1.5466 g, 8.73 mmol) in THF (10.0 mL) using a syringe pump at a rate of 0.24 mL/minute. The resulting reaction mixture was stirred for 1 hour at 0° C. To the mixture was added a solution of compound 55 (1.21 g, 4.36 mmol) in THF (10.0 mL) via syringe pump at a rate of 0.24 mL/minute. The reaction mixture was stirred for 48 hours. Flash chromatography (30% EA/Hexane) gave compound 57 (0.73 g, 46% yield).

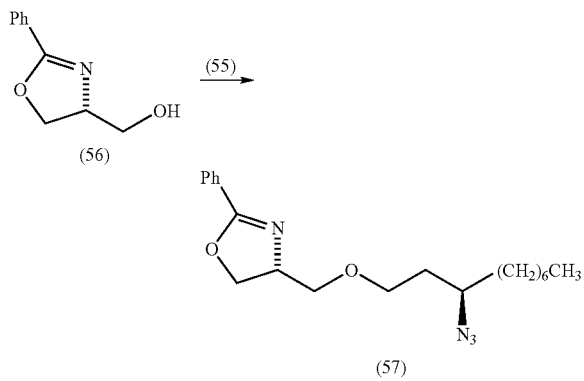

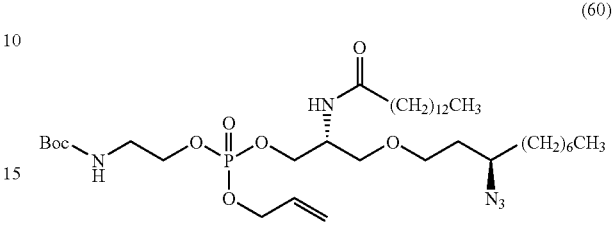

Step 9. To a solution of compound 57 (0.93 g, 2.6 mmol) in MeOH (10 mL) at RT was added 2 N HCl (7.8 mL, 15.6 mmol). The reaction mixture was heated for 2 hours at 90° C. After the reaction mixture was cooled down to RT, a solution of 7.4 N NaOH (4.2 mL, 31.2 mmol) was added to the reaction mixture at RT. The reaction mixture was heated for 4 hours at 90° C., cooled to RT, left standing overnight. The reaction mixture was extracted with DCM (3×50 mL) and the combined organics concentrated to give crude compound 58 (0.81 g), which was use for next step without further purification.

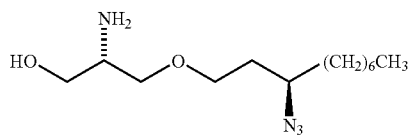

Step 10. To a solution of compound 58 (0.72 g) in THF (10 mL) at RT was added saturated sodium bicarbonate (10 mL). To the resulting mixture was added myristoyl chloride (0.63 mL, 2.24 mmol) at 0° C. Stirring was continued for 20 minutes at 0° C. The reaction mixture was diluted with water, extracted with DCM (3×10 mL), dried and concentrated. Purification by flash chromatography (30% EA/Hexane) gave compound 59 (0.92 g, 76% yield for 2 steps).

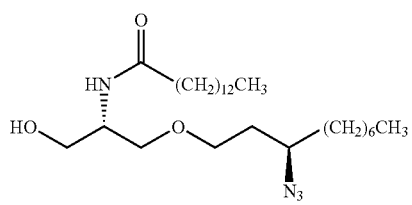

Step 11. To a solution of compound 59 (0.92 g) in dichloromethane (25 mL) at RT was added pyridinium trifluoroacetate (803 mg). The reaction mixture was cooled to −20° C.

and Boc-phosphorylating reagent compound 6 (1.10 g) was added. After 2 hours, 30% hydrogen peroxide (0.88 mL) was added and the reaction was allowed to warm to RT. To the reaction mixture was added a solution of sodium thiosulfate (1.24 g in 20 mL water). Aqueous work-up and column chromatography gave compound 60 (0.619 g, 47% yield).

Step 12. To a solution of compound 60 (0.29 g, 0.38 mmol) in 20/1 THF:H$_2$O (5.5 mL) at RT was added triphenylphosphine (0.18 g, 0.69 mmol). The resulting mixture was stirred at RT overnight, concentrated, and dried azeotropically with toluene to give compound 61, which was used for next step without purification.

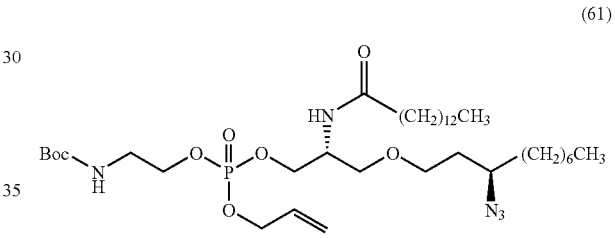

Step 13. To a solution of crude compound 61 (0.50 g) in anhydrous DCM (5.0 mL) at 0° C. was added lauric acid (0.14 g, 0.70 mmol), EDC (0.13 g, 0.70 mmol), and HOBt (0.094 g, 0.70 mmol). The resulting mixture was stirred at RT until compound 61 was consumed. Flash chromatography gave compound 62 (0.122 g, 39% yield for 2 steps).

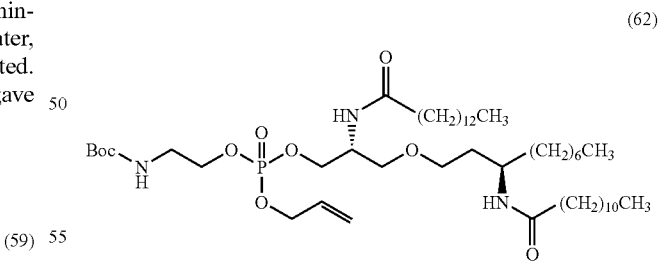

Step 14. To a solution of compound 62 (0.122 g, 0.135 mmol) in DCM was added triethylsilane (108 μL, 0.67 mmol) and TFA (104 μL, 1.35 mmol) at 0° C. The resulting mixture was stirred at RT and monitored by TLC (10% MeOH/DCM) until compound 62 was consumed. The reaction mixture was diluted with water and saturated sodium bicarbonate, extracted with DCM (3×20 mL), dried with sodium sulfate, and concentrated to give the crude amine compound 63, which was used directly in the next reaction without further purification.

(63)

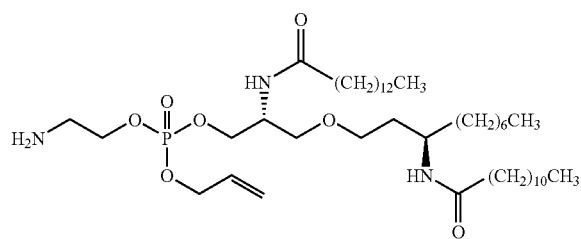

Step 15. To a solution of compound 63 (55.4 mg, 0.069 mmol) and 2-(4-allyloxybenzyl)malonic acid, mono allyl ester (60.1 mg, 0.207 mmol) in DCM (3.0 mL) was added EDC (26.3 mg, 0.138 mmol), HOBt (18.6 g, 0.138 mmol), and triethylamine (72.2 μL, 0.41 mmol) at −5° C. The mixture was stirred at RT overnight, diluted with saturated bicarbonate, extracted with DCM (3×20 mL), dried with sodium sulfate, and concentrated. Flash chromatography on a 25 mm Biotage column (40% Acetone/Hexane) gave compound 64 (52 mg, 69% yield).

(64)

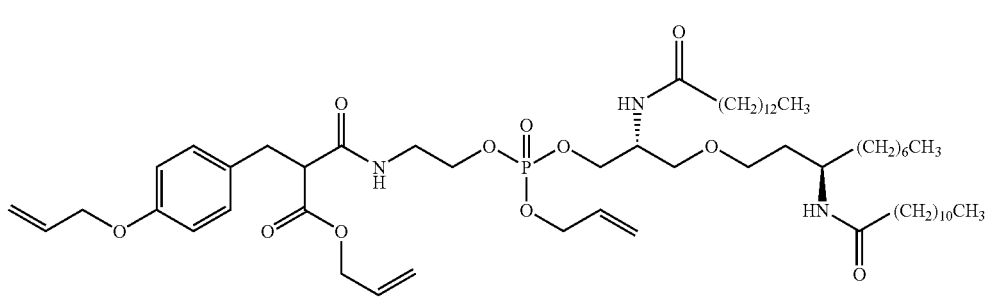

Step 16. To a solution of compound 64 (51.7 mg, 0.048 mmol) in THF was added phenylsilane (53.4 μL, 0.433 mmol), triphenylphosphine (22.7 mg, 0.086 mmol), and tetrakis(triphenylphosphine)palladium(0) (16.7 mg, 0.014 mmol) at RT. The reaction mixture was stirred at RT for 60 minutes and loaded onto DEAE, eluted with 2:3:1/CHCl$_3$:MeOH:H$_2$O to remove the palladium catalyst, followed by column elution with 0.01 M, 0.02 M NH$_4$OAC in 2:3:1. Product fractions were collected and diluted with an equal volume of DCM. The organic solution was concentrated to give ER809266 (32.8 mg, 71% yield).

(ER809266)

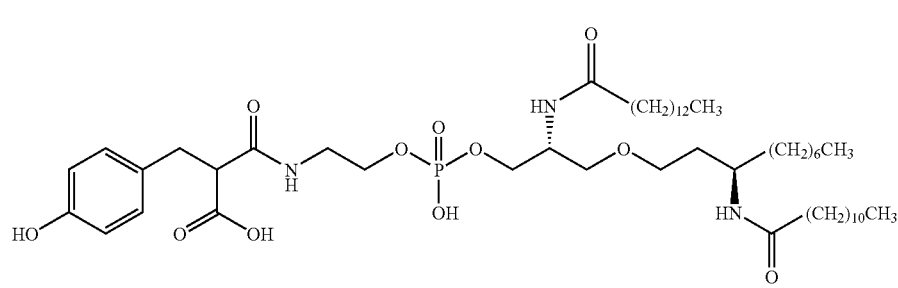

ER809265 and ER809267 can be prepared by a similar sequence of reactions, with the exception that the configuration of the chiral center of compound 49 is not inverted before mesylation and azide displacement.

are incubated at 37° C., 5% $CO_2$, for 24 hours. The growth medium used is D-MEM, 10% fetal bovine serum, 2 mM L-glutamine, 10 μg/mL Ciprofloxacin, 300 μg/mL Geneticin (G418), and 150 μg/mL Zeocin.

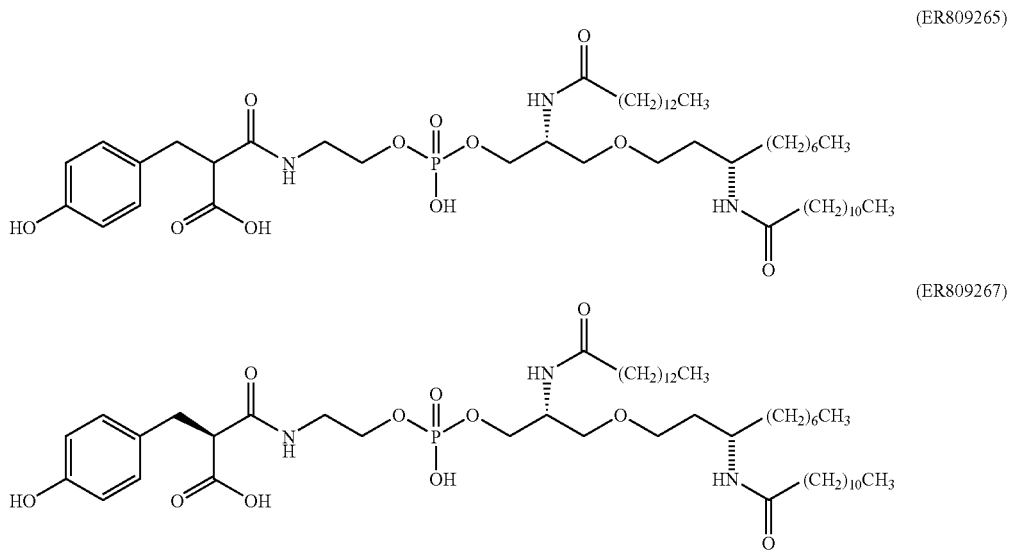

Example 8

Identification of TLR2 and TLR4 Antagonists

Materials

Either Pam3CSK4 and R-MALP-2 lipopeptides (EMC-Microcollections), or lipopolysaccharide (LPS, List Biologicals) are dissolved in water to a concentration of 1 mg/mL, sonicated 5 times for 30 seconds, and stored in aliquots at −20° C. Prior to addition to cells, an aliquot of the dissolved ligand is sonicated for 1 minute and then is diluted in medium to 2 ng/mL Pam3CSK4, 16 ng/mL R-MALP-2, or 100 ng/mL LPS. The final concentration in the assay is 0.2 ng/mL Pam3CSK4, 1.6 ng/mL R-MALP-2, or 10 ng/mL LPS.

The test compounds are stored as 30 mM stocks in 4% DMSO. The final concentrations of the test compounds in the assay are 0.1, 0.3, 1, 3, 10, and 30 μM in 0.2% DMSO. 0.2% DMSO is used in the assay as a control.

HEK293 cells stably carrying plasmids for TLR4, MD2, and the NF-κB reporter gene ELAM-1-luciferase (HEK-TLR4-MD2-ELAM) were generated as described by Yang et al., *J. Biol. Chem.* 275:20861-20866, 2000.

HEK-TLR2-ELAM cells were generated by a two-step method. In step 1, Hek293 cells were transfected with pcDNA3.0 encoding human TLR2 followed by antibiotic selection with G418 in D-MEM supplemented with 10% fetal bovine serum (Gibco BRL) to generate Hek-TLR2 cells. In step 2, Hek-TLR2 cells were transfected with pELAM-luc/Zeo followed by antibiotic selection with Zeocin in D-MEM supplemented with 10% fetal bovine serum. Transfectants were screened for TLR2 responsiveness by measuring ligand-induced pELAM-luciferase reporter activity, and analyzed for TLR2 mRNA expression by RT-PCR.

TLR2 Antagonism Assay

Step 1. On day 1, HEK-TLR2-ELAM cells are plated at $2\times10^5$ cells/mL, 80 μL/well, in 96-well black plates. The cells Step 2. On day 2, 10 μL of each test compound is added to the wells, and 10 μL lipopeptide is added to all of the wells. The plates are then incubated at 37° C., 5% $CO_2$, for 18 hours.

Step 3. On day 3, 25 μL of Steady-Glo reagent (Promega, Inc.) is added to each well. The plates are then shaken for 5 minutes, and the chemiluminescence of each well is read in a Wallac1450 MicroBetaTriLux counter. Dose-response curves were plotted in KaleidaGraph, version 3.5 Synergy Software, and $IC_{50}$ values were calculated.

TLR4 Antagonism Assay

Step 1. On day 1, HEK-TLR4MD2-ELAM cells were plated at $4\times10^5$ cells/mL, 80 μL/well, in 96-well black plates. The growth medium used is D-MEM, 10% fetal bovine serum, 2 mM L-glutamine, 10 μg/mL Ciprofloxacin, 300 μg/mL Geneticin (G418), 150 μg/mL Zeocin, and 50 μg/mL Hygromycin.

Step 2. On day 2, 10 μL of each test compound is added to the wells, and 10 μL of LPS plus 10 nM soluble CD 14 (Biometec) is added to all of the wells. The plates are then incubated at 37° C., 5% $CO_2$, for 18 hours.

Step 3. On day 3, 25 μL of Steady-Glo reagent (Promega, Inc.) is added to each well. The plates are then shaken for 5 minutes, and the chemiluminescence of each well is read in a Wallac1450 MicroBetaTriLux counter. Dose-response curves were plotted in KaleidaGraph, version 3.5 Synergy Software, and $IC_{50}$ values were calculated.

Antagonistic activities of selected compounds of the invention in the TLR2 and TLR4 assays are presented in Table 6.

TABLE 6

| Compound | TLR2 activity by Pam3CSK4 ($IC_{50}$, μM) | TLR4 ($IC_{50}$, μM) |
|---|---|---|
| ER811243 | 0.23 | 0.2 |
| ER812011 | 0.24 | 6.6 |

TABLE 6-continued

| Compound | TLR2 activity by Pam3CSK4 (IC$_{50}$, µM) | TLR4 (IC$_{50}$, µM) |
|---|---|---|
| ER811212 | 0.39 | 1.0 |
| ER811245 | 0.43 | 3.4 |
| ER811211 | 0.44 | 0.7 |
| ER811393 | 0.46 | 12.3 |
| ER811261 | 0.50 | 1.8 |
| ER811395 | 0.65 | 1.8 |
| ER811232 | 0.75 | 0.4 |
| ER811254 | 0.77 | 3.6 |

TLR$^2$ can cooperate with TLR$^6$ and TLR$^1$ to form heterodimers and recognize different microbial ligands. For example, TLR$^2$ associates with TLR$^1$ to recognize triacylated lipopeptide (Pam3CSK4), but interacts with TLR$^6$ to recognize diacylated lipopeptide (R-MALP-2). Such heterodimer selectivity for compounds of the invention is shown in Table 7 for ER811245 and ER808977.

TABLE 7

| Compound | TLR2 activity by Pam3CSK4 (IC$_{50}$, µM) | TLR2 activity by R-MALP-2 (IC$_{50}$, µM) |
|---|---|---|
| ER-811245 | 0.44 | 30 |
| ER-808977 | 0.24 | 20 |

From the foregoing description, it will be apparent that variations and modifications may be made to the invention described herein to adapt it to various usages and conditions. Such embodiments are also within the scope of the following claims.

All publications mentioned in this specification are herein incorporated by reference to the same extent as if each independent publication or patent application was specifically and individually indicated to be incorporated by reference.

Other embodiments are within the following claims.

What is claimed is:

1. A method of treating a disease or condition characterized by Toll-like receptor 2 activation in a patient, wherein said disease or condition is selected from the group consisting of inflammatory bowel disease, sepsis, periodontal disease, acne, chronic obstructive pulmonary disease, arthritis, cystic fibrosis, ischemia/reperfusion injury, asthma, necrotizing enterocolitis, leprosy, atopic dermatitis, psoriasis, allergies, coronary artery bypass grafting, and atherosclerosis said method comprising administering to the patient a Toll-like receptor 2 antagonist of formula I

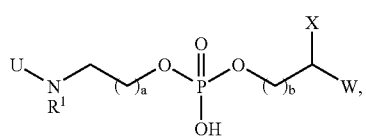

(I)

or a pharmaceutically acceptable salt thereof, wherein
a is an integer of 1 to 3;
b is an integer of 0 to 4, wherein when b is 0, the carbon bonded to X and W is not bonded to 2 or more heteroatoms;
$R^1$ is H or $C_{1-6}$ alkyl;
X is selected from the group consisting of —NR$^{X1}$V, —N(R$^{X1}$)C(O)V, —N(R$^{X1}$)C(S)V, —N(R$^{X1}$)C(O)N(R$^{X2}$)V, —N(R$^{X1}$)C(S)N(R$^{X2}$)V, —N(R$^{X1}$)C(O)OV, —N(R$^{X1}$)S(O)$_2$V, —C(O)N(R$^{X1}$)V, —C(O)OV, —OC(O)V, —OC(O)OV, and —OC(O)N(R$^{X1}$)V, where each of R$^{X1}$ and R$^{X2}$ is, independently, H or $C_{1-6}$ alkyl, and V is a $C_{1-20}$ alkyl, $C_{1-20}$ alkenyl, or $C_{1-20}$ alkynyl group, optionally substituted with halo, hydroxyl, $C_{1-21}$ acyloxy, oxo, $C_{1-20}$ alkoxyl, or $C_{1-20}$ thioalkoxyl and optionally containing 1 or 2 phenyl or biphenyl moieties in and/or at the end of the carbon chain;
W is selected from the group consisting of H, —C(O)N(R$^{W1}$)R$^{W2}$, —C(O)OR$^{W2}$, —(CH$_2$)$_c$OR$^{W3}$, —(CH$_2$)$_c$SR$^{W3}$, —(CH$_2$)$_c$O(CH$_2$)$_d$CH(OR$^{W3}$)R$^{W4}$, —(CH$_2$)$_c$S(CH$_2$)$_d$CH(OR$^{W3}$)R$^{W4}$, —C(O)N(R$^{W1}$)(CH$_2$)$_c$CH(OR$^{W3}$)R$^{W4}$, and —C(O)N(R$^{W1}$)(CH$_2$)$_c$CH(OR$^{W3}$)(CH$_2$)$_e$OR$^{W5}$, wherein each of c and d is, independently, an integer of 1 to 4, e is an integer of 2 to 4, R$^{W1}$ is H or $C_{1-6}$ alkyl, R$^{W2}$ is $C_{1-20}$ alkyl, $C_{1-20}$ alkenyl, or $C_{1-20}$ alkynyl, each of R$^{W3}$ and R$^{W5}$ is, independently, H, $C_{1-20}$ alkyl, $C_{1-21}$ acyl, $C_{1-20}$ alkenyl, or $C_{1-20}$ alkynyl, and R$^{W4}$ is H, $C_{1-20}$ alkyl, $C_{1-20}$ alkenyl, or $C_{1-20}$ alkynyl, wherein each of R$^{W2}$, R$^{W3}$, R$^{W4}$, and R$^{W5}$ is optionally substituted with halo, hydroxyl, $C_{1-21}$ acyloxy, oxo, $C_{1-20}$ alkoxyl, or $C_{1-20}$ thioalkoxyl, optionally contains 1 to 2 phenyl or biphenyl moieties in and/or at the end of the carbon chain, and optionally contains 1 to 4 non-vicinal oxygen atoms in the carbon chain; and
U is selected from the group consisting of

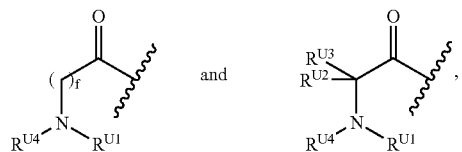

wherein
f is an integer of 1 to 4, g is 0 or 1,
each of R$^{U1}$, R$^{U2}$, and R$^{U3}$ is, independently, H, optionally substituted $C_{1-6}$ alkyl, optionally substituted $C_{7-16}$ aralkyl, or optionally substituted $C_{2-15}$ heterocyclylalkyl, or R$^{U1}$ is H or optionally substituted $C_{1-6}$ alkyl and R$^{U2}$ and R$^{U3}$ together with the carbon atom they are bonded to form an optionally substituted $C_{3-6}$ aliphatic ring, or R$^{U2}$ is H and R$^{U3}$ and R$^{U1}$ together with the carbon atom bonded to R$^{U3}$ and the nitrogen atom bonded to R$^{U1}$ form an optionally substituted 4-6- membered heterocyclic ring, and R$^{U4}$ is selected from the group consisting of —C(O)R$^{U5}$ and —C(O)OR$^{U6}$ wherein R$^{U5}$ is an optionally substituted $C_{1-9}$ indole, and R$^{U6}$ is an optionally substituted $C_{1-6}$ alkyl.

2. The method of claim 1, wherein X or W contains at least one linear alkyl moiety of 7 or more carbons.

3. The method of claim 1, wherein each of X and W contains at least one linear alkyl moiety of 7 or more carbons.

4. The method of claim 1, wherein W is —C(O)NH(CH$_2$)$_2$CH(OH)R$^{W4}$, wherein R$^{W4}$ is $C_{7-19}$ alkyl.

5. The method of claim 1, wherein W is —C(O)NH(CH$_2$)$_2$CH$_2$OR$^{W3}$, wherein R$^{W3}$ is —C(O)(CH$_2$)$_{aa}$CH$_3$, wherein aa is an integer of 6 to 18.

6. The method of claim 1, wherein W is —C(O)NH(CH$_2$)$_2$CH(OR$^{W3}$)R$^{W4}$, wherein R$^{W3}$ is —C(O)(CH$_2$)$_{aa}$CH$_3$ and R$^{W4}$ is CH$_2$OC(O)(CH$_2$)$_{bb}$CH$_3$, wherein each of aa and bb is, independently, an integer of 6 to 18.

7. The method of claim 1, wherein U is —C(O)C(R$^{U2}$)(R$^{U3}$)NHR$^{U4}$ or —C(O)(CH$_2$)$_f$NHR$^{U4}$ or wherein R$^{U2}$ is an optionally substituted C$_{1-6}$ alkyl, R$^{13}$ is H, and R$^{U4}$ —C(O)R$^{U5}$, wherein R$^{U5}$ is an optionally substituted C$_{2-9}$ indole, or an optionally substituted C$_{2-9}$ heteroaryl.

8. The method of claim 1, wherein U is

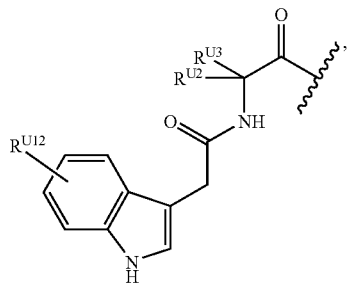

wherein

R$^{U2}$ is C$_{1-6}$ alkyl, R$^{U3}$ is H, and R$^{U12}$ is optionally substituted C$_{6-10}$ aryl, optionally substituted C$_{6-10}$ aryloxy, optionally substituted C$_{7-16}$ aralkyl, optionally substituted C$_{7-16}$ aralkoxy, optionally substituted C$_{2-9}$ heterocyclyl, optionally substituted C$_{2-9}$ heterocyclyloxy, optionally substituted C$_{3-15}$ heterocyclylalkyl, or optionally substituted C$_{3-15}$ heterocyclylalkyloxy.

9. The method of claim 1, wherein U is selected from the group consisting of

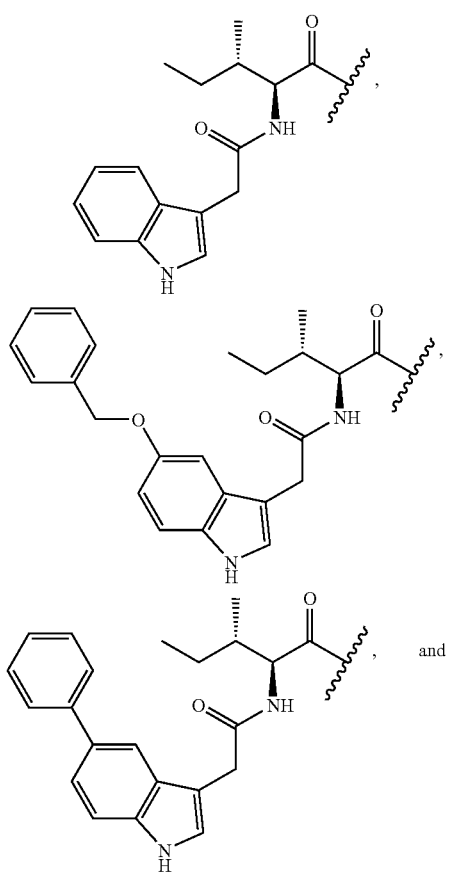

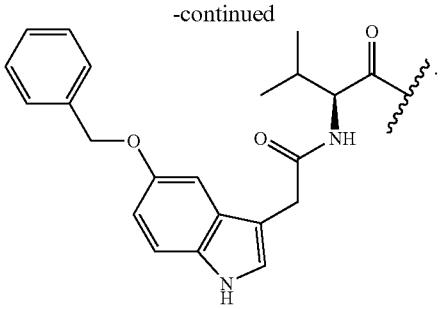

10. The method of claim 1, wherein:

X is selected from the group consisting of —NR$^{X1}$V, —N(R$^{X1}$)C(O)V, —N(R$^{X1}$)C(S)V, —N(R$^{X1}$)C(O)N(R$^{X2}$)V, —N(R$^{X1}$)C(S)N(R$^{X2}$)V, —N(R$^{X1}$)C(O)OV, —N(R$^{X1}$)S(O)$_2$V, —C(O)N(R$^{X1}$)V, —C(O)OV, —OC(O)OV, and —OC(O)N(R$^{X1}$)V, where each of R$^{X1}$ and R$^{X2}$ is, independently, H or C$_{1-6}$ alkyl, and V is a C$_{1-20}$ alkyl, C$_{1-20}$ alkenyl, or C$_{1-20}$ alkynyl group, optionally substituted with halo, hydroxyl, C$_{1-21}$ acyloxy, oxo, C$_{1-20}$ alkoxyl, or C$_{1-20}$ thioalkoxyl and optionally containing 1 or 2 phenyl or biphenyl moieties in and/or at the end of the carbon chain.

11. The method of claim 1, wherein:

W is selected from the group consisting of H, —C(O)N(R$^{W1}$)R$^{W2}$, —C(O)OR$^{W2}$, —(CH$_2$)$_c$SR$^{W3}$, —(CH$_2$)$_c$O(CH$_2$)$_d$CH(OR$^{W3}$)R$^{W4}$, —(CH$_2$)$_c$S(CH$_2$)$_d$CH(OR$^{W3}$)R$^{W4}$, —C(O)N(R$^{W1}$)(CH$_2$)$_c$CH(OR$^{W3}$)R$^{W4}$, and —C(O)N(R$^{W1}$)(CH$_2$)$_c$CH(OR$^{W3}$)(CH$_2$)$_e$OR$^{W5}$, wherein each of c and d is, independently, an integer of 1 to 4, e is an integer of 2 to 4, R$^{W1}$ is H or C$_{1-6}$alkyl, R$^{W2}$ is C$_{1-20}$ alkyl, C$_{1-20}$ alkenyl, or C$_{1-20}$ alkynyl, each of R$^{W3}$ and R$^{W5}$ is, independently, H, C$_{1-20}$alkyl, C$_{1-21}$acyl, C$_{1-20}$alkenyl, or C$_{1-20}$alkynyl, and R$^{W4}$ is H, C$_{1-20}$ alkyl, C$_{1-20}$ alkenyl, or C$_{1-20}$ alkynyl, wherein each of R$^{W2}$, R$^{W3}$, R$^{W4}$, and R$^{W5}$ is optionally substituted with halo, hydroxyl, C$_{1-21}$ acyloxy, oxo, C$_{1-20}$ alkoxyl, or C$_{1-20}$ thioalkoxyl, optionally contains 1 to 2 phenyl or biphenyl moieties in and/or at the end of the carbon chain, and optionally contains 1 to 4 non-vicinal oxygen atoms in the carbon chain.

12. The method of claim 1, wherein:

X is selected from the group consisting of —NR$^{X1}$V, —N(R$^{X1}$)C(O)V, —N(R$^{X1}$)C(S)V, —N(R$^{X1}$)C(O)N(R$^{X2}$)V, —N(R$^{X1}$)C(S)N(R$^{X2}$)V, —N(R$^{X1}$)C(O)OV, —N(R$^{X1}$)S(O)$_2$V, —C(O)N(R$^{X1}$)V, —C(O)OV, —OC(O)OV, and —OC(O)N(R$^{X1}$)V, where each of R$^{X1}$ and R$^{X2}$ is, independently, H or C$_{1-6}$ alkyl, and V is a C$_{1-20}$ alkyl, C$_{1-20}$ alkenyl, or C$_{1-20}$alkynyl group, optionally substituted with halo, hydroxyl, C$_{1-21}$ acyloxy, oxo, C$_{1-20}$ alkoxyl, or C$_{1-20}$ thioalkoxyl and optionally containing 1 or 2 phenyl or biphenyl moieties in and/or at the end of the carbon chain; and W is selected from the group consisting of H, —C(O)N(R$^{W1}$)R$^{W2}$, —C(O)OR$^{W2}$, —(CH$_2$)$_c$SR$^{W3}$, —(CH$_2$)$_c$O(CH$_2$)$_d$CH(OR$^{W3}$)R$^{W4}$, —(CH$_2$)$_c$S(CH$_2$)$_d$CH(OR$^{W3}$)R$^{W4}$, —C(O)N(R$^{W1}$)(CH$_2$)$_c$CH(OR$^{W3}$)R$^{W4}$, and —C(O)N(R$^{W1}$)(CH$_2$)$_c$CH(OR$^{W3}$)(CH$_2$)$_e$OR$^{W5}$, wherein each of c and d is, independently, an integer of 1 to 4, e is an integer of 2 to 4, R$^{W1}$ is H or C$_{1-6}$alkyl, R$^{W2}$ is C$_{1-20}$ alkyl, C$_{1-20}$ alkenyl, or C$_{1-20}$ alkynyl, each of R$^{W3}$ and R$^{W5}$ is, independently, H, C$_{1-20}$ alkyl, C$_{1-21}$ acyl, C$_{1-20}$ alkenyl, or C$_{1-20}$ alkynyl, and R$^{W4}$ is H, C$_{1-20}$ alkyl, $C_{1-20}$ alkenyl, or $C_{1-20}$ alkynyl, wherein each of $R^{W2}$, $R^{W3}$, $R^{W4}$, and $R^{W5}$ is optionally substituted with halo, hydroxyl, $C_{1-21}$ acyloxy, oxo, $C_{1-20}$ alkoxyl, or $C_{1-20}$ thioalkoxyl, optionally contains 1 to 2 phenyl or biphenyl moieties in and/or at the end of the carbon chain, and optionally contains 1 to 4 non-vicinal oxygen atoms in the carbon chain.

13. The method of claim 1, wherein:

X is selected from the group consisting of —N($R^{X1}$)C(O)V, —N($R^{X1}$)C(S)V, —N($R^{X1}$)C(O)N($R^{X2}$)V, —N($R^{X1}$)C(S)N($R^{X2}$)V, —N($R^{X1}$)C(O)OV, and —N($R^{X1}$)S(O)$_2$V, where each of $R^{X1}$ and $R^{X2}$ is, independently, H or $C_{1-6}$ alkyl, and V is a $C_{1-20}$ alkyl, $C_{1-20}$ alkenyl, or $C_{1-1-20}$ alkynyl group, optionally substituted with halo, hydroxyl, $C_{1-21}$ acyloxy, oxo, $C_{1-20}$ alkoxyl, or $C_{1-20}$ thioalkoxyl and optionally containing 1 or 2 phenyl or biphenyl moieties in and/or at the end of the carbon chain.

14. The method of claim 1, wherein:

W is selected from the group consisting of —C(O)N($R^{W1}$)$R^{W2}$, —(CH$_2$)$_c$S$R^{W3}$, —(CH$_2$)$_c$O(CH$_2$)$_d$CH(O$R^{W3}$)$R^{W4}$, —(CH$_2$)$_c$S(CH$_2$)$_d$CH(O$R^{W3}$)$R^{W4}$, —C(O)N($R^{W1}$)(CH$_2$)$_c$CH(O$R^{W3}$)$R^{W4}$, and —C(O)N($R^{W1}$)(CH$_2$)$_c$CH(O$R^{W3}$)(CH$_2$)$_e$O$R^{W5}$, wherein each of c and d is, independently, an integer of 1 to 4, e is an integer of 2 to 4, $R^{W1}$ is H or $C_{1-6}$ alkyl, $R^{W2}$ is $C_{1-20}$ alkyl, $C_{1-20}$ alkenyl, or $C_{1-20}$ alkynyl, each of $R^{W3}$ and $R^{W5}$ is, independently, H, $C_{1-20}$ alkyl, $C_{1-21}$ acyl, $C_{1-20}$ alkenyl, or $C_{1-20}$ alkynyl, and $R^{W4}$ is H, $C_{1-20}$ alkyl, $C_{1-20}$ alkenyl, or $C_{1-20}$ alkynyl, wherein each of $R^{W2}$, $R^{W3}$, $R^{W4}$ and $R^{W5}$ is optionally substituted with halo, hydroxyl, $C_{1-21}$ acyloxy, oxo, $C_{1-20}$ alkoxyl, or $C_{1-20}$ thioalkoxyl, optionally contains 1 to 2 phenyl or biphenyl moieties in and/or at the end of the carbon chain, and optionally contains 1 to 4 non-vicinal oxygen atoms in the carbon chain.

15. The method of claim 1, wherein said compound is

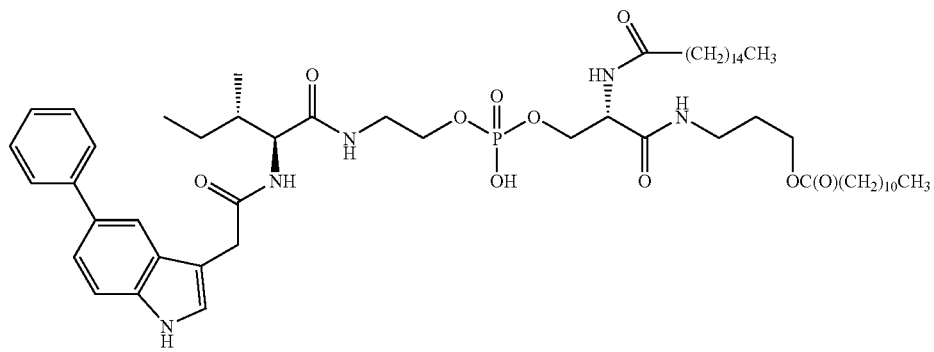

or a pharmaceutically acceptable salt thereof.

16. The method of claim 1, wherein said compound is

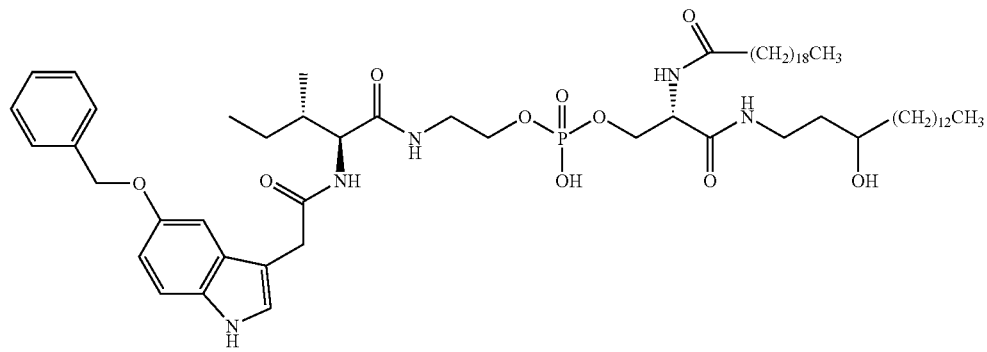

or a pharmaceutically acceptable salt thereof.

17. The method of claim 1, wherein said compound is
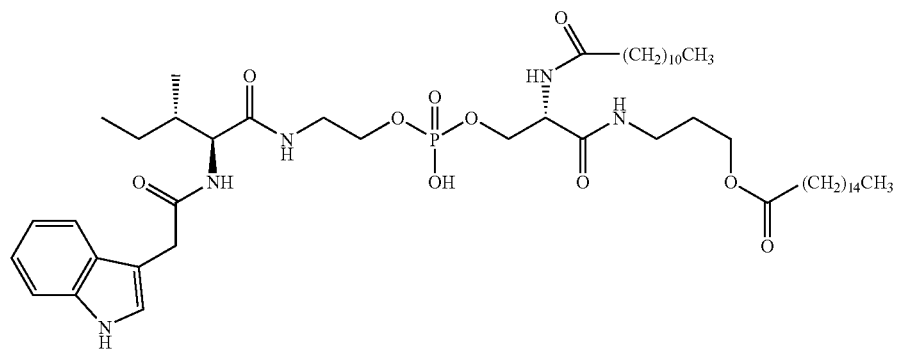
or a pharmaceutically acceptable salt thereof.
18. The method of claim 1, wherein said compound is
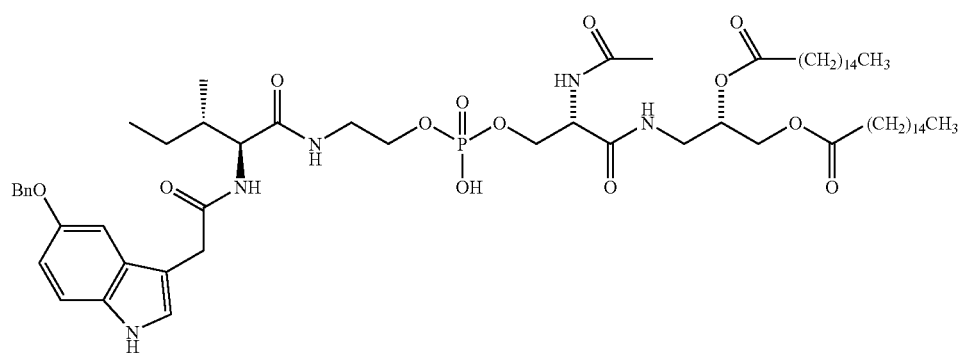
or a pharmaceutically acceptable salt thereof.
19. The method of claim 1, wherein said compound is
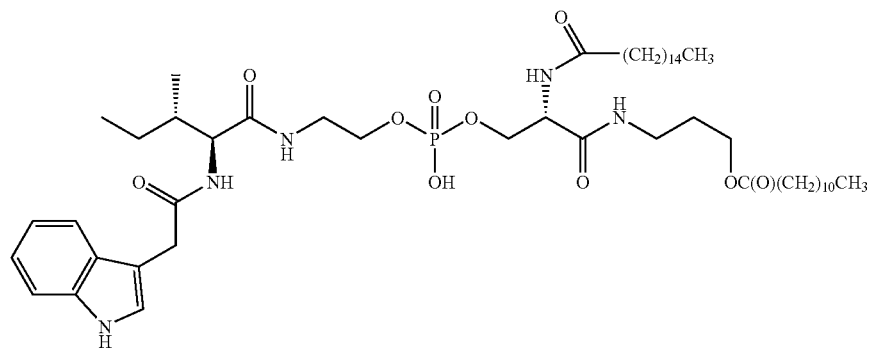
or a pharmaceutically acceptable salt thereof.

20. The method of claim 1, wherein said compound is
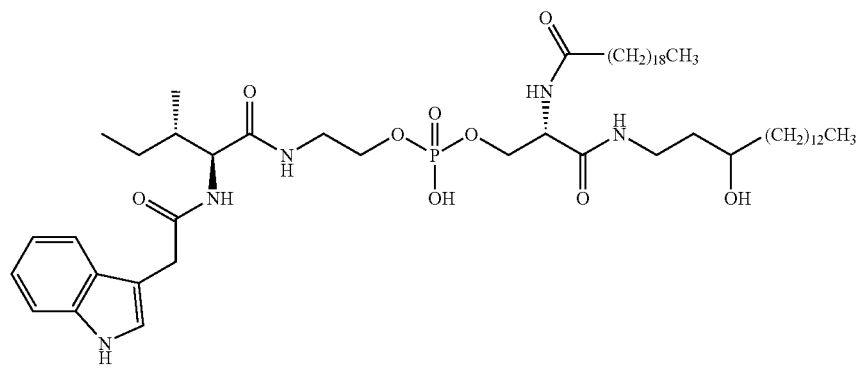
or a pharmaceutically acceptable salt thereof.
21. The method of claim 1, wherein said compound is
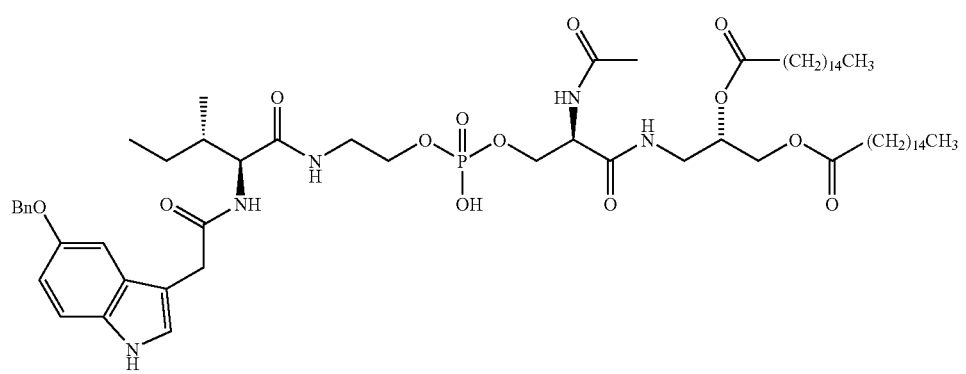
or a pharmaceutically acceptable salt thereof.
22. The method of claim 1, wherein said compound is
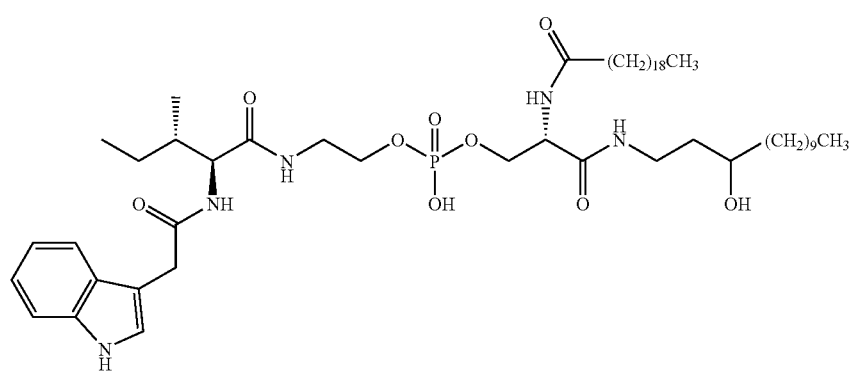
or a pharmaceutically acceptable salt thereof.

23. The method of claim 1, wherein said compound is
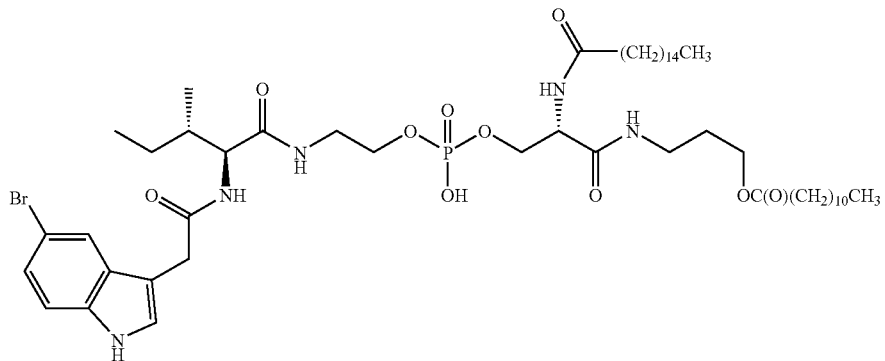
or a pharmaceutically acceptable salt thereof.
24. The method of claim 1, wherein said compound is
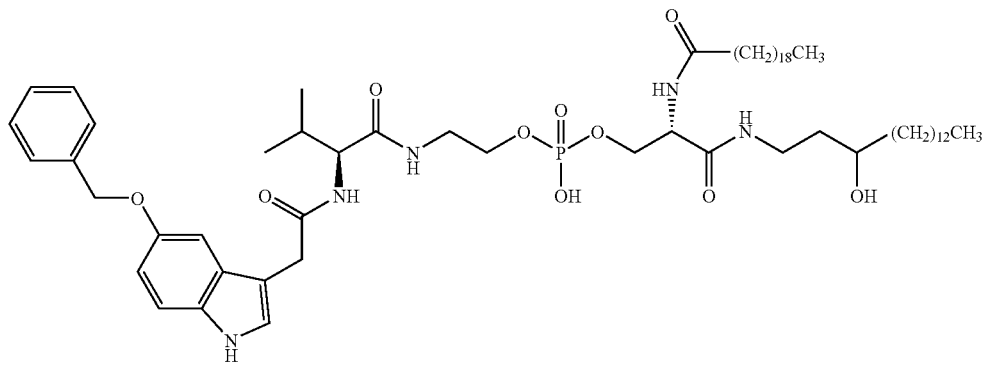
or a pharmaceutically acceptable salt thereof.
25. The method of claim 1, wherein said compound is
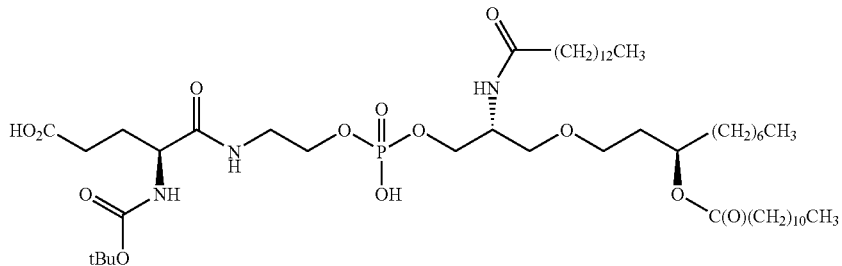
or a pharmaceutically acceptable salt thereof.

26. The method of claim 1, wherein said compound is
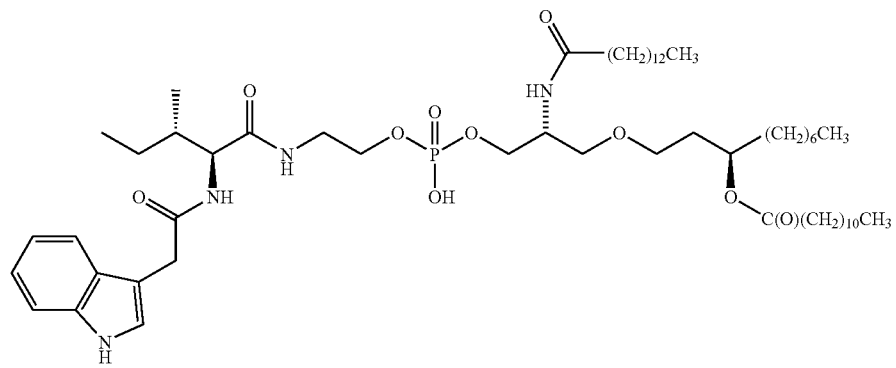
or a pharmaceutically acceptable salt thereof.
27. The method of claim 1, wherein said compound is
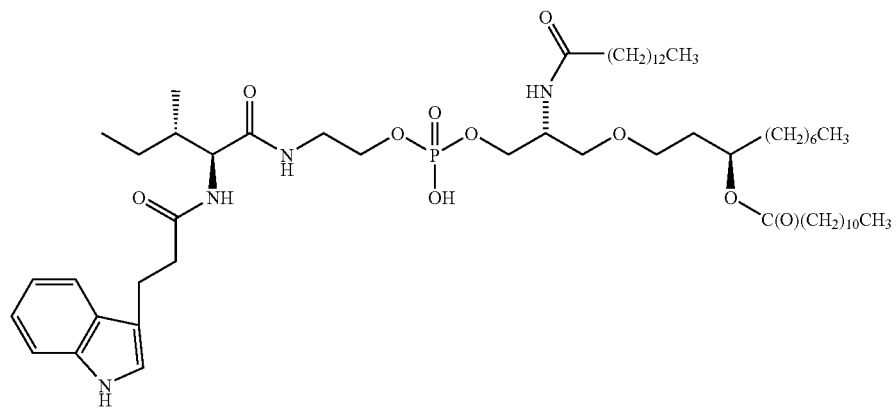
or a pharmaceutically acceptable salt thereof.
28. The method of claim 1, wherein said compound is
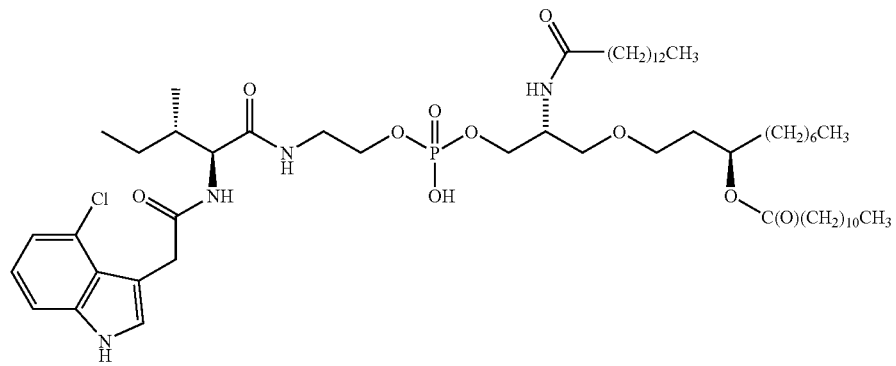
or a pharmaceutically acceptable salt thereof.

29. The method of claim 1, wherein said compound is
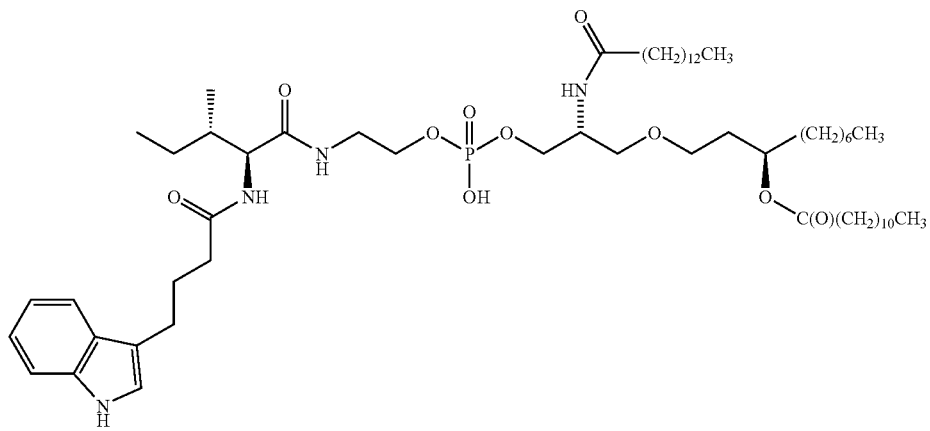
or a pharmaceutically acceptable salt thereof.
30. The method of claim 1, wherein said compound is
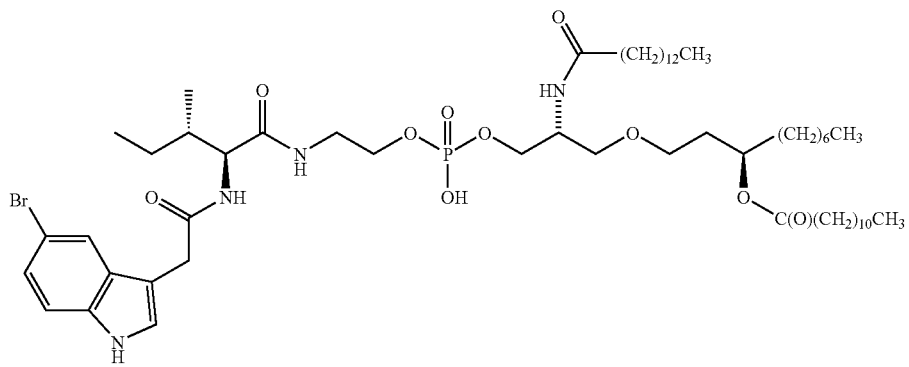
or a pharmaceutically acceptable salt thereof.
31. The method of claim 1, wherein said compound is
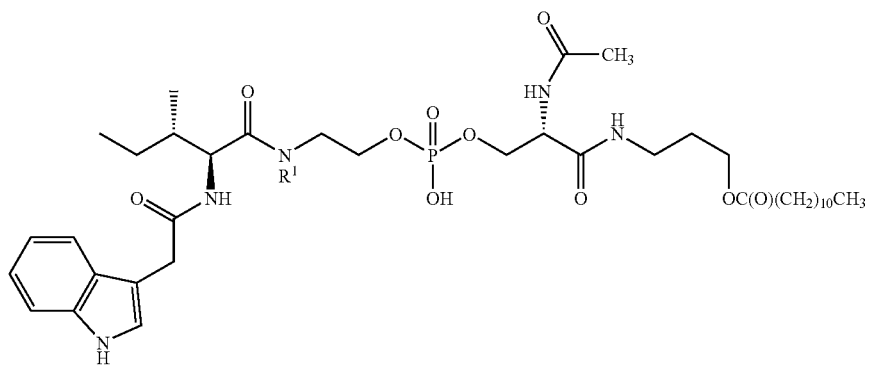
or a pharmaceutically acceptable salt thereof.

32. The method of claim 1, wherein said compound is
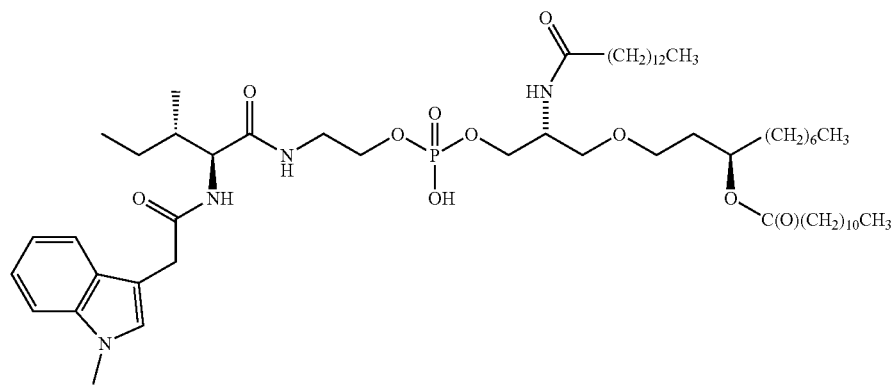
or a pharmaceutically acceptable salt thereof.
33. The method of claim 1, wherein said compound is
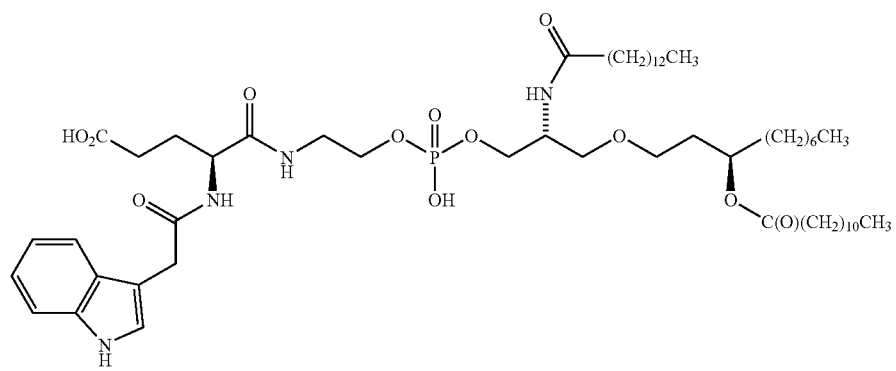
or a pharmaceutically acceptable salt thereof.
34. The method of claim 1, wherein said compound is
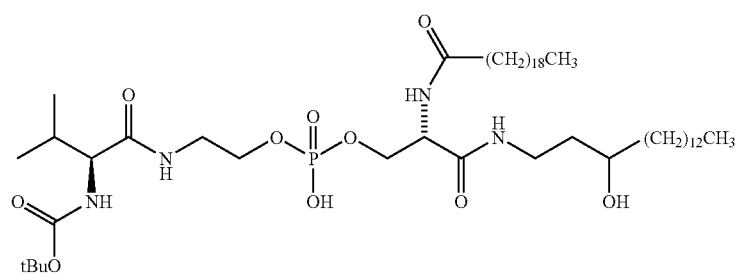
or a pharmaceutically acceptable salt thereof.
* * * * *